United States Patent [19]

Takasugi et al.

[11] Patent Number: 5,364,871

[45] Date of Patent: Nov. 15, 1994

[54] NEW THIAZOLE DERIVATIVES, AND PHARMACEUTICAL COMPOSITION COMPRISING THE SAME

[75] Inventors: Hisashi Takasugi, Sakai; Yousuke Katsura, Toyonaka; Tetsuo Tomishi, Minoo; Yoshikazu Inoue, Amagasaki, all of Japan

[73] Assignee: Fujisawa Pharmaceutical Co., Ltd., Osaka, Japan

[21] Appl. No.: 29,359

[22] Filed: Mar. 10, 1993

Related U.S. Application Data

[63] Continuation of Ser. No. 825,832, Jan. 28, 1992, abandoned, which is a continuation of Ser. No. 668,915, Mar. 13, 1991, abandoned, which is a continuation-in-part of Ser. No. 571,151, Aug. 23, 1990, abandoned.

[30] Foreign Application Priority Data

Sep. 15, 1989 [GB] United Kingdom ............. 8920977.9
Dec. 19, 1989 [GB] United Kingdom ............. 8928610.8
Jun. 11, 1990 [GB] United Kingdom ............. 9012962.8

[51] Int. Cl.$^5$ ..................... A61K 31/44; C07D 417/06
[52] U.S. Cl. ..................... 514/342; 546/275; 546/276; 546/250; 546/284
[58] Field of Search ............... 514/342, 235.5; 546/275, 276, 280, 284; 544/133

[56] References Cited

U.S. PATENT DOCUMENTS

4,735,957  4/1988  Takaya et al. ............... 546/121

FOREIGN PATENT DOCUMENTS

0225186  of 1985  Japan.

OTHER PUBLICATIONS

Journal of Pharamacology and Experimental Therapeutics, vol. 24, pp. 129–135, 1990.
Drugs, vol. 32, pp. 15–47, 1986.
Yamanouchi Pharmaceuticals, "Chemical Abstract" 103(3), 1985, #22581n.
Yamanouchi Pharmaceutical, "Chemical Abstract" 103(9), 1985, #71307m.

*Primary Examiner*—Mukund J. Shah
*Assistant Examiner*—Y. N. Gupta
*Attorney, Agent, or Firm*—Oblon, Spivak, McClelland, Maier & Neustadt

[57] ABSTRACT

A compound of the formula:

$$R^2-W \diagdown_{C=N} \diagup^{N} \underset{S}{\overset{}{\diagdown}} Y-A-R^1$$
$$R^3NH \diagup$$

wherein $R^1$ is amino, ureido, lower alkanoylamino, lower alkoxycarbonylamino, lower alkylsulfonylamino, lower alkoxy(lower)alkanoylamino, mono or di or trihalo(lower)alkanoylamino, hydroxy(lower)alkanoylamino, protected hydroxy(lower)alkanoylamino, or a group of the formula:

$$\underset{-C-R^5}{\overset{N-R^4}{\|}}$$

in which $R^4$ is hydrogen or sulfamoyl, $R^5$ is amino or lower alkoxy, $R^2$ is hydrogen, lower alkyl, lower alkoxy(lower)alkyl, di(lower)alkylamino(lower)alkyl, $(C_3-C_7)$-cycloalkyl, lower alkenyl or mono or di or trihalo(lower)alkyl; $R^3$ is hydrogen or lower alkyl; or $R^2$ and $R^3$ are linked together to form lower alkylene, Y is $$\underset{N}{\diagdown}\overset{R^6}{\diagup},$$

in which $R^6$ is hydrogen, A is lower alkylene, and W is NH; or $R^2$-W is piperidino or morpholino, or pharmaceutically acceptable salt thereof.

6 Claims, No Drawings

NEW THIAZOLE DERIVATIVES, AND PHARMACEUTICAL COMPOSITION COMPRISING THE SAME

This application is a continuation of application Ser. No. 07/825,832, filed on Jan. 28, 1992, now abandoned, which is a file wrapper continuation of Ser. No. 07/668,915, filed on Mar. 13, 1991, which is a continuation-in-part of Ser. No. 07/571,151 filed on Aug. 23, 1990, both now abaondoned.

This invention relates to new thiazole derivatives and pharmaceutically acceptable salts thereof.

More particularly, it relates to thiazole derivatives and pharmaceutically acceptable salts thereof which have antiulcer activity and $H_2$-receptor antagonism, to processes for the preparation thereof, to a pharmaceutical composition comprising the same and to a method for the treatment of ulcer in human being or animals.

Accordingly, one object of this invention is to provide new thiazole derivatives and pharmaceutically acceptable salts thereof which possess antiulcer activity and $H_2$-receptor antagonism.

Another object of this invention is to provide processes for the preparation of said thiazole derivatives and salt thereof.

A further object of this invention is to provide a pharmaceutical composition comprising, as an active ingredient, said thiazole derivatives or pharmaceutically acceptable salts thereof.

Still further object of this invention is to provide a therapeutical method for the treatment of ulcer in human being or animals.

The thiazole derivatives of this invention are new and can be represented by the following general formula (I):

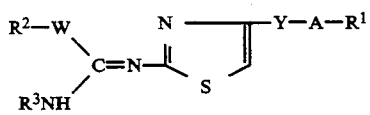

wherein
$R^1$ is amino which may have suitable substituent(s), hydroxy, halogen, cyano, acyl, heterocyclic thio, heterocyclic group or a group of the formula:

in which
$R^4$ is hydrogen, cyano or acyl, and
$R^5$ is amino or lower alkoxy,
$R^2$ and $R^3$ are each hydrogen, acyl, lower alkyl which may have suitable substituent(s), ($C_3$–$C_7$)-cycloalkyl or lower alkenyl; or
$R^2$ and $R^3$ are linked together to form lower alkylene,
Y is

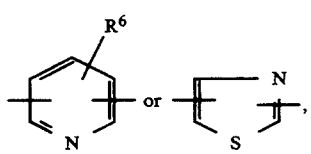

in which $R^6$ is hydrogen or halogen,
A is bond or lower alkylene, and
W is NH; or
$R^2$-W is pyperidino or morpholino, provided that when $R^1$ is amino which may have suitable substituent(s) and
A is bond; or $R^1$ is lower alkylthioureido and A is lower alkylene, then Y is 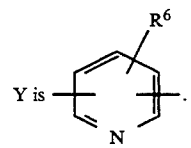.

The object compound (I) or a salt thereof can be prepared by processes as illustrated in the following reaction schemes.

Process 1

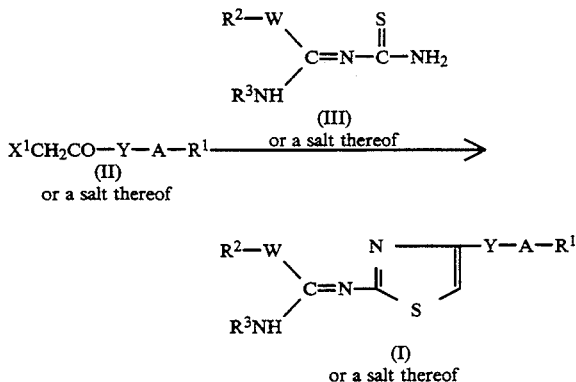

Process 2

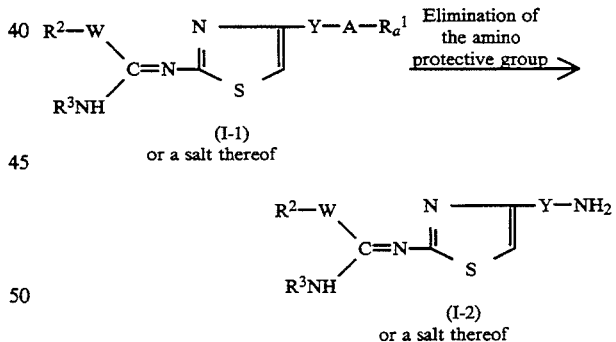

Process 3

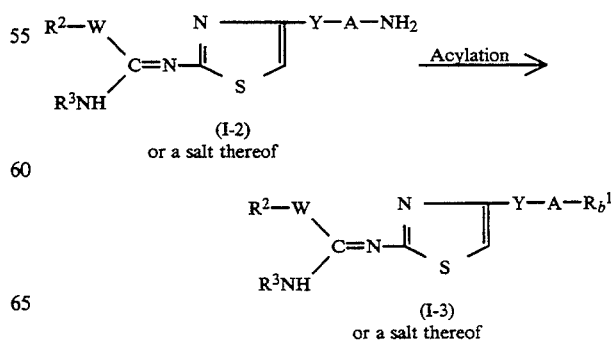

Process 4

3

-continued

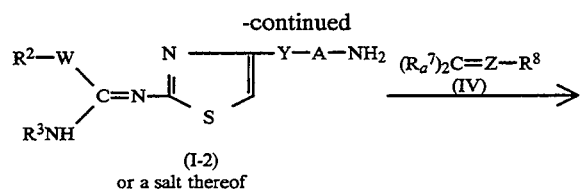
(I-2) or a salt thereof

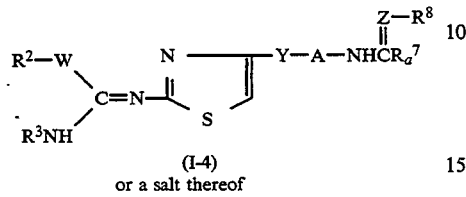
(I-4) or a salt thereof

Process 5

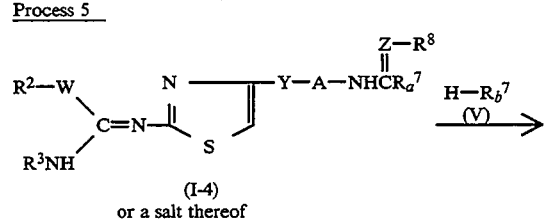
(I-4) or a salt thereof

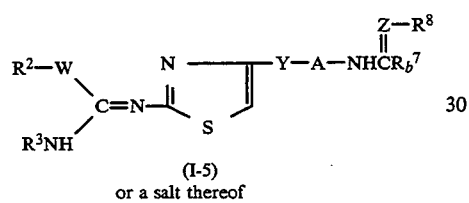
(I-5) or a salt thereof

Process 6

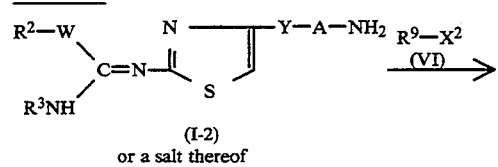
(I-2) or a salt thereof

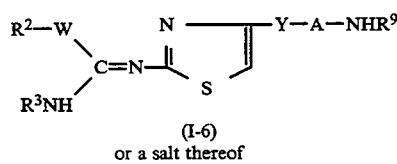
(I-6) or a salt thereof

Process 7

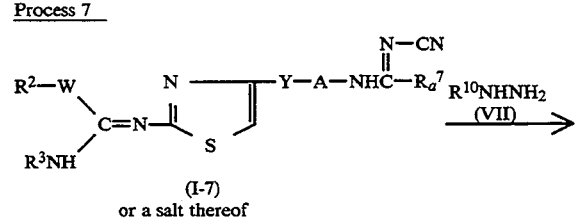
(I-7) or a salt thereof

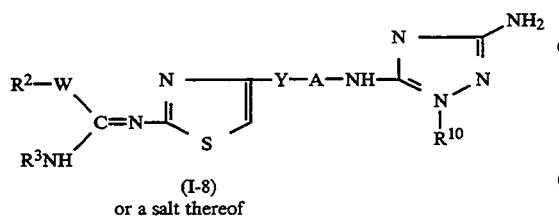
(I-8) or a salt thereof

Process 8

4

-continued

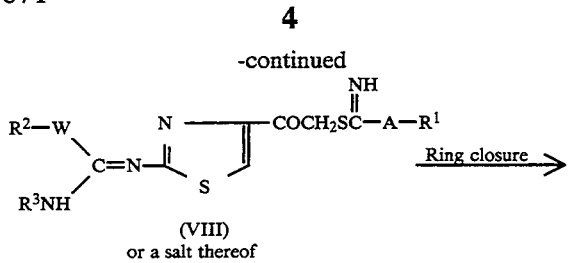
(VIII) or a salt thereof   Ring closure →

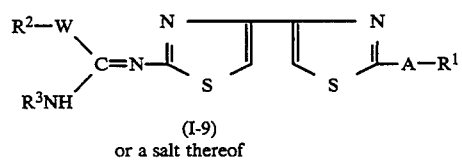
(I-9) or a salt thereof

Process 9

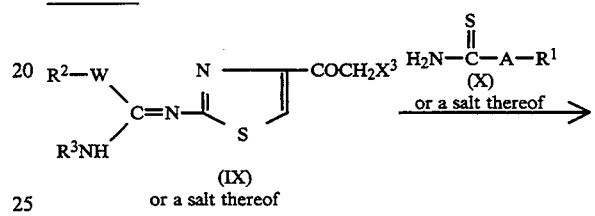
(IX) or a salt thereof

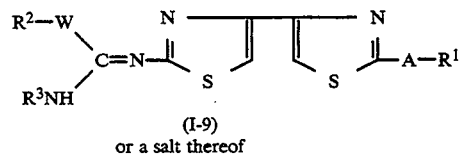
(I-9) or a salt thereof

Process 10

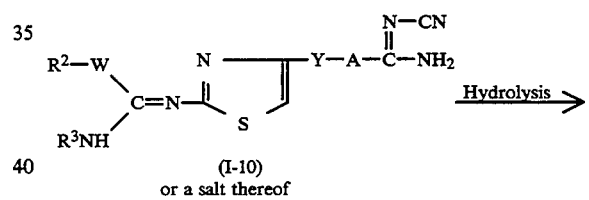
(I-10) or a salt thereof   Hydrolysis →

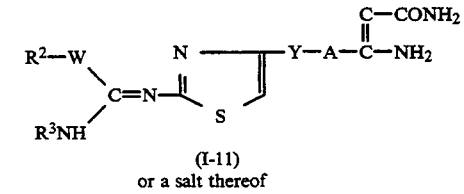
(I-11) or a salt thereof

Process 11

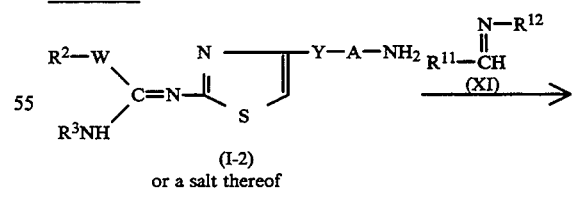
(I-2) or a salt thereof

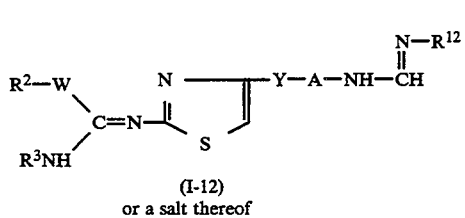
(I-12) or a salt thereof

Process 12

-continued

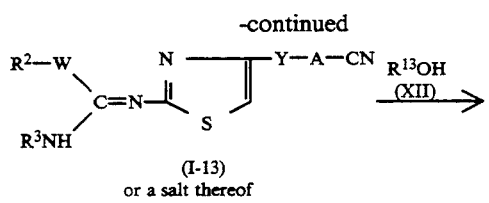
(I-13) or a salt thereof

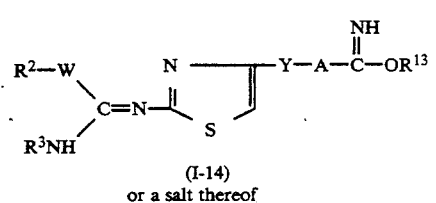
(I-14) or a salt thereof

Process 13

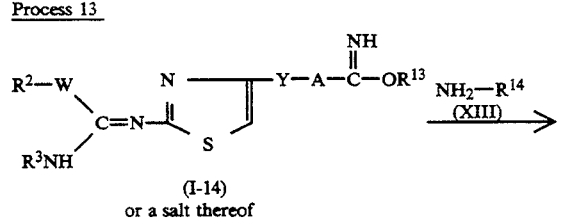
(I-14) or a salt thereof

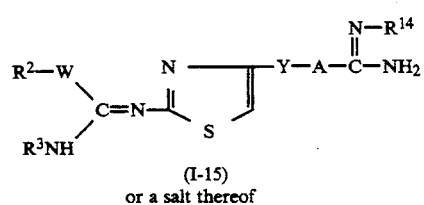
(I-15) or a salt thereof

Process 14

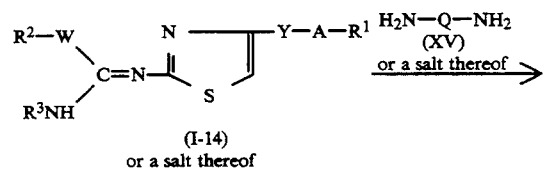
(I-14) or a salt thereof

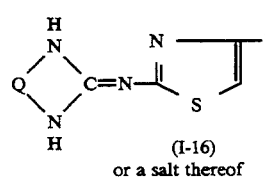
(I-16) or a salt thereof

Process 15

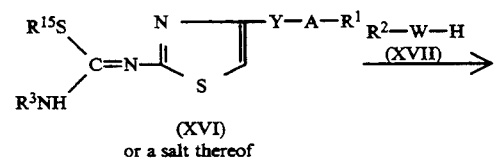
(XVI) or a salt thereof

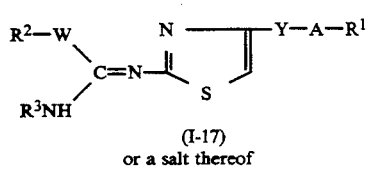
(I-17) or a salt thereof

Process 16

-continued

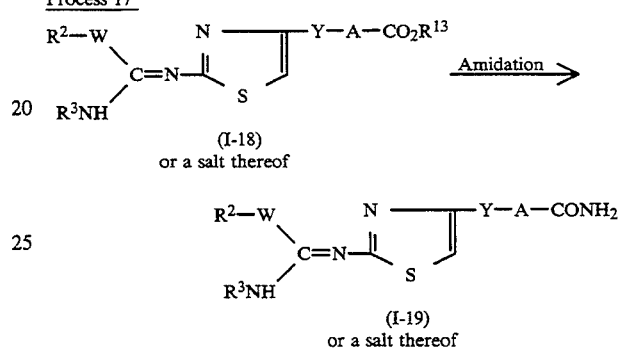
(I-14) or a salt thereof (I-18) or a salt thereof

Process 17

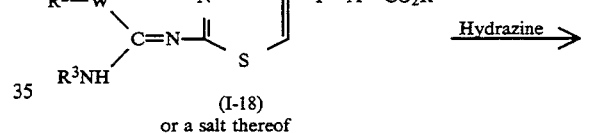
(I-18) or a salt thereof (I-19) or a salt thereof

Process 18

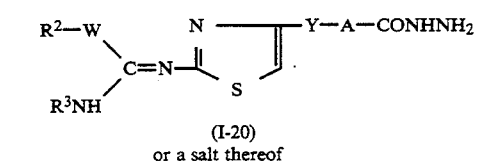
(I-18) or a salt thereof

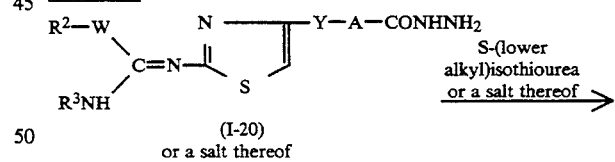
(I-20) or a salt thereof

Process 19

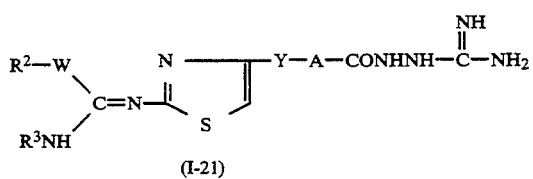
(I-20) or a salt thereof

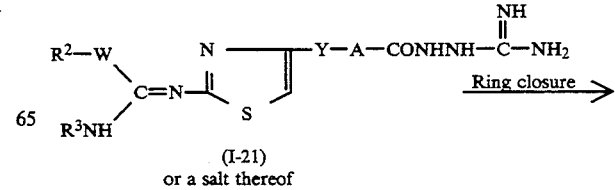
(I-21) or a salt thereof

Process 20

(I-21) or a salt thereof

7
-continued

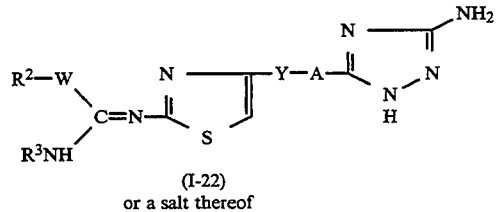
(I-22) or a salt thereof

Process 21

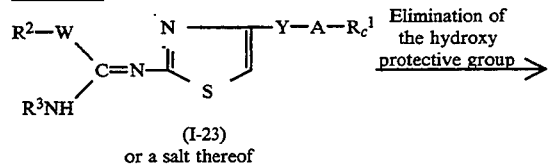
(I-23) or a salt thereof

Elimination of the hydroxy protective group →

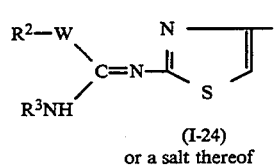
(I-24) or a salt thereof

Process 22

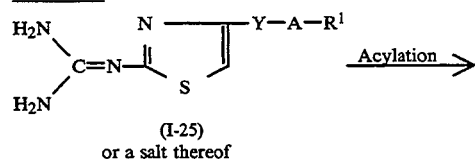
(I-25) or a salt thereof

Acylation →

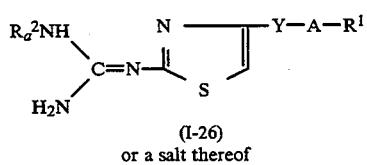
(I-26) or a salt thereof

Process 23

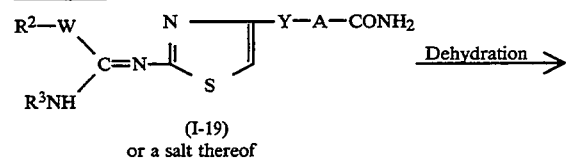
(I-19) or a salt thereof

Dehydration →

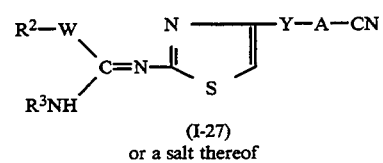
(I-27) or a salt thereof

Process 24

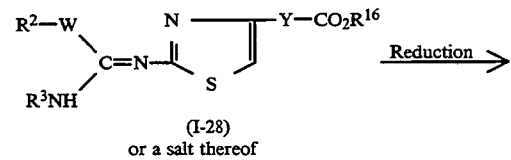
(I-28) or a salt thereof

Reduction →

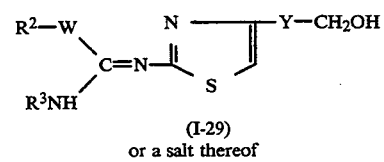
(I-29) or a salt thereof

8
-continued

Process 25

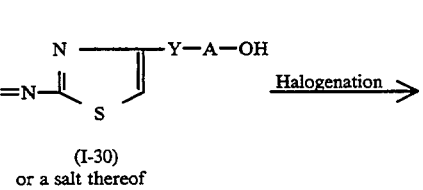
(I-30) or a salt thereof

Halogenation →

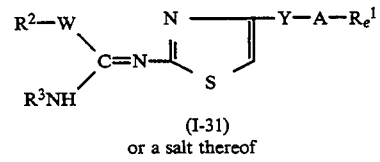
(I-31) or a salt thereof

Process 26

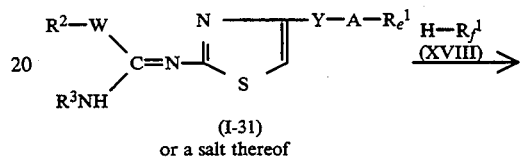
(I-31) or a salt thereof $H-R_f^1$ (XVIII) →

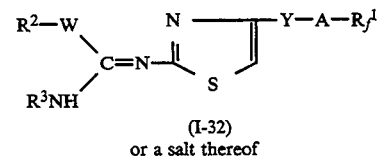
(I-32) or a salt thereof

Process 27

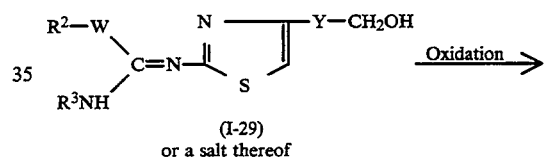
(I-29) or a salt thereof

Oxidation →

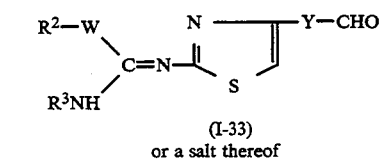
(I-33) or a salt thereof

Process 28

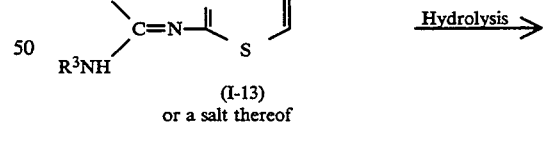
(I-13) or a salt thereof

Hydrolysis →

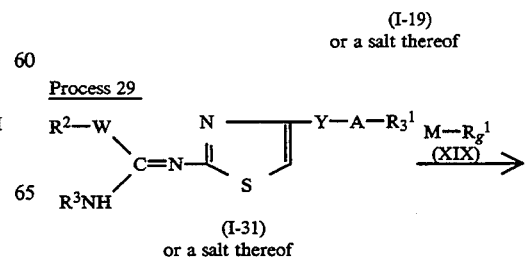
(I-19) or a salt thereof

Process 29

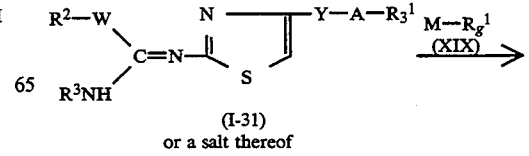
(I-31) or a salt thereof $M-R_g^1$ (XIX) →

-continued

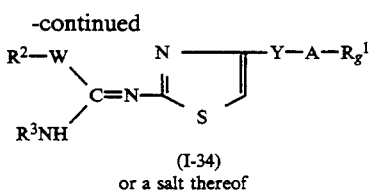
(I-34) or a salt thereof

Process 30

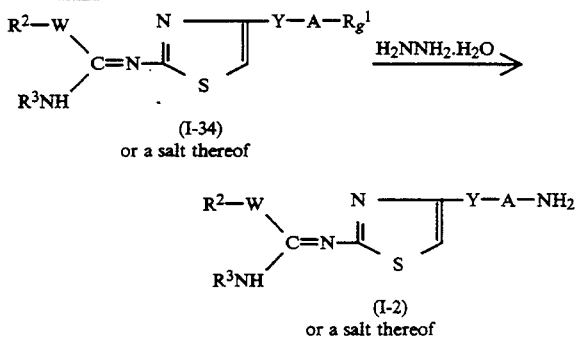
(I-34) or a salt thereof (I-2) or a salt thereof

Process 31

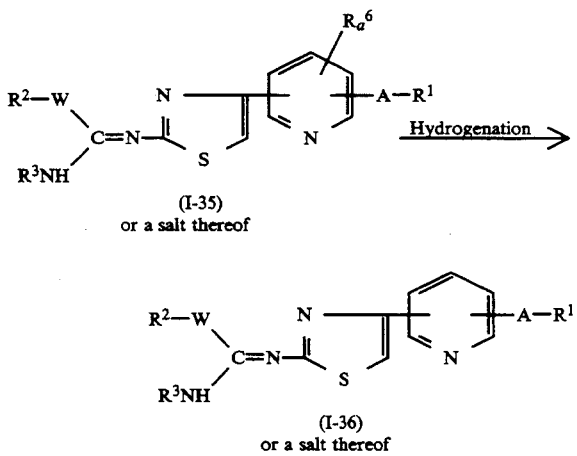
(I-35) or a salt thereof (I-36) or a salt thereof

Process 32

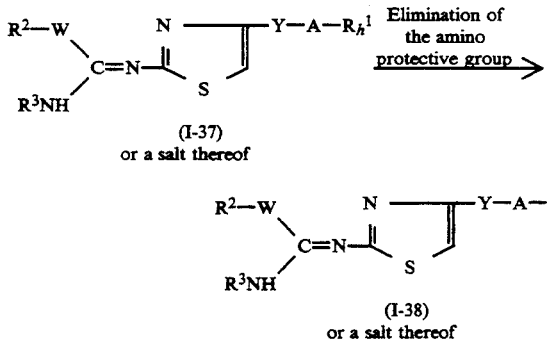
(I-37) or a salt thereof (I-38) or a salt thereof wherein
$R^1$, $R^2$, $R^3$, $R^4$, $R^5$, $R^6$, Y, A and W are each as defined above,
$R_a{}^1$ is protected amino,
$R_b{}^1$ is acylamino,
$R_c{}^1$ is acylamino having protected hydroxy,
$R_d{}^1$ is acylamino having hydroxy,
$R_e{}^1$ is halogen,
$R_f{}^1$ is heterocyclic thio,
$R_g{}^1$ is imido,
$R_h{}^1$ is acylamino having protected amino,
$R_i{}^1$ is acylamino having amino, $R_a{}^2$ is acyl,
$R_a{}^6$ is halogen,
$R_a{}^7$ is lower alkylthio or protected hydroxy,
$R_b{}^7$ is amino which may have suitable substituent(s),
$R^8$ is hydrogen, cyano, nitro or acyl,
$R^9$ is suitable substituent in $R^1$ as defined above,
$R^{10}$ is hydrogen or lower alkyl,
$R^{11}$ is protected hydroxy,
$R^{12}$ is acyl,
$R^{13}$ is lower alkyl,
$R^{14}$ is acyl or cyano,
$R^{15}$ is lower alkyl,
$R^{16}$ is lower alkyl,
$X^1$ is acid residue,
$X^2$ is acid residue or protected hydroxy,
$X^3$ is acid residue,
Z is N or CH,
Q is lower alkylene, and
M is alkali metal.

In the above and subsequent descriptions of the present specification, suitable examples of the various definitions to be included within the scope of the invention are explained in detail in the following.

The term "lower" is intended to mean a group having 1 to 6 carbon atom(s) preferably 1 to 4 carbon atom(s), unless otherwise provided.

Suitable "lower alkoxy" may include methoxy, ethoxy, propoxy, isopropoxy, butoxy, pentyloxy, hexyloxy, and the like.

Suitable "lower alkylthio" may include methylthio, ethylthio, propylthio, isopropylthio, butylthio, isobutylthio, tert-butylthio, pentylthio, hexylthio, and the like.

Suitable "acid residue" may include halogen such as chloro, bromo, fluoro and iodo.

Suitable "lower alkylene" and lower alkylene moiety formed by linkage of $R^2$ and $R^3$ may be straight or branched one such as methylene, ethylene, trimethylene, propylene, tetramethylene, pentamethylene, hexamethylene, and the like, in which the preferable one is $C_1$-$C_4$ alkylene and the most preferable one is methylene and ethylene.

Suitable "amino which may have suitable substituent(s)" is conventional one used in a pharmaceutical field and may include amino, mono or di(lower)alkylamino (e.g. methylamino, dimethylamino, ethylamino, butylamino, etc.), lower alkenylamino (e.g. vinylamino, propenylamino, etc.), lower alkynylamino (e.g. ethynylamino, propynylamino, etc.), hydroxy(lower)alkylamino (e.g. hydroxymethylamino, hydroxyethylamino, hydroxypropylamino, etc.), lower alkoxy(lower)alkylamino (e.g. methoxymethylamino, etc.), mono or di(lower)alkylamino(lower)alkylamino (e.g. methylaminomethylamino, dimethylaminoethylamino, etc.), protected amino such as acylamino, in which acyl is as mentioned below, heterocyclic amino, in which heterocyclic group is as mentioned below, cyclo(lower)alkenylamino which may have one or more, preferably one to three suitable substituent(s) such as amino and oxo [e.g. (1-amino-3,4-dioxo-1-cyclobuten-2-yl)amino), etc.], imino (e.g. succinimido, phthalimido, etc.), a group of the formula:

$$\begin{array}{c} Z-R^8 \\ \| \\ -NHC-R^7 \end{array}$$

wherein $R^8$ and Z are each as defined above, and $R^7$ is hydrogen, lower alkylthio, protected hydroxy or amino which may have suitable substituent(s), each of which is as mentioned above or below, and the like.

Suitable "lower alkyl" may be a straight or branched one such as methyl, ethyl, propyl, isopropyl, butyl, isobutyl, tert-butyl, pentyl, isopentyl, hexyl or the like, in which the preferable one is $C_1$–$C_4$ alkyl and the more preferable one is methyl or ethyl.

Suitable "acyl" and the acyl group in the term "acylamino" may include carbamoyl, thiocarbamoyl, sulfamoyl, an aliphatic acyl, an aromatic acyl, a heterocyclic acyl and an aliphatic acyl substituted with aromatic or heterocyclic group(s) derived from carbamic, sulfonic, carboxylic or carbonic acid, and their thio acids.

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, etc.), lower alkenoyl (e.g. acryloyl, methacryloyl, crotonoyl, etc.), $C_3$–$C_7$-cycloalkanecarbonyl (e.g. cyclopropanecarbonyl, cyclobutanecarbonyl, cyclopentanecarbonyl, cyclohexanecarbonyl, cycloheptanecarbonyl, etc.), lower alkoxyalyl (e.g. methoxalyl, ethoxalyl, etc.), lower alkanoylcarbonyl (e.g. pyruvoyl, etc.), and the like.

The aromatic acyl may include aroyl (e.g. benzoyl, nitrobenzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, 1-oxonicotinoyl, isonicotinoyl, thiazolylcarbonyl, thiadiazolylcarbonyl, tetrazolylcarbonyl, tetrahydrofurylcarbonyl, pyperidylcarbonyl, morpholinocarbonyl, etc.), and the like.

The aliphatic acyl substituted with aromatic group(s) may include phenyl(lower)alkanoyl (e.g. phenylacetyl phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl thiadiazolylpropionyl, and the like.

These acyl groups may be further substituted with suitable substituent(s) such as hydroxy, amino, guanidino, carboxy, oxo, lower alkyl (e.g. methyl, ethyl, propyl, isopropyl butyl, pentyl, hexyl, etc.), ($C_3$–$C_7$)-cycloalkyl (e.g. cyclopropyl cyclobutyl, cyclopentyl, cyclohexyl, cycloheptyl etc.), lower alkenyl (e.g. vinyl, allyl etc.), halogen (e.g. chloro, bromo, iodo, fluoro), lower alkoxy (e.g. methoxy, ethoxy, propoxy, isopropoxy, butoxy, pentyloxy, hexyloxy, etc.), lower alkoxycarbonyl(lower)alkoxy (e.g. methoxycarbonylmethoxy, etc.), lower alkylthio (e.g. methylthio, ethylthio, propylthio, isopropylthio, butylthio, pentylthio, hexylthio, etc.), heterocyclic group as mentioned below, heterocyclic(lower)alkylthio (e.g. furylmethylthio, thiazolylmethylthio, etc.), heterocyclic(lower)alkylsulfinyl (e.g. furylmethylsulfinyl, thiazolylmethylsulfinyl, etc.), nitro, heterocyclic(lower)alkylaryloxy(lower)alkyl (e.g. pyrrolidinylmethylphenoxypropyl, etc.), acyl as mentioned above, protected amino in which the amino protective moiety may be the same as those herein, aryl (e.g. phenyl, etc.), aroyl (e.g. benzoyl, etc.), aryloxy (e.g., benzyloxy, tolyloxy, etc.), protected hydroxy such as acyloxy, for example, lower alkanoyloxy (e.g. formyloxy, acetyloxy, propionyloxy, butyryloxy, isobutyryloxy, valeryloxy, isovaleryloxy, pivaloyloxy, hexanoyloxy, etc.), lower alkylamino (e.g. methylamino, dimethylamino, ethylamino, etc.), aminoprotective group as aftermentioned, and the like, and the preferable acyl having such substituent(s) may be lower alkoxy(lower)alkanoyl (e.g., methoxyacetyl ethoxyacetyl, etc.), lower alkoxycarbonyl (e.g. tert-butoxycarbonyl, etc.), lower alkanoyloxy(lower)alkanoyl (e.g., acetoxyacetyl, acetoxypropionyl, etc.), N-lower alkylcarbamoyl (e.g. N-methylcarbamoyl, N-ethylcarbamoyl, N-propylcarbamoyl, N-isopropylcarbamoyl, etc.), aroylthiocarbamoyl (e.g. benzoylthiocarbamoyl, etc.), heterocyclic(lower)alkylthio(lower)alkanoyl (e.g. furylmethylthioacetyl, etc.), N-lower alkylthiocarbamoyl (e.g. N-methylthiocarbamoyl, etc.), halo(lower)alkanoyl (e.g. trifluoroacetyl, etc.), hydroxy(lower)alkanoyl (e.g. hydroxyacetyl, etc.), amino(lower)alkanoyl (e.g. aminoacetyl, etc.), lower alkylamino(lower)alkanoyl (e.g. dimethylaminoacetyl, etc.), lower alkylthio(lower)alkanoyl (e.g. methylthioacetyl, etc.), lower alkoxycarbonyl(lower)alkoxy(lower)alkanoyl (e.g. methoxycarbonylmethoxyacetyl, etc.), N-lower alkoxycarbonylamino(lower)alkanoyl (e.g. N-t-butoxycarbonylaminoacetyl, etc.), lower alkyl ($C_3$–$C_7$)-cycloalkanecarbonyl (e.g. methylcyclopropanecarbonyl, etc.), N-aminocarbamoyl, N-guanidinocarbamoyl, N-lower alkylsulfamoyl (e.g. N-methylsulfamoyl, etc.).

Suitable "heterocyclic group" and heterocyclic moiety in the terms "heterocyclic amino" and "heterocyclic thio" may include saturated or unsaturated, monocyclic or polycyclic heterocyclic group containing at least one hetero-atom such as an oxygen, sulfur nitrogen atom and the like. Especially preferably heterocyclic group may be 5 or 6-membered aromatic heteromonocyclic group (e.g. pyrrolyl, imidazolyl, pyrazolyl, triazolyl, tetrazolyl, pyridyl, pyrazinyl, pyrimidinyl, pyridazinyl, thiazolyl, thiadiazolyl, etc.), 5- or 6-membered aliphatic heteromonocyclic group (e.g. morpholinyl, pyrrolidinyl, imidazolidinyl, pyrazolidinyl, piperidyl, piperazinyl, dithiacyclopentyl, etc.), unsaturated condensed heterocyclic group containing 1 to 3 nitrogen atom(s) (e.g. benzimidazolyl, etc.), unsaturated condensed heterocyclic group containing 1 to 2 sulfur atom(s) and 1 to 3 nitrogen atom(s) (e.g. benzothiazolyl, benzoisothiazolyl benzothiadiazolyl etc.), and the like. Thus defined heterocyclic moiety may have suitable substituent(s) such as amino, oxo, halogen as chloro, lower alkyl as defined above, and the like. Preferable example of such groups are triazolyl having amino and lower alkyl (e.g. 3-amino-1-methyl-1H-triazol-5-yl, etc.), triazolyl having amino (e.g. 3-amino-1H-triazolyl-5-yl, etc.), benzoisothiazolyl having oxo (e.g. 1,1-dioxobenzoisothiazolyl, etc.).

Suitable amino-protective group in the term "protected amino" may include ar(lower)alkyl such as benzyl, benzhydryl, phenethyl and the like, and acyl as mentioned above.

Suitable hydroxy-protective group in the term "protected hydroxy" may include aforesaid acyl, ar(lower)alkyl (e.g. benzyl, trityl, etc.) lower alkoxy(lower)alkyl (e.g. methoxymethyl, 1-methyl-1-methoxyethyl, methoxypropyl, etc.), tetrahydropyranyl, aryl (e.g. phenyl, etc.), lower alkyl (e.g. methyl, ethyl, etc.), and the like.

Suitable "halogen" may be chloro, bromo, fluoro and iodo.

Suitable "lower alkyl which may have suitable substituent(s)" is conventional one used in a pharmaceutical field and may include lower alkyl as mentioned above, mono or di or trihalo(lower)alkyl such as trifluoro(lower)alkyl (e.g. trifluoromethyl, trifluoroethyl, etc.), lower alkoxy(lower)alkyl (e.g. methoxymethyl, methoxyethyl, etc.), di(lower)alkylamino(lower)alkyl (e.g. dimethylaminomethyl, dimethylaminoethyl, etc.), and the like. .

Suitable "imido" may include succinimido, phthalimido, and the like.

Suitable "acylamino having protected hydroxy" may include acylamino as mentioned above which is substituted by a protected hydroxy as exemplified above, for example, protected hydroxy(lower)alkanoylamino such as lower alkanoyloxy(lower)alkanoylamino (e.g. acetoxyacetylamino, etc.), and the like.

Suitable "acylamino having hydroxy" may include acylamino as mentioned above which is substituted by hydroxy, for example, hydroxy(lower)alkanoylamino (e.g. hydroxyacetylamino, etc.), and the like.

Suitable "acylamino having protected amino" may include acylamino as mentioned above which is substituted by a protected amino as exemplified above, for example, protected amino(lower)alkanoylamino such as lower alkoxycarbonylamino(lower)alkanoylamino (e.g. t-butoxycarbonylaminoacetylamino, etc.), and the like.

Suitable "acylamino having amino" may include acylamino as mentioned above which is substituted by amino, for example, amino(lower)alkanoylamino (e.g. aminoacetylamino, etc.), and the like.

Suitable "alkali metal" may include sodium, potassium, and the like.

Suitable "lower alkylthioureido" may include 3-lower alkylthioureido (e.g. 3-methylthioureido, etc.), and the like.

Suitable "(C$_3$–C$_7$)-cycloalkyl" may include cyclopropyl, cyclobutyl, cyclopentyl, cyclohexyl, cycloheptyl, and the like.

Suitable "lower alkenyl" may include vinyl, allyl, and the like.

Suitable pharmaceutically acceptable salts of the object compound (I) are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an acidic amino acid [e.g. aspartic acid salt, glutamic acid salt, etc.], and the like.

With respect to the salt of the compounds (I-1) to (I-38), (II), (III), (VIII), (IX), (X), (XIV), (XV) and (XVI) in the Processes 1 to 32, it is to be noted that these compounds are included within the scope of the compound (I), and accordingly the suitable examples of the salts of these compounds are to be referred to those as exemplified for the object compound (I).

Particularly, the preferred embodiments of $R^1$, $R^2$, $R^3$, $R^4$, $R^5$, $R^6$, Y and A are as follows.

$R^1$ is amino, mono or di(lower)alkylamino (e.g. dimethylamino, etc.), acylamino, for example, ureido, lower alkanoylamino (e.g. formylamino, acetylamino, propionylamino, butyrylamino, isobutyrylamino, pivaloylamino, etc.), lower alkoxycarbonylamino (e.g. methoxycarbonylamino, ethoxycarbonylamino, butoxycarbonylamino, isobutoxycarbonylamino, etc.), lower alkylsulfonylamino (e.g. mesylamino, etc.), lower alkoxy(lower)alkanoylamino (e.g. methoxyacetylamino, etc.), mono or di or trihalo(lower)alkanoylamino (e.g. trifluoroacetylamino, etc.), hydroxy(lower)alkanoylamino (e.g. hydroxyacetylamino, etc.), protected hydroxy(lower)alkanoylamino such as lower alkanoyloxy(lower)alkanoylamino (e.g. acetoxyacetylamino, acetoxypropionylamino, etc.), amino(lower)alkanoylamino (e.g. aminoacetylamino, etc.), protected amino(lower)alkanoylamino such as lower alkoxycarbonylamino(lower)alkanoylamino (e.g. t-butoxycarbonylaminoacetylamino, etc.), lower alkoxycarbonyl(lower)alkoxy(lower)alkanoylamino (e.g. methoxycarbonylmethoxyacetylamino, etc.), lower alkylthio(lower)alkanoylamino (e.g. methylthioacetylamino, etc.), lower alkanoyl(lower)alkanoylamino (e.g. acetylpropionylamino, etc.), mono or di(lower)alkylamino(lower)alkanoylamino (e.g. dimethylaminoacetylamino, etc.), heterocyclic(lower)alkylthio(lower)alkanoylamino such as 5- or 6-membered heteromonocyclic(lower)-alkylthio(lower)alkanoylamino (e.g. furylmethylthioacetylamino, etc.), lower alkylureido such as 3-lower alkylureido (e.g. 3-methylureido, 3-ethylureido, 3-propylureido, 3-isopropylureido, etc.), lower alkylthioureido such as 3-lower alkylthioureido (e.g. 3-methylthioureido, etc.), (C$_3$–C$_7$)-cycloalkyl(lower)alkanoylamino (e.g. cyclohexylacetylamino, etc.), (C$_3$–C$_7$)-cycloalkanecarbonylamino (e.g. cyclopropanecarbonylamino, cyclobutanecarbonylamino, cyclopentanecarbonylamino, cyclohexanecarbonylamino, cycloheptanecarbonylamino, etc.), (C$_3$–C$_7$)-cycloalkanecarbonylamino having oxo (e.g. oxocyclohexanecarbonylamino, etc.), lower alkyl(C$_3$–C$_7$)-cycloalkanecarbonylamino (e.g. methylcyclopropanecarbonylamino, etc.), heterocycliccarbonylamino such as 5- or 6-membered heteromonocycliccarbonylamino (e.g. furoylamino, nicotinoylamino, tetrahydrofurylcarbonylamino, pyperidylcarbonylamino, etc.), (C$_3$–C$_7$)-cycloalkenylamino having amino and oxo (e.g. aminodioxocyclobutenylamino, etc.), imido (e.g. phthalimido, etc.), heterocyclic amino, for example, optionally benzene-fused 5- or 6-heteromonocyclic amino which may be substituted by one or more substituent(s) selected from the group consisting of lower alkyl amino and oxo such as triazolylamino substituted by amino (e.g. 3-aminotriazolylamino, etc.), triazolylamino substituted by amino and lower alkyl (e.g. 3-amino-1-methyltriazolylamino, etc.) and benzoisothiazolylamino substituted by oxo (e.g. 1,1-dioxobenzoisothiazolylamino, etc.), 2-cyano-3-lower alkylguanidino (e.g. 2-cyano-3-methylguaidino, etc.), 2-lower alkanesulfonyl-3-lower alkylguanidino (e.g. 2-methanesulfonyl-3-methylguanidino, etc.), 2-lower alkanesulfonylguanidio (e.g. 2-ethanesulfonylguanidino, etc.), (1-lower alkylamino-2-nitrovinyl)amino (e.g. (1-methylamino-2-nitrovinyl)amino, etc.); hydroxy; halogen (e.g. chloro, etc.); cyano; acyl such as carbamoyl, aminocarbamoyl, guanidinocarbamoyl, (C$_3$–C$_7$)-cycloalkylcarbamoyl (e.g. cyclopentyl-carbamoyl, cyclohexylcarbamoyl, cycloheptylcarbamoyl, etc.), lower alkoxycarbonyl (e.g. methoxycarbonyl, ethoxycarbonyl, etc.) and lower alkanoyl (e.g. formyl, etc.); heterocyclic thio such as unsaturated condensed heterocyclic thio containing 1 to 3 nitrogen atom(s) (e.g. benzimidazolylthio, etc.); heterocyclic group, for example, 5- or 6-membered heteromonocyclic group such as triazolyl substituted with amino (e.g. 3-aminotriazolyl, etc.); or a group of the formula:

in which

R⁴ is hydrogen; cyano; or acyl such as carbamoyl, sulfamoyl, lower alkylsulfonyl (e.g. mesyl, etc.), and mono or di(lower)alkylsulfamoyl (e.g. methylsulfamoyl, etc.); and R⁵ is amino; or lower alkoxy (e.g. methoxy, etc.);

R² is hydrogen; acyl such as lower alkylcarbamoyl (e.g. methylcarbamoyl, etc.); lower alkyl (e.g. methyl, ethyl, propyl, isopropyl, butyl, isopentyl, hexyl, etc.); lower alkoxy(lower)alkyl (e.g. methoxyethyl, etc.); di(lower)alkylamino(lower)alkyl (e.g. dimethylaminoethyl, etc.); (C₃–C₇)-cycloalkyl (e.g. cyclohexyl cyclopropyl, cyclopentyl, etc.); lower alkenyl (e.g. allyl etc.); or mono or di or trihalo(lower)alkyl (e.g. trifluoroethyl etc.);

R³ is hydrogen; or lower alkyl (e.g. methyl, etc.); or R² and R³ are linked together to form lower alkylene (e.g. ethylene, etc.);

Y is

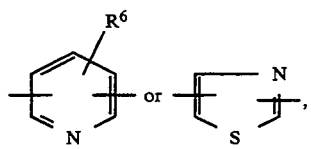

in which R⁶ is hydrogen or halogen (e.g. chloro, etc.);

A is bond; or lower alkylene (e.g. methylene, ethylene, etc.); and

W is NH; or

R²-W is pyperidino or morpholino; provided that when R¹ is amino which may have suitable substituent(s) and A is bond; or R¹ is lower alkylthioureido and A is lower alkylene, then Y is

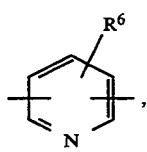

in which R⁶ is as defined above.

The processes for preparing the object compounds (I) of the present invention are explained in detail in the following.

Process 1

The object compound (I) or a salt thereof can be prepared by reacting the compound (II) or a salt thereof with the compound (III) or a salt thereof.

This reaction is usually conducted in a conventional solvent which does not adversely influence the reaction such as methyl acetate, dichloromethane, chloroform, carbon tetrachloride, tetrahydrofuran, acetone, N,N-dimethylformamide, N,N-dimethylacetamide, dioxane, water, alcohol [e.g. methanol, ethanol, etc.] acetic acid, formic acid, etc. or a mixture thereof.

The reaction temperature is not critical and the reaction is usually conducted under cooling to heating.

Process 2

The object compound (I-2) or a salt thereof can be prepared by subjecting the compound (I-1) or a salt thereof to elimination reaction of the amino protective group.

Suitable method for this elimination reaction may include conventional one such as hydrolysis, reduction, or the like. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), ammonia, or the like, and an organic base such as tri(lower)alkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,2]octane, 1,5-diazabicyclo[5,4,0]-undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

Process 3

The object compound (I-3) or a salt thereof can be prepared by reacting the compound (I-2) or a salt thereof with an acylating agent.

The compound (I-2) may be used in the form of its conventional reactive derivative at the amino group.

The acylating agent can be represented by the compound of the formula:

$$R^{17}-OH \qquad (XXI)$$

in which R¹⁷ is acyl as defined above and its conventional reactive derivative at the hydroxy group.

The suitable example may be an acid halide (e.g. acid chloride, etc.), an acid anhydride, an activated amide, an activated ester, and the like.

In this reaction, when the compound (XXI) is used in a free acid form or its salt form, the reaction is preferably carried out in the presence of a conventional condensing agent such as 1-(3-dimethylaminopropyl)-3ethylcarbodiimide, and the like.

In case the acyl group to be introduced is a carbamoyl type acyl, the acylating agent is usually used in the form of cyanate or isocyanate.

The reaction is usually carried out in a conventional solvent such as water, alcohol [e.g. methanol, ethanol, etc.] acetone, dioxane, acetonitrile, chloroform, dichloromethane, ethylene chloride, tetrahydrofuran, ethyl acetate, N,N-dimethylformamide, N,N-dimethylacetamide, pyridine, acetic acid or any other organic solvent which does not adversely influence the reaction. These conventional solvents may also be used in a mixture with water.

The reaction temperature is not critical, and the reaction is usually carried out under cooling to warming.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like.

This present reaction includes, within its scope, the case that when $R^2$ is hydrogen, it is also acylated during the reaction or at the post-treating step of the present process.

Process 4

The object compound (I-4) or a salt thereof can be prepared by reacting the compound (I-2) or a salt thereof with the compound (IV).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

The object compound (I-4) can be used as a starting compound of Process 5 or Process 7 mentioned hereinbelow with or without isolation.

Process 5

The object compound (I-5) or a salt thereof can be prepared by reacting the compound (I-4) or a salt thereof with the compound (V).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

In case that the compound (V) is liquid, it can be also used as a solvent.

The reaction temperature is not critical, and the reaction is usually carried out at ambient temperature or under warming or heating.

Process 6

The object compound (I-6) or a salt thereof can be prepared by reacting the compound (I-2) or a salt thereof with the compound (VI).

The reaction is usually carried out in a conventional solvent such as water, alcohol [e.g. methanol, ethanol, etc.], acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction.

The reaction temperature is not critical, and the reaction is usually carried out under cooling to warming.

The reaction may also be carried out in the presence of an inorganic or organic base such as an alkali metal bicarbonate, tri(lower)alkylamine (e.g. triethylamine, etc.), pyridine, N-(lower)alkylmorphorine, N,N-di(lower)alkylbenzylamine, or the like.

Process 7

The object compound (I-8) or a salt thereof can be prepared by reacting the compound (I-7) or a salt thereof with the compound (VII).

This reaction is usually carried out in a conventional solvent which does not adversely influence the reaction such as alcohol [e.g. methanol, ethanol, propanol, etc.], tetrahydrofuran, dioxane, acetonitrile, dimethyl sulfoxide, N,N-dimethylformamide or a mixture thereof.

The reaction temperature is not critical, and the reaction is usually carried out at ambient temperature or under warming or heating.

Process 8

The object compound (I-9) or a salt thereof can be prepared by subjecting the compound (VIII) or a salt thereof to ring closure.

This reaction is usually carried out in the presence of ammonium hydride.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating, preferably under heating.

Process 9

The object compound (I-9) or a salt thereof can be prepared by reacting the compound (IX) or a salt thereof with the compound (X) or a salt thereof.

This reaction can be carried out in substantially the same manner as Process 1, and therefore the reaction mode and reaction conditions [e.g. solvent, reaction temperature, etc.] of this reaction are to be referred to those as explained in Process 1.

Process 10

The object compound (I-11) or a salt thereof can be prepared by subjecting the compound (I-10) or a salt thereof to hydrolysis reaction.

This reaction is usually carried out in a conventional manner for transforming nitrile to amide.

This reaction is usually carried out in a conventional solvent which does not adversely influence the reaction such as water, alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 11

The object compound (I-12) or a salt thereof can be prepared by reacting the compound (I-2) or a salt thereof with the compound (XI).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 12

The object compound (I-14) or a salt thereof can be prepared by reacting the compound (I-13) or a salt thereof with the compound (XII).

This reaction is usually carried out in the presence of dry hydrogen chloride gas.

This reaction is usually carried out in a conventional solvent such as alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out under cooling to heating.

The object compound (I-14) can be used as a starting compound of Process 16 mentioned hereinbelow with or without isolation.

Process 13

The object compound (I-15) or a salt thereof can be prepared by reacting the compound (I-14) or a salt thereof with the compound (XIII).

This reaction is usually carried out in a conventional solvent which does not adversely influence the reaction such as alcohol [e.g. methanol, ethanol, propanol, 2-methoxyethanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 14

The object compound (I-16) or a salt thereof can be prepared by reacting the compound (XIV) or a salt thereof with the compound (XV) or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 15

The object compound (I-17) or a salt thereof can be prepared by reacting the compound (XVI) or a salt thereof with the compound (XVII) or a salt thereof.

This reaction can be carried out in substantially the same manner as Process 5, and therefore the reaction mode and reaction conditions [e.g. solvent, reaction temperature, etc.] of this reaction are to be referred to those as explained in Process 5.

Process 16

The object compound (I-18) or a salt thereof can be prepared by subjecting the compound (I-14) or a salt thereof to hydrolysis.

This reaction is usually carried out in a conventional solvent such as a mixture of water and alcohol [e.g. methanol, etc.] or any other solvent which does not adversely influence the reaction.

The reaction temperature is not critical, and the reaction is usually carried out under cooling to heating.

Process 17

The object compound (I-19) or a salt thereof can be prepared by subjecting the compound (I-18) or a salt thereof to amidation.

This reaction is usually carried out in the presence of ammonia.

This reaction is usually carried out in a conventional solvent such as alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out under cooling to heating.

Process 18

The object compound (I-20) or a salt thereof can be prepared by reacting the compound (I-18) or a salt thereof with hydrazine.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 19

The object compound (I-21) or a salt thereof can be prepared by reacting the compound (I-20) or a salt thereof with S-(lower alkyl)isothiourea or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 20

The object compound (I-22) or a salt thereof can be prepared by subjecting the compound (I-21) or a salt thereof to ring closure.

This reaction is usually carried out in the presence of ammonium hydroxide.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 21

The object compound (I-24) or a salt thereof can be prepared by subjecting the compound (I-23) or a salt thereof to elimination reaction of the hydroxy-protective group.

This reaction can be carried out in substantially the same manner as Process 2, and therefore the reaction mode and reaction conditions [e.g. solvent, reaction temperature, etc.] of this reaction are to be referred to those as explained in Process 2.

Process 22

The object compound (I-26) or a salt thereof can be prepared by reacting the compound (I-25) or a salt thereof with an acylating agent.

This reaction can be carried out in substantially the same manner as Process 3, and therefore the reaction mode and reaction conditions [e.g. solvent, reaction temperature, etc.] of this reaction are to be referred to those as explained in Process 3.

This present reaction includes, within its scope, the case that when $R^1$ is amino, it is also acylated during the reaction or at the post-treating step of the present process.

Process 23

The object compound (I-27) or a salt thereof can be prepared by subjecting the compound (I-19) or a salt thereof to dehydration reaction.

The dehydrating agent to be used in this dehydration reaction may include phosphoryl chloride, thionyl chloride, phosphorus pentoxide, phosphorus pentachloride, phosphorus pentabromide and the like.

This present reaction is usually carried out in a solvent such as dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out at ambient temperature, under warming or heating.

Process 24

The object compound (I-29) or a salt thereof can be prepared by subjecting the compound (I-28) or a salt thereof to reduction.

The reduction may include, for example, reduction with an alkali metal borohydride (e.g. sodium borohydride, etc.), and the like.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out under cooling to heating.

Process 25

The object compound (I-31) or a salt thereof can be prepared by subjecting the compound (I-30) or a salt thereof to halogenation.

This reaction is usually carried out in a conventional manner for transforming hydroxy to halogen, preferably by using thionyl chloride.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 26

The object compound (I-32) or a salt thereof can be prepared by reacting the compound (I-31) or a salt thereof with the compound (XVIII).

The reaction is usually carried out in a conventional solvent such as water, alcohol [e.g. methanol, ethanol, etc.], acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction.

The reaction temperature is not critical, and the reaction is usually carried out under cooling to warming.

The reaction may also be carried out in the presence of an inorganic or organic base such as an alkali metal carbonate (e.g. potassium carbonate, etc.), tri(lower)alkylamine (e.g. triethylamine, etc.), pyridine, N-(lower)alkylmorphorine, N,N-di(lower)alkylbenzylamine, or the like.

Process 27

The object compound (I-33) or a salt thereof can be prepared by subjecting the compound (I-29) or a salt thereof to oxidation.

This reaction is usually carried out in a conventional manner for transforming hydroxymethyl to formyl, for example, by using pyridinium dichromate.

This reaction is usually carried out in a conventional solvent which does not adversely influence the reaction such as alcohol [e.g. methanol, ethanol, propanol, etc.], tetrahydrofuran, dioxane, acetonitrile, dimethyl sulfoxide, N,N-dimethylformamide or a mixture thereof.

The reaction temperature is not critical, and the reaction is usually carried out under cooling to heating, preferably under cooling.

Process 28

The object compound (I-19) or a salt thereof can be prepared by subjecting the compound (I-13) or a salt thereof to hydrolysis reaction.

This reaction can be carried out in substantially the same manner as Process 10, and therefore the reaction mode and reaction conditions [e.g. solvent, reaction temperature, etc.] of this reaction are to be referred to those as explained in Process 10.

Process 29

The object compound (I-34) or a salt thereof can be prepared by reacting the compound (I-31) or a salt thereof with the compound (XIX).

This reaction is usually carried out in a conventional solvent which does not adversely influence the reaction such as alcohol [e.g. methanol, ethanol, propanol, etc.], tetrahydrofuran, dioxane, acetonitrile, dimethyl sulfoxide, N,N-dimethylformamide or a mixture thereof.

The reaction temperature is not critical, and the reaction is usually carried out at ambient temperature or under warming or heating.

Process 30

The object compound (I-2) or a salt thereof can be prepared by reacting the compound (I-34) or a salt thereof with hydrazine hydrate.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

The object compound (I-2) can be used as a starting compound of Process 3 mentioned above with or without isolation.

Process 31

The object compound (I-36) or a salt thereof can be prepared by subjecting the compound (I-35) or a salt thereof to hydrogenation.

The method applicable for this reaction may include, for example, conventional catalytic reduction in the presence of a conventional metallic catalyst (e.g. palladium on carbon, etc.).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 32

The object compound (I-38) or a salt thereof can be prepared by subjecting the compound (I-37) or a salt thereof to elimination reaction of the amino protective group.

This reaction can be carried out in substantially the same manner as Process 2, and therefore the reaction mode and reaction conditions [e.g. solvent, reaction temperature, etc.] of this reaction are to be referred to those as explained in Process 2.

Among the starting compounds, some of them are new and such compounds can be prepared by the methods of Preparation mentioned below and by any process known in the art for preparing structurally analogous compounds thereto.

The compounds obtained by the above Processes 1 to 32 can be isolated and purified by a conventional method such as pulverization, recrystallization, column chromatography, reprecipitation or the like.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

The new thiazole derivatives (I) and pharmaceutically acceptable salts thereof possess antiulcer activity and $H_2$-receptor antagonism, and are useful for a therapeutic treatment of gastritis, ulcer (e.g. gastric ulcer, duodenal ulcer, anastomotic ulcer, etc.), Zollinger-Ellison Syndrome, reflux esophagitis, upper gastrointestinal bleeding, and the like.

And further, the compound (I) and pharmaceutically acceptable salts thereof of the present invention possess high antimicrobial activity against pathogenic microorganisms such as Campylobacter pyloridis, Helicobacter pyloridis, and the like, which are a gram-negative bacillus that has recently been found beneath the mucus gel of the human stomach.

For therapeutic purpose, the compound (I) and a pharmaceutically acceptable salt thereof of the present invention can be used in a form of pharmaceutical preparation containing one of said compounds, as an active ingredient, inadmixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average singel dose of about 0.1 mg, 1 mg, 10 mg, 50 mg, 100 mg, 250 mg, 500 mg and 1000 mg of the compound (I) may be effective for treating ulcer. In general, amounts between 0.1 mg/body and about 1,000 mg/body may be administered per day.

In order to illustrate the usefulness of the object compound (I), the pharmacological test data of some representative compounds of the compound (I) are shown in the following.

Test compounds
(a) 4-(6-Acetylaminomethylpyridin-2-yl)-2-(diaminomethyleneamino)thiazole dihydrochloride
(b) 2-(Diaminomethyleneamino)-4-(6-ureidomethyl-pyridin-2-yl)thiazole dihydrochloride
(c) 2-(Diaminomethyleneamino)-4-(2-ureidomethyl-thiazol-4-yl)thiazole
(d) 4-[2-(Diaminomethyleneamino)thiazol-4-yl]thiazole-2-carboxylic acid ethyl ester hydrobromide
(e) 4-(6-Acetylaminomethylpyridin-2-yl)-2-[(amino)-(n-butylamino)methyleneamino]thiazole Test A (Gastric secretion in Heidenhain pouch dogs):
Test Method
Beagle dogs, weighing about 8–13 kg, were used for the study on gastric secretion. The animals were surgically provided with a vagally denervated Heidenhain pouch. One month or more later, the dogs were fasted overnight. Gastric secretion was stimulated by an intravenous infusion of tetragastrin (10 μg/kg/hr). Gastric samples were collected at 15 min intervals. After its volume was almost constant, test compound (3.2 mg/kg) suspended in 0.1% methyl cellulose solution was administered orally. Acid concentration was determined by titrating an aliquot to pH 7.0 with 0.1N sodium hydroxide solution using automatic titration (Hiranuma RAT-11 Type). Total acid output was calculated by multiplying total volume of gastric samples by acid concentration, and percentage change of total acid output was calculated by comparing with predosing value of test compound.

| Test Result | |
|---|---|
| Test Compound | Inhibition (%) |
| (a) | 95 |

Test B (Inhibition of stress ulcer):
Test Method
Five male Sprague-Dawley rats, aged 7 weeks and weighing about 200 g were used per group for the study on stress ulcer after the fast for 24 hours. Each animal was immobilized in a restrain cage and immersed to a level of the xiphoid in a water bath kept 22° C. Each of the test compounds (32 mg/kg) suspended in 0.1% methylcellulose solution was administered orally just before the immobilization. Seven hours later, the animals were sacrificed and their stomachs were removed. The stomach was then fixed with 2% formalin. The area of ulcers was measured for each animal, and percentage of inhibition was calculated by comparing the mean area of ulcers ($mm^2$) in the test animals with that in the control animals.

| Test Result | |
|---|---|
| Test Compound | Inhibition (%) |
| (d) | 93.9 |

Test C (Gastric secretion from lumen perfused stomach in anesthetized rats):
Test Method
Male Sprague-Dawley rats weighing about 250 g were used. Rats were deprived of food but allowed free access to water for 24 hours. The animals were anesthetized with 1.25 g/kg urethane intraperitoneally. The abdomen was opened and the gastric lumen was perfured with saline throughout the experiment. The perfusate was titrated by an antotitrator with 25 mM sodium hydroxide as a titrant. Gastric secretion was stimulated by intravenous infusion with histamine (3 mg/kg/hr). After reaching plateau, test compound (1 mg/kg) was given intravenously. Drug effect was expressed as maximal inhibition by acid output.

| Test Compound | Test Rsult Inhibition (%) |
|---|---|
| (b) | 98 |
| (c) | 97 |

Test D (Anti-microbial activity):
Test Method

In vitro antimicrobial activity was determined by the agar dilution method. Test strain was precultured in Brucella broth containing 5% horse serum at 37° C. for 3 days $10^4$ cfu were inoculated with a multipoint replicater onto Brucella agar plus 5% lysed horse blood plate containing serial 2-fold dilutions of each drug at 37° C. for 3 days. Incubation was carried out in an atmosphere of 10% $CO_2$. MIC was read after incubation as the lowest drug concentration that inhibited macroscopic colonial growth.

| Test strain | Test Result Mic (μg/ml) Test Compound |
|---|---|
| | (a) |
| Campylobacter pyloridis 8008 | 3.13 |
| | (e) |
| Helicobacter pyloridis 8008 | 0.78 |

Test E (Inhibition of HCl-aspirin ulcer):
Test Method

Seven male Sprague-Dawley rats, aged 6 weeks and weighing about 200 g were used per group for the study on HCl-aspirin ulcer after the fast for 24 hours. Each of the test compounds (32 mg/kg) suspended in 0.1% methylcellulose solution was administered orally 30 minutes before aspirin administration. Aspirin, suspended in 0.1% methylcellulose solution containing 0.2N HCl, was administered orally at a dose of 200 mg/kg/10 ml. One hour later, the animals were sacrificed and their stomachs were removed. The stomach was then fixed with 2% formalin. The length of ulcers was measured for each animal, and percentage of inhibition was calculated by comparing the mean length of ulcers (mm) in the test animals with that in the control animals.

| Test Compound | Test Result Inhibition (%) |
|---|---|
| (e) | 98.1 |

The following Preparations and Examples are given for the purpose of illustrating the present invention in more detail.

Preparation 1

Phosphorus oxychloride (7.09 ml) was added dropwise to a solution of 6-hydroxymethyl-2-pyridinecarboxamide (3.60 g) in N,N-dimethylformamide (36 ml) at 0° to 5° C. with stirring and the mixture was stirred for further 6 hours at the same temperature.

The solvent was evaporated in vacuo and the residue was dissolved in water (100 ml). The solution was made basic with aqueous potassium carbonate and extracted with ethyl acetate. The extract was dried over magnesium sulfate and evaporated in vacuo to give 6-chloromethyl-2-pyridinecarbonitrile (3.02 g).

mp: 61°–63° C. IR (Nujol): 2240 cm$^{-1}$ NMR (DMSO-d$_6$, δ): 4.87 (2H, s), 7.90 (1H, dd, J=1.2 Hz and 7.7 Hz), 8.03 (1H, dd, J=1.2 Hz and 7.7 Hz), 8.14 (1H, t, J=7.7 Hz)

Preparation 2

A mixture of 6-chloromethyl-2-pyridinecarbonitrile (2.75 g) and potassium phthalimide (3.35 g) in N,N-dimethylformamide (27.5 ml) was stirred at ambient temperature for 4 hours. After the solvent was evaporated in vacuo, water (50 ml) was added to the residue and the resulting precipitate was collected by filtration to give 6-phthalimidomethyl-2-pyridinecarbonitrile (4.60 g).

mp: 200°–201° C. IR (Nujol): 2250, 1775, 1715 cm$^{-1}$ NMR (DMSO-d$_6$, δ): 4.99 (2H, s), 7.81 (1H, dd, J=1.0 Hz and 7.7 Hz), 7.85–7.98 (5H, m), 8.06 (1H, t, J=7.7 Hz)

Preparation 3

A solution of hydrazine hydrate (0.77 g) in methanol (5 ml) was added dropwise to a suspension of 6-phthalimidomethyl-2-pyridinecarbonitrile (3.74 g) in a mixture of methanol (10 ml) and tetrahydrofuran (15 ml) at ambient temperature with stirring. After the mixture was stirred for two hours, diluted hydrochloric acid (prepared by concentrated hydrochloric acid (1.38 ml) and water (6.91 ml)) was dropped to the mixture. After stirring for three hours, the solvent was evaporated in vacuo. The residue was mixed with water (20 ml) and an insoluble material was filtered off. The filtrate was evaporated in vacuo to give 6-aminomethyl-2-pyridinecarbonitrile hydrochloride (2.40 g).

mp: >300° C. IR (Nujol): 2240 cm$^{-1}$ NMR (DMSO-d$_6$, δ): 4.27 (2H, s), 7.94 (1H, dd, J=1.2 Hz and 7.7 Hz), 8.08 (1H, dd, J=1.2 Hz and 7.7 Hz), 8.16 (1H, t, J=7.7 Hz), 8.83 (3H, br s)

Preparation 4

Acetic anhydride (1.29 ml) was added dropwise to a mixture of 6-aminomethyl-2-pyridinecarbonitrile hydrochloride (2.10 g) in pyridine (21 ml). The solution was stirred for four hours at ambient temperature and evaporated in vacuo. The residue was mixed with aqueous potassium carbonate and extracted with ethyl acetate. The extract was dried over magnesium sulfate and evaporated in vacuo to give 6-(acetylaminomethyl)-2-pyridinecarbonitrile (1.72 g).

mp: 91°–92° C. IR (Nujol): 3260, 2230, 1650 cm$^{-1}$ NMR (DMSO-d$_6$, δ): 1.92 (3H, s), 4.39 (2H, d, J=6 Hz), 7.62 (1H, dd, J=1 Hz and 7.7 Hz), 7.97 (1H, dd, J=1 Hz and 7.7 Hz), 8.03 (1H, t, J=7.7 Hz), 8.56 (1H, t, J=6 Hz)

Preparation 5

An ethereal solution of methyl magnesium bromide (3 mol/l) (17.6 ml) was added dropwise to a solution of 6-(acetylaminomethyl)-2-pyridinecarbonitrile (3.70 g) in tetrahydrofuran (60 ml) at 5° to 10° C. with stirring. After the mixture was stirred for two hours at the same temperature, cold water (15 ml) was dropped to the mixture under ice-cooling and evaporated in vacuo. The residue was mixed with water and extracted with a mixture of ethyl acetate and tetrahydrofuran. The extract was dried over magnesium sulfate and evaporated in vacuo. The residue was purified by silica gel column chromatography by eluting with a mixture of ethyl acetate and methanol (50:1) to give 2-acetyl-6-(acetylaminomethyl)pyridine (2.70 g).

mp: 88°–89° C. IR (Nujol): 3300, 1690, 1650 cm$^{-1}$ NMR (DMSO-d$_6$, δ): 1.94 (3H, s), 2.64 (3H, s), 4.43 (2H, d, J=6.0 Hz), 7.54 (1H, dd, J=1 Hz and 7.7 Hz), 7.82 (1H, dd, J=1 Hz and 7.7 Hz), 8.00 (1H, t, J=7.7 Hz), 8.53 (1H, t, J=6 Hz)

Preparation 6

A solution of bromine (1.56 g) in acetic acid (5 ml) was added dropwise to a solution of 2-acetyl-6-(acetylaminomethyl)pyridine (1.87 g) and 30 weight % hydrogen bromide-acetic acid solution (4.2 ml) in a mixture of acetic acid (40 ml) and methanol (10 ml) at ambient temperature with stirring. The mixture was warmed to 60° to 70° C. and stirred for two hours. The solvent was evaporated in vacuo and the residue was triturated with diisopropyl ether to give 2-(acetylaminomethyl)-6-bromoacetylpyridine hydrobromide (3.78 g).

IR (Nujol): 1720, 1620 cm$^{-1}$ NMR (CD$_3$OD, δ): 2.10 (3H, s), 3.90 (2H, s), 4.83 (2H, s), 7.77 (1H, br s), 8.13 (2H, t, J=8 Hz) and 8.70 (1H, t, J=8 Hz)

Preparation 7

A mixture of 2-bromo-1-hydroxy-3-oxo-1-butene (9.61 g) and N-[(thiocarbamoyl)methyl]acetamide (7.70 g) in acetone (100 ml) was refluxed for one hour with stirring. The resulting precipitate was collected by filtration and chromatographed on silica gel eluting with a mixture of chloroform and methanol (20:1, V/V) to give 5-acetyl-2-(acetylaminomethyl)thiazole (3.48 g).

mp: 98°–100° C. IR (Nujol): 3310, 1655 cm$^{-1}$ NMR (DMSO-d$_6$, δ): 1.92 (3H, s), 3.55 (3H, s), 4.53 (2H, d, J=6 Hz), 8.50 (1H, s), 8.83 (1H, t, J=6 Hz) MS (m/e): 198, 155

Preparation 8

A solution of bromine (1.61 g) in acetic acid (4 ml) was added dropwise to a mixture of 5-acetyl-2-acetylaminomethylthiazole (2.00 g), 30 (W/W) % hydrobromic acid solution in acetic acid (5 ml) and acetic acid (40 ml) at ambient temperature. After stirring for 24 hours at ambient temperature, the resulting precipitate was collected by filtration and washed with acetic acid to give 2-(acetylaminomethyl)-5-bromoacetylthiazole (3.00 g).

mp: 160°–164° C. IR (Nujol): 3250, 1700, 1655 cm$^{-1}$ NMR (CD$_3$OD, δ): 2.02 (3H, s), 4.59 (2H, s), 4.69 (2H, s), 8.52 (1H, s)

Preparation 9

A suspension of 1-bromo-2,3-butanedione (47 g) and N-[(thiocarbamoyl)methyl]acetamide (30 g) in acetone (600 ml) was refluxed for 3 hours. The resulting precipitate was collected by filtration to afford 4-acetyl-2-(acetylaminomethyl)thiazole (41.8 g).

mp: 185°–186° C. IR (Nujol): 3410, 3350, 1690, 1620 cm$^{-1}$ NMR (DMSO-d$_6$, δ): 1.93 (3H, s), 2.55 (3H, s), 4.54 (2H, d, J=5.8 Hz), 8.44 (1H, s), 8.91 (1H, t, J=5.8 Hz)

Preparation 10

A suspension of 4-acetyl-2-thiazolecarboxylic acid ethyl ester (2.5 g) in 28% aqueous ammonia solution (40 ml) was stirred for 1 hour at room temperature. The resulting precipitate was collected by filtration to afford 4-acetyl-2-thiazolecarboxamide (1.76 g).

NMR (DMSO-d$_6$, δ): 2.63 (3H, s), 8.02 (1H, s), 8.28 (1H, s), 8.74 (1H, s),

Preparation 11

Bromine (9.9 ml) was added dropwise to a mixture of 2-acetyl-6-(acetylaminomethyl)pyridine (37.0 g) in dioxane (740 ml) and 4N-dioxanic hydrogen chloride (48.1 ml) at ambient temperature with stirring. After the mixture was stirred at 50° C. for 3 hours. To the mixture was added a diisopropyl ether (600 ml) and the mixture was stirred under ice-cooling for 30 minutes. The isolated precipitate was collected by filtration. The precipitate was added to water and the mixture was adjusted to pH 8 with 20% aqueous potassium carbonate. The aqueous mixture was extracted with a mixture of ethyl acetate and tetrahydrofuran. The extract was dried over magnesium sulfate and evaporated in vacuo to give 2-(acetylaminomethyl)-6-bromoacetylpyridine (50.3 g) as an oil. IR (Film): 1710, 1650 cm$^{-1}$ NMR (CDCl$_3$δ): 2.11 (3H, s), 4.63 (2H, d, J=5.3 Hz), 4.80 (2H, s), 7.43–7.59 (1H, m), 7.78–8.08 (2H, m)

Preparation 12

Propionic anhydride (76.3 ml) was added dropwise to a mixture of 6-aminomethyl-2-pyridinecarbonitrile hydrochloride (84.1 g) in water (800 ml) under keeping pH 7~8 with 40% aqueous potassium carbonate at ambient temperature and the mixture was stirred at the same temperature for 30 minutes. The aqueous mixture was extracted with ethyl acetate. The extract was dried over magnesium sulfate and evaporated to give 6-(propionylaminomethyl)-2-pyridinecarbonitrile (54.2 g).

IR (Film): 3280, 2240, 1640, 1590, 1535 cm$^{-1}$ NMR (DMSO-d$_6$, δ): 1.05 (3H, t, J=7.6 Hz), 2.21 (2H, q, J=7.6 Hz), 4.40 (2H, d, J=5.8 Hz), 7.61 (1H, dd, J=1.0 Hz, 7.8 Hz), 7.91 (1H, dd, J=1.0 Hz, 7.8 Hz), 8.03 (1H, t, J=7.8 Hz), 8.50 (1H, t, J=5.8 Hz)

Preparation 13

The following compound was obtained according to a similar manner to that of Preparation 5.

2-Acetyl-6-(propionylaminomethyl)pyridine mp: 79° C. IR (Nujol): 3280, 1700, 1640, 1590, 1550 cm$^{-1}$ NMR (DMSO-d$_6$, δ): 1.06 (3H, t, J=7.6 Hz), 2.22 (2H, q, J=7.6 Hz), 2.64 (3H, s), 4.44 (2H, d, J=6.0 Hz), 7.52 (1H, d, J=7.6 Hz), 7.82 (1H, d, J=7.6 Hz), 7.96 (1H, t, J=7.6 Hz), 8.45 (1H, t, J=6.0 Hz)

Preparation 14

The following compound was obtained according to a similar manner to that of Preparation 11.

2-Bromoacetyl-6-(propionylaminomethyl)pyridine mp: 81°–83° C. IR (Nujol): 3390, 1720, 1645 cm$^{-1}$ NMR (DMSO-d$_6$, δ): 1.06 (3H, t, J=7.6 Hz), 2.22 (2H, q, J=7.6 Hz), 4.44 (2H, d, J=5.9 Hz), 5.05 (2H, s), 7.57 (1H, d, J=7.6 Hz), 7.89 (1H, d, J=7.6 Hz), 8.01 (1H, t, J=7.6 Hz),
8.45 (1H, t, J=5.9 Hz)

Preparation 15

A suspension of 2-(diaminomethyleneamino)-4-bromoacetylthiazole (10.0 g) and N-[(thiocarbamoyl)methyl]acetamide (5.0 g) in ethanol (100 ml) was stirred at room temperature for 10 hours. The resulting precipitate was collected by filtration to afford 4-[(2- acetylamino-1-iminoethyl)thioacetyl]-2-(diaminomethyleneamino)thiazole hydrobromide (11.4 g).

IR (Nujol): 3120, 1680, 1620 cm$^{-1}$ NMR (DMSO-d$_6$, δ): 1.88 (3H, s), 3.37 (1H, d, J=12.0 Hz), 3.64 (1H, d, J=12.0 Hz), 4.03 (1H, dd, J=6.0 and 16.7 Hz), 4.14 (1H, dd, J=6.0 and 16.7 Hz), 6.90 (1H, s), 7.21 (1H, s), 8.19 (4H, s), 8.55 (1H, t, J=6.0 Hz), 11.97 (1H, br)

Preparation 16

A mixture of 2-chloromethyl-6-cyanopyridine (4.5 g), dimethylamine hydrochloride (7.2 g) and triethylamine (12.3 ml) in dichloromethane (70 ml) was stirred for 2.5 hours at ambient temperature and then the solvent was removed by concentration in vacuo. To the residue was added a mixture of ethyl acetate and tetrahydrofuran, washed with brine and dried over magnesium sulfate. Evaporation of a solvent gave a residue, which was purified by column chromatography on silica gel eluting with a mixture of chloroform and methanol (19:1, V/V). The eluted fractions containing the desired product were collected and evaporated in vacuo to give 2-cyano-6-(dimethylaminomethyl)pyridine (2.49 g) as an oil.

IR (Film): 2240, 1585 cm$^{-1}$ NMR (DMSO-d$_6$, δ): 2.20 (6H, s), 3.57 (2H, s), 7.77 (1H, dd, J=1.2 Hz and 7.7 Hz), 7.93 (1H, dd, J=1.2 Hz and 7.7 Hz), 8.04 (1H, t, J=7.7 Hz)

Preparation 17

The following compound was obtained according to a similar manner to that of Preparation 5.

2-Acetyl-6-(dimethylaminomethyl)pyridine

IR (Film): 3380, 1690, 1585 cm$^{-1}$ NMR (DMSO-d$_6$, δ): 2.23 (6H, s), 2.62 (3H, s), 3.62 (2H, s), 7.68 (1H, dd, J=1.1 Hz and 7.6 Hz), 7.84 (1H, dd, J=1.1. Hz and 7.6 Hz), 7.97 (1H, t, J=7.6 Hz)

Preparation 18

A mixture of 6-hydroxymethyl-2-pyridinecarboxamide (100 g) and manganese dioxide (500 g) in chloroform (2 l) was heated under reflux for 48 hours. Manganese dioxide was removed by filtration and the filtrate was evaporated in vacuo to give 6-formyl-2-pyridinecarboxamide (60.46 g).

mp: 180°-181° C. IR (Nujol): 3420, 3180, 1700 cm$^{-1}$ NMR (DMSO-d$_6$, δ): 7.90 (1H, s), 8.10 (1H, dd, J=1.6 Hz and 7.5 Hz), 8.24 (1H, t, J=7.5 Hz), 8.24-8.39 (1H, m), 8.32 (1H, dd, J=1.6 Hz and 7.5 Hz), 10.04 (1H, s)

Preparation 19

An ethereal solution of methyl magnesium bromide (3 mol/l) (546 ml) was added dropwise to a solution of 6-formyl-2-pyridinecarboxamide (61.5 g) in tetrahydrofuran (900 ml) at 0°-13° C. with stirring. After the mixture was stirred at the same temperature for 2 hours and cold water was dropped to the reaction mixture under ice-cooling. To the mixture was added ethyl acetate and adjusted to pH 7 with 6N-hydrochloric acid. The separated organic layer was washed with brine, dried over magnesium sulfate and evaporated in vacuo to give 6-(1-hydroxyethyl)-2-pyridinecarboxamide (63.2 g) as an oil.

IR (Film): 3450-3200 (br), 1700-1650 (br) cm$^-$NMR (DMSO-d$_6$, δ): 1.42 (3H, d, J=6.5 Hz), 4.73-4.86 (1H, m), 5.46 (1H, d, J=5.3 Hz), 7.63-8.34 (5H, m)

Preparation 20

The following compound was obtained according to a similar manner to that of Preparation 18.

6-Acetyl-2-pyridinecarboxamide mp: 143°-145° C. IR (Nujol): 3180, 1680, 1590 cm$^{-1}$ NMR (DMSO-d$_6$, δ): 2.78 (3H, s), 7.88 (1H, s), 8.10 (1H, dd, J=1.7 Hz and 7.5 Hz), 8.19 (1H, t, J=7.5 Hz), 8.28 (1H, dd, J=1.7 Hz and 7.5 Hz), 8.32 (1H, s)

Preparation 21

The following compound was obtained according to a similar manner to that of Preparation 11.

6-Bromoacetyl-2-pyridinecarboxamide mp: 168°-170° C. IR (Nujol): 3440, 1670, 1640, 1580 cm$^{-1}$ NMR (DMSO-d$_6$, δ): 5.35 (2H, s), 7.85 (1H, s), 8.15 (1H, dd, J=2.0 Hz and 7.5 Hz), 8.21 (1H, t, J=7.5 Hz), 8.30 (1H, dd, J=2.0 Hz and 7.5 Hz), 8.50 (1H, s)

Preparation 22

A mixture of 6-hydroxymethyl-2-pyridinecarboxamide (80 g) and acetic anhydride (198.8 ml) in tetrahydrofuran (800 ml) was heated under reflux for 24 hours. The reaction mixture was added to a mixture of ethyl acetate and water and the mixture was adjusted to pH 8 with potassium carbonate. The separated organic layer was washed with brine, dried over magnesium sulfate and evaporated to give 6-acetoxymethyl-2-pyridinecarboxamide (93.34 g).

mp: 92°-93° C. IR (Nujol): 3380, 3180, 1730, 1680, 1590 cm$^{-1}$ NMR (DMSO-d$_6$, δ): 2.16 (3H, s), 5.22 (2H, s), 7.61 (1H, dd, J=2.6 Hz and 6.3 Hz), 7.72 (1H, s), 7.94-8.07 (3H, m)

Preparation 23

Phosphorus oxychloride (86.9 ml) was dropwise added to a mixture of 6-acetoxymethyl-2-pyridinecarboxamide (93.0 g) and N,N-dimethylformamide (74.2 ml) in ethyl acetate (930 ml) under ice-cooling with stirring and the mixture was stirred at ambient temperature for 4 hours. The reaction mixture was added to a water and adjusted to pH 8 with potassium carbonate. The separated organic layer was washed with brine, dried over magnesium sulfate and evaporated to give 6-acetoxymethyl-2-cyanopyridine (84.0 g) as an oil.

IR (Film): 2230, 1735, 1670, 1585 cm$^{-1}$ NMR (DMSO-d$_6$, δ): 2.15 (3H, s), 5.20 (2H, s), 7.77 (1H, dd, J=0.7 Hz and 7.8 Hz), 7.99 (1H, dd, J=0.7 Hz and 7.8 Hz), 8.10 (1H, t, J=7.8 Hz)

Preparation 24

The following compound was obtained according to a similar manner to that of Preparation 5.

2-Acetyl-6-hydroxymethylpyridine

IR (Film): 1690, 1590 cm$^{-1}$ NMR (CDCl$_3$, δ): 2.74 (3H, s), 3.77 (1H, t, J=4.8 Hz), 4.84 (2H, d, J=4.8 Hz), 7.45 (1H, d, J=7.6 Hz), 7.85 (1H, t, J=7.6 Hz), 7.96 (1H, d, J=7.6 Hz)

Preparation 25

Phosphorus oxychloride (7.8 ml) was dropwise added to a mixture of 2-acetyl-6-hydroxymethylpyridine (10.0 g) and N,N-dimethylformamide (15.4 ml) in ethyl acetate (100 ml) under ice-cooling with stirring and the mixture was stirred at the same temperature for 3 hours. The reaction mixture was added to water and adjusted to pH 7.5 with potassium carbonate. The separated organic layer was washed with brine, dried over magnesium sulfate and evaporated to give 2-acetyl-6-chloromethylpyridine (10.85 g) as an oil.

IR (Film): 1700, 1670, 1585 cm$^{-1}$ NMR (CDCl$_3$, δ): 2.72 (3H, s), 4.73 (2H, s), 7.68 (1H, d, J=7.7 Hz), 7.87 (1H, t, J=7.7 Hz), 7.98 (1H, d, J=7.7 Hz)

Preparation 26

A mixture of 2-acetyl-6-chloromethylpyridine (10.8 g) and potassium cyanide (4.1 g) in N,N-dimethylformamide (108 ml) was stirred under ice-cooling for 1 hour and then the mixture was stirred at ambient temperature for 18 hours.

To the mixture was added to water and extracted with ethyl acetate. The extract layer was washed with brine and dried over magnesium sulfate. Evaporation of a solvent gave a residue, which was purified by column chromatography on silica gel, eluting with a chloroform. The eluted fractions containing the desired product were collected and evaporated in vacuo to give 2-acetyl-6-cyanomethylpyridine (3.0 g).

mp: 57° C. IR (Nujol): 2240, 1690, 1580 cm$^{-1}$ NMR (DMSO-d$_6$, δ): 2.66 (3H, s), 4.36 (2H, s), 7.70 (1H, d, J=7.7 Hz), 7.92 (1H, d, J=7.7 Hz), 8.05 (1H, t, J=7.7 Hz)

Preparation 27

Phosphorus oxychloride (8.5 ml) was added slowly to a solution of 4-acetyl-2-thiazolecarboxamide (10.0 g) in N,N-dimethylformamide (500 ml) at 0°–5° C. with cooling on an ice-water bath. The mixture was stirred at 0°–5° C. with cooling on an ice-water bath for 4 hours and then was poured into ice water (400 ml). The solution was extracted with ethyl acetate (750 ml×2). The extract was dried with magnesium sulfate. The solvent was removed under reduced pressure and the residue was crystallized from water to afford 4-acetyl-2-cyanothiazole (6.7 g).

mp: 93° C. IR (Nujol): 3050, 2230, 1680 cm$^{-1}$ NMR (DMSO-d$_6$, δ): 2.62 (3H, s), 8.92 (1H, s)

Preparation 28

The following compound was obtained according to a similar manner to that of Example 17.

4-(6-Acetylaminomethylpyridin-2-yl)-2-aminothiazole mp: 179°–180° C. IR (Nujol): 3380, 3260, 3110, 1655, 1620 cm$^{-1}$ NMR (DMSO-d$_6$, δ): 1.93 (3H, s), 4.36 (2H, d, J=5.9 Hz), 7.11 (2H, s), 7.13 (1H, d, J=7.0 Hz), 7.26 (1H, s), 7.68 (1H, d, J=7.0 Hz), 7.76 (1H, t, J=7.0 Hz), 8.45 (1H, t, J=5.9 Hz)

Preparation 29

The following compound was obtained according to a similar manner to that of Example 2.

4-(6-Acetylaminomethylpyridin-2-yl)-2-aminothiazole hydrochloride mp: 258° C. IR (Nujol): 3370, 3280, 3220, 1655, 1615, 1590 cm$^{-1}$ NMR (DMSO-d$_6$, δ): 2.01 (3H, s), 4.47 (2H, d, J=5.6 Hz), 7.33–7.42 (1H, m), 7.68 (1H, s), 7.90–7.99 (2H, m), 8.63 (1H, t, J=5.6 Hz) Anal. Calcd. for C$_{11}$H$_{12}$N$_4$OS.HCl.H$_2$O: C 43.64, H 4.99, N 18.50, Cl 11.71, H$_2$O 5.95 Found: C 43.45, H 4.86, N 18.37, Cl 11.78, H$_2$O 5.96

Preparation 30

Benzoyl chloride (15.7 ml) was dropped to a refluxing solution of ammonium thiocyanate (11.3 g) in acetone (640 ml) and the mixture was refluxed for 20 minutes. 4-(6-Acetylaminomethylpyridin-2-yl)-2-aminothiazole (32.0 g) was added portionwise to the refluxing mixture. After the mixture was refluxed for 3 hours, the solvent was evaporated in vacuo and the residue was mixed with ethyl acetate, tetrahydrofuran and water. The mixture was adjusted to pH 9.5 with 20% aqueous potassium carbonate and resulting precipitate was collected by filtration to give 4-(6-acetylaminomethylpyridin-2-yl)-2-(3-benzoylthioureido)thiazole (15.11 g).

mp: 222° C. (dec.) IR (Nujol): 3300, 1670, 1640 cm$^{-1}$ NMR (DMSO-d$_6$, δ): 1.95 (3H, s), 4.42 (2H, d, J=5.9 Hz), 7.19–7.33 (1H, m), 7.49–7.80 (3H, m), 8.82–8.06 (5H, m), 8.50 (1H, t, J=5.9 Hz), 12.16 (1H, s), 14.29 (1H, s)

Preparation 31

A solution of sodium hydroxide (0.8 g) in water (8 ml) was added to a suspension of 4-(6-acetylaminomethylpyridin-2-yl)-2-(3-benzoylthioureido)thiazole (8.0 g) in methanol (80 ml) and the mixture was stirred at 50°–60° C. for 1 hour. Following evaporation in vacuo, the residue was mixed with water and the mixture was adjusted to pH 7.5 with 6N-hydrochloric acid. The mixture was extracted with the mixture of tetrahydrofuran and ethyl acetate and extract layer was washed with brine, dried over magnesium sulfate and evaporated in vacuo to give 4-(6-acetylaminomethylpyridin-2-yl)-2-thioureidothiazole (5.44 g).

mp: 212°–213° C. IR (Nujol): 3290, 3190, 1640, 1610 cm$^{-1}$ NMR (DMSO-d$_6$, +D$_2$O, δ): 1.94 (3H, s), 4.41 (2H, s), 7.21–7.30 (1H, m), 7.75–7.92 (3H, m)

Preparation 32

A mixture of 4-(6-acetylaminomethylpyridin-2-yl)-2-thioureidothiazole (5.3 g) and methyl iodide (1.2 ml) in a solution of methanol (53 ml) and tetrahydrofuran (25 ml) was heated under reflux for 4.5 hours. The solvent was removed by concentration in vacuo and resulting residue was triturated with ethyl acetate to give 4-(6-acetylaminomethylpyridin-2-yl)-2-[(amino)(methylthio)methyleneamino]thiazole hydriodide.

mp: 195°–197° C. (dec.) IR (Nujol): 3380, 3280, 3190, 1600 (br) cm$^{-1}$ NMR (DMSO-d$_6$, +D$_2$O, δ): 1.98 (3H, s), 2.56 (3H, s), 4.55 (2H, s), 7.44–7.55 (1H, m), 7.99–7.09 (1H, m), 7.18–8.24 (2H, m)

Preparation 33

The following compound was obtained according to a similar manner to that of Preparation 18.

6-Acetyl-2-pyridinecarbaldehyde mp: 68°–69° C. IR (Nujol): 1700 cm$^{-1}$ NMR (DMSO-d$_6$, δ): 2.73 (3H, s), 8.12–8.34 (3H, m), 10.06 (1H, s)

Preparation 34

A mixture of 6-acetyl-2-pyridinecarbaldehyde (0.5 g) and cyanomethylenetriphenylphosphorane (1.5 g) in tetrahydrofuran (5 ml) was stirred for 6 hours and the mixture was evaporated in vacuo. The residue was separated and purified by column chromatography on silica gel and eluted with a mixture of n-hexane and ethyl acetate (4:1, V/V). The eluted fast fractions containing the desired product were collected and evaporated in vacuo to give 2-acetyl-6-[2-(E)-cyanovinyl]-pyridine (0.18 g).

mp: 117° C. IR (Nujol): 2210, 1690, 1575 cm$^{-1}$ NMR (DMSO-d$_6$, δ): 2.68 (3H, s), 6.90 (1H, d, J=16.3 Hz), 7.83 (1H, d, J=16.3 Hz), 7.87 (1H, dd, J=1.1 Hz and 7.6

Hz), 7.97 (1H, dd, J=1.1 Hz and 7.6 Hz), 8.11 (1H, t, J=7.6 Hz)

The eluted another fractions containing the desired product were collected and evaporated in vacuo to give 2-acetyl-6-[2-(Z)-cyanovinyl]pyridine (0.26 g).

mp: 108°–109° C. IR (Nujol): 2210, 1690, 1575 cm$^{-1}$ NMR (DMSO-d$_6$, δ): 2.74 (3H, s), 6.16 (1H, d, J=11.7 Hz), 7.57 (1H, d, J=11.7 Hz), 7.85 (1H, dd, J=1.2 Hz and 7.7 Hz), 7.99 (1H, dd, J=1.2 Hz and 7.7 Hz), 8.14 (1H, t, J=7.7 Hz)

Preparation 35

10% Palladium on carbon (0.8 g) was added to a mixture of 2-acetyl-6-[2-(E,Z)-cyanovinyl]pyridine (0.5 g) in methanol (15 ml) and the mixture was subjected to catalytic reduction under atmospheric pressure at ambient temperature for 7 hours. The catalyst was removed by filtration and the filtrate was evaporated in vacuo to give 2-(2-cyanoethyl)-6-(1-hydroxyethyl)pyridine (0.47 g) as an oil.

IR (Film): 3380 (br), 2250, 1595, 1580 cm$^{-1}$ NMR (DMSO-d$_6$, δ): 1.37 (3H, d, J=6.7 Hz), 2.87 (2H, t, J=6.8 Hz), 3.02 (2H, t, J=6.8 Hz), 4.70–4.75 (1H, m), 5.34–5.38 (1H, m), 7.18 (1H, d, J=7.6 Hz), 7.39 (1H, d, J=7.6 Hz), 7.74 (1H, t, J=7.6 Hz)

Preparation 36

The following compound was obtained according to a similar manner to that of Preparation 18.

2-Acetyl-6-(2-cyanoethyl)pyridine

IR (Film): 2250, 1695, 1590 cm$^{-1}$ NMR (DMSO-d$_6$, δ): 2.66 (3H, s), 2.98 (2H, t, J=6.7 Hz), 3.18 (2H, t, J=6.7 Hz), 7.63 (1H, d, J=7.6 Hz), 7.84 (1H, d, J=7.6 Hz), 7.97 (1H, t, J=7.6 Hz)

Preparation 37

The following compound was obtained according to a similar manner to that of Preparation 11.

Methyl 6-bromoacetyl-2-pyridinecarboxylate

IR (Film): 1715 cm$^{-1}$ NMR (DMSO-d$_6$, δ): 3.95 (3H, s), 5.15 (2H, s), 8.13–8.35 (3H, m)

Preparation 38

30 wt % Hydrogen peroxide (80.3 ml) was added dropwise to a solution of 2-(2-acetylaminoethyl)pyridine (64.5 g) in acetic acid (65 ml) at 70°–75° C. and the mixture was stirred at the same temperature for 8 hours. After the mixture was ice-cooled and the mixture was added to a mixture of sodium sulfite (56.9 g) in ice water (200 ml). The solvent was removed by concentration in vacuo and the residue was extracted with a tetrahydrofuran. The extract solution was dried over magnesium sulfate and evaporated to give 2-(2-acetylaminoethyl)pyridine N-oxide (70.82 g).

IR (Nujol): 1640 cm$^{-1}$ NMR (DMSO-d$_6$, δ): 1.76 (3H, s), 2.93 (2H, t, J=6.7 Hz), 3.34–4.34 (2H, m), 7.25–7.40 (3H, m), 7.99 (1H, m), 8.24–8.32 (1H, m)

Preparation 39

A mixture of 2-(2-acetylaminoethyl)pyridine N-oxide (70.8 g) and dimethyl sulfate (41 ml) was stirred at ambient temperature for 1.5 hours. To the mixture was added dimethylsulfoxide (420 ml) and potassium cyanide (25.6 g) and the mixture was stirred at ambient temperature for 3 hours. To the reaction mixture was added water and extracted with chloroform. The extract layer was dried over magnesium sulfate and evaporated in vacuo to give 2-(2-acetylaminoethyl)-6-cyanopyridine (74.3 g)

IR (Nujol): 3270, 2230, 1660 cm$^{-1}$ NMR (DMSO-d$_6$, δ): 1.76 (3H, s), 2.92 (2H, t, J=7.0 Hz), 3.35–3.50 (2H, m), 7.61 (1H, dd, J=1.3 Hz and 7.6 Hz), 7.86–8.02 (3H, m)

Preparation 40

The following compound was obtained according to a similar manner to that of Preparation 5.

2-Acetyl-6-(2-acetylaminoethyl)pyridine mp: 74°–76° C. IR (Nujol): 3320, 1690, 1630, 1580 cm$^{-1}$ NMR (DMSO-d$_6$, δ): 1.78 (3H, s), 2.64 (3H, s), 2.96 (2H, t, J=7.1 Hz), 3.42–3.52 (2H, m), 7.52 (1H, dd, J=1.1 Hz and 7.6 Hz), 7.79 (1H, dd, J=1.1 Hz, 7.6 Hz), 7.87–7.92 (1H, m), 7.91 (1H, t, J=7.6 Hz)

Preparation 41

The following compound was obtained according to a similar manner to that of Preparation 44.

2-(2-Acetylaminoethyl)-6-bromoacetylpyridine mp: 101°–103° C. IR (Nujol): 3280, 1708, 1630 cm$^{-1}$ NMR (DMSO-d$_6$, δ): 1.78 (3H, s), 2.97 (2H, t, J=7.0 Hz), 3.44–3.53 (2H, m), 5.07 (2H, s), 7.58 (1H, dd, J=1.3 Hz and 7.5 Hz), 7.84–8.02 (3H, m)

Preparation 42

The following compound was obtained according to a similar manner to that of Example 62.

2-Acetylamino-6-cyanopyridine mp: 191°–193° C. (dec.) IR (Nujol): 3230, 2240, 1665, 1580 cm$^{-1}$ NMR (DMSO-d$_6$, δ): 2.12 (3H, s), 7.72 (1H, dd, J=0.7 Hz and 7.5 Hz), 8.01 (1H, t, J=7.5 Hz), 8.37 (1H, dd, J=0.7 Hz and 7.5 Hz), 10.95 (1H, s)

Preparation 43

The following compound was obtained according to a similar manner to that of Preparation 5.

2-Acetyl-6-acetylaminopyridine mp: 134°–135° C. IR (Nujol): 3350, 1690 cm$^{-1}$ NMR (DMSO-d$_6$, δ): 2.16 (3H, s), 2.62 (3H, s), 3.65 (1H, d, J=7.9 Hz), 7.96 (1H, t, J=7.9 Hz), 8.30 (1H, d, J=7.9 Hz), 10.62 (1H, s)

Preparation 44

Bromine (1.9 ml) was added dropwise to a mixture of 2-acetyl-6-acetylaminopyridine (6.6 g) and 30 wt % hydrogenbromide-acetic acid solution (7.4 ml) in acetic acid (66 ml) at ambient temperature under stirring and the mixture was stirred at 50° C. for 1.5 hours. The reaction mixture was added to a mixture of ethyl acetate and water and the mixture was adjusted to pH 8 with potassium carbonate. The separated organic layer was washed with brine, dried over magnesium sulfate and evaporated to give 2-acetylamino-6-bromoacetylpyridine (8.57 g).

mp: 118°–121° C. IR (Nujol): 3300, 1715, 1665 cm$^{-1}$ NMR (DMSO-d$_6$, δ): 2.16 (3H, s), 4.99 (2H, s), 7.72 (1H, d, J=7.5 Hz), 8.00 (1H, t, J=7.5 Hz), 8.33 (1H, d, J=7.5 Hz), 10.68 (1H, s)

Preparation 45

A solution of 4-(acetylaminomethyl)pyridine N-oxide (17.5 g), trimethylsilanecarbonitrile (53 ml) and triethylamine (43 ml) in acetonitrile (180 ml) was refluxed for 7 hours with stirring. After evaporation of the solvent, the residue was diluted with water and extracted with a mixture of ethyl acetate and tetrahydrofuran. The extract was dried over magnesium sulfate and evaporated in vacuo. The residue was chromatographed on silica gel (430 g) by eluting with a mixture of ethyl acetate and methanol (50:1) followed by recrystallization with a mixture of ethyl acetate and diisopropyl ether to give 4-(acetylaminomethyl)-2-pyridinecarbonitrile (8.66 g).

mp: 116°–117° C. IR (Nujol): 3370, 3060, 2240, 1640 cm$^{-1}$ NMR (DMSO-d$_6$, δ): 1.94 (3H, s), 4.35 (2H, d, J=6.0 Hz), 7.59 (1H, dd, J=0.8 and 5.1 Hz), 7.90 (1H, d, J=0.8 Hz), 8.52 (1H, t, J=6.0 Hz), 8.68 (1H, d, J=5.1 Hz)

Preparation 46

The following compound was obtained according to a similar manner to that of Preparation 5.

2-Acetyl-4-(acetylaminomethyl)pyridine mp: 95°–96° C. IR (Nujol): 3290, 3075, 1690, 1645 cm$^{-1}$ NMR (DMSO-d$_6$, δ): 1.92 (3H, s), 2.63 (3H, s), 4.36 (2H, d, J=6.0 Hz), 7.52 (1H, dd, J=0.9 Hz and 4.9 Hz), 7.84 (1H, d, J=0.9 Hz), 8.54 (1H, t, J=6.0 Hz), 8.65 (1H, d, J=4.9 Hz)

Preparation 47

The following compound was obtained according to a similar manner to that of Preparation 6.

4-(Acetylaminomethyl)-2-bromoacetylpyridine mp: 84°–86° C. IR (Nujol): 3390, 1710, 1645 cm$^{-1}$ NMR (CDCl$_3$, δ): 2.04 (3H, s), 4.46 (2H, s), 7.53 (1H, dd, J=0.8 Hz and 5.1 Hz), 7.92 (1H, d, J=0.8 Hz), 8.49 (1H, d, J=5.1 Hz)

Preparation 48

A solution of ferrous sulfate heptahydrate (496 g) in water (1080 ml) and tert-butylhydroperoxide (173 ml) were simultaneously added to a solution of 4-pyridinecarbonitrile (30 g), acetaldehyde (97.6 ml) and sulfuric acid (15.4 ml) in water (90 ml) at 0° C. with stirring. After stirring at the same temperature for one hour, the resulting precipitate was collected by filtration and washed with water to give 2-acetyl-4-pyridinecarbonitrile (22.5 g).

mp: 95°–96° C. IR (Nujol): 2240, 1690 cm$^{-1}$ NMR (DMSO-d$_6$, δ): 2.67 (3H, s), 8.15 (1H, dd, J=1.3 Hz and 4.6 Hz), 8.30 (1H, d, J=1.3 Hz), 8.99 (1H, d, J=4.6 Hz)

Preparation 49

The following compound was obtained according to a similar manner to that of Preparation 11.

2-Bromoacetyl-4-pyridinecarbonitrile hydrobromide mp: 151°–152° C. IR (Nujol): 1720 cm$^{-1}$ NMR (DMSO-d$_6$, δ): 4.97 (2H, s), 8.17 (1H, dd, J=1.0 Hz and 4.6 Hz), 8.31 (1H, d, J=1.0 Hz), 8.99 (1H, d, J=4.6 Hz)

Preparation 50

30% Hydrogen peroxide (130 ml) was added to ethyl pyruvate (216 g) at −5° to 5° C. with stirring. This solution was then added to a mixture of 4-acetylpyridine (15.0 g), concentrated sulfuric acid (12.4 g), ferrous sulfate heptahydrate (345 g), dichloromethane (1.5 l) and water (100 ml) at the same temperature with stirring. After further stirring for 30 minutes, the resulting organic layer was separated. The solution was washed with aqueous sodium sulfite and then water, dried over magnesium sulfate and evaporated in vacuo. The residue was purified by silica gel column chromatography by eluting with a mixture of ethyl acetate and toluene (1:20) to give ethyl 4-acetyl-2-pyridinecarboxylate (5.79 g).

mp: 43°–44° C. IR (Nujol): 1715, 1690 cm$^{-1}$ NMR (DMSO-d$_6$, δ): 1.36 (3H, t, J=7.1 Hz), 4.40 (2H, q, J=7.1 Hz), 8.08 (1H, dd, J=1.7 Hz and 4.9 Hz), 8.35 (1H, d, J=1.7 Hz), 8.95 (1H, d, J=4.9 Hz)

Preparation 51

The following compound was obtained according to a similar manner to that of Preparation 6.

Ethyl 4-bromoacetyl-2-pyridinecarboxylate hydrobromide mp: 169°–170° C. IR (Nujol): 1745, 1715 cm$^{-1}$ NMR (CD$_3$OD, δ): 1.50 (3H, t, J=7.1 Hz), 4.61 (2H, q, J=7.1 Hz), 8.39 (1H, d, J=1.8 Hz and 5.9 Hz), 8.63 (1H, d, J=1.8 Hz), 8.98 (1H, d, J=5.9 Hz)

Preparation 52

The following compound was prepared according to a similar manner to that of Preparation 48.

Methyl 6-acetyl-4-chloro-2-pyridinecarboxylate mp: 98°–99° C. IR (Nujol): 1725, 1710 cm$^{-1}$ NMR (DMSO-d$_6$, δ): 2.67 (3H, s), 3.96 (3H, s), 8.15 (1H, d, J=2.0 Hz), 8.29 (1H, d, J=2 Hz)

Preparation 53

A solution of methyl 6-acetyl-4-chloro-2-pyridinecarboxylate (6.55 g) and surfuryl chloride (2.73 ml) in acetic acid (33 ml) was stirred at ambient temperature for 14 hours and further at 50° C. for three hours. The solvent was evaporated in vacuo and the residue was mixed with water. The resulting precipitate was collected by filtration and washed with water to give methyl 4-chloro-6-chloroacetyl-2-pyridinecarboxylate (6.75 g).

mp: 115°–118° C. IR (Nujol): 1725 cm$^{-1}$ NMR (DMSO-d$_6$, δ): 3.95 (3H, s), 5.29 (2H, s), 8.27 (1H, d, J=2.0 Hz), 8.35 (1H, d, J=2.0 Hz)

Preparation 54

A mixture of 2-acetylaminomethylpyridine N-oxide (1.00 g) and dimethyl sulfate (0.63 ml) was stirred for three hours. Dimethyl sulfoxide (6 ml) and potassium cyanide (392 mg) were added to the mixture and the solution was stirred for two hours at ambient temperature. Additional potassium cyanide (392 mg) was added to the mixture and which was further stirred for two hours. After the solvent was removed by concentration, the residue was mixed with water and extracted with ethyl acetate. The extract was dried over magnesium sulfate and evaporated in vacuo. The residue was chromatographed on silica gel (15 g) by eluting with a mixture of ethyl acetate and methanol (20:1) to give 6-acetylaminomethyl-2-pyridinecarbonitrile (0.16 g).

IR (Nujol): 3260, 2230, 1650 cm$^{-1}$

Preparation 55

The following compound was obtained according to a similar manner to that of Preparation 48.

2-Acetyl-6-(acetylaminomethyl)pyridine

IR (Nujol): 3300, 1690, 1650 cm$^{-1}$

Preparation 56

The following compound was obtained according to a similar manner to that of Preparation 48.

4-Acetyl-2-carbamoylpyridine mp: 182° to 183° C. IR (Nujol): 3440, 3320, 1690 cm$^{-1}$ NMR (DMSO-d$_6$, δ): 2.69 (3H, s), 7.82 (1H, s), 8.01 (1H, dd, J=1.7 Hz and 15.0 Hz), 8.25 (1H, s), 8.40 (1H, d, J=1.7 Hz), 8.86 (1H, d, J=5.0 Hz)

Preparation 57

The following compound was obtained according to a similar manner to that of Preparation 6.

4-Bromoacetyl-2-carbamoylpyridine hydrobromide
mp: >300° C. IR (Nujol): 3280, 3240, 3150, 1710, 1690 cm$^{-1}$ NMR (CD$_3$OD, δ): 4.93 (2H, s), 8.38 (1H, dd, J=1.7 Hz and 5.9 Hz), 8.78 (1H, d, J=1.7 Hz), 8.96 (1H, d, J=5.9 Hz)

Preparation 58

Bromine (6.0 g) was added slowly to a solution of 5-acetyl-3-pyridinecarboxylic acid methyl ester (6.0 g) in dioxane (50 ml) at room temperature. The mixture was stirred at room temperature for 1 hour and then heated at 60°-70° C. for 5 hours. The resulting precipitate was collected by filtration to afford 5-bromoacetyl-3-pyridinecarboxylic acid methyl ester hydrobromide (10.0 g).

IR (Nujol): 3060, 1735, 1705 cm$^{-1}$ NMR (DMSO-d$_6$, δ): 3.94 (3H, s), 5.11 (2H, s), 8.73 (1H, t, J=2.1 Hz), 9.30 (1H, d, J=2.1 Hz), 9.38 (1H, d, J=2.1 Hz)

Preparation 59

A suspension of 5-acetyl-3-pyridinecarboxylic acid methyl ester (5.0 g) in 28% ammonia solution (30 ml) was stirred at room temperature for 2 hours. The resulting precipitate was collected by filtration to afford 3-acetyl-5-carbamoylpyridine (3.38 g).

mp: 158°-160° C. NMR (DMSO-d$_6$, δ): 2.68 (3H, s), 7.76 (1H, s), 8.36 (1H, s), 8.68 (1H, t, J=2.1 Hz), 9.22 (1H, d, J=2.1 Hz), 9.23 (1H, d, J=2.1 Hz)

Preparation 60

Phosphorus oxychloride (2.75 g) was added to a solution of 3-acetyl-5-carbamoylpyridine (2.8 g) in N,N-dimethylformamide (30 ml) with cooling on an ice-water bath. The mixture was stirred with cooling for 1.5 hours. The solvent was removed under reduced pressure. The residue was dissolved in water (150 ml) and the mixture was extracted with ethyl acetate (100 ml). The extract was dried with magnesium sulfate and then evaporated. The residue was chromatographed on a silica gel column eluting with chloroform to afford 3-acetyl-5-cyanopyridine (1.21 g).

mp: 92° C. IR (Nujol): 3060, 2250, 1690 cm$^{-1}$ NMR (DMSO-d$_6$, δ): 2.67 (3H, s), 8.82 (1H, t, J=2.1 Hz), 9.24 (1H, d, J=2.1 Hz), 9.32 (1H, d, J=2.1 Hz)

Preparation 61

A mixture of 4-(6-acetylaminomethylpyridin-2-yl)2-aminothiazole (7.0 g) and methyl isothiocyanate (6.2 g) in ethanol (140 ml) was heated under reflux for 40 minutes and then the mixture was cooling to ambient temperature. To the mixture was added ethyl acetate (140 ml) and isolated precipitate was collected by filtration to give 4-(6-acetylaminomethylpyridin-2-yl)-2-(3-methylthioureido)thiazole (1.88 g).

mp: 226°-228° C. IR (Nujol): 3290, 1640, 1590 cm$^{-1}$ NMR (DMSO-d$_6$, δ): 1.93 (3H, s), 3.07 (3H, d, J=4.4 Hz), 4.38 (2H, d, J=5.9 Hz), 7.22 (1H, t, J=4.5 Hz), 7.71 (1H, s), 7.84 (2H, d, J=4.5 Hz), 8.47 (1H, t, J=5.9 Hz), 9.19 (1H, br s), 11.77 (1H, s)

Preparation 62

Methanesulfonic acid (18.6 g) was added to a solution of 2-acetyl-6-(propionylaminomethyl)pyridine (40.0 g) in dioxane (800 ml) at room temperature. The mixture was stirred at room temperature for 15 minutes. Bromine (34.1 g) was added slowly to the mixture at room temperature. The mixture was heated at 50° C. for 3 hours. To the mixture sodium hydrogencarbonate (65.2 g), thiourea (17.7 g) and methanol (800 ml) was added. The mixture was heated at 50° C. for 4 hours. The solvent was removed under reduced pressure and the residue was dissolved in water (700 ml). The mixture was extracted with a mixture of ethyl acetate (700 ml) and tetrahydrofuran (700 ml). The extract was dried with magnesium sulfate and then was evaporated. The residue was crystallized from acetone to afford 2-amino-4-(6-propionylaminomethylpyridin-2-yl)thiazole (26.9 g).

mp: 134°-136° C. IR (Nujol): 3270, 3160, 1630 cm$^{-1}$ NMR (DMSO-d$_6$, δ): 8.37 (1H, t, J=5.9 Hz), 7.77 (1H, t, J=7.7 Hz), 7.68 (1H, dd, J=7.7 Hz and 1.1 Hz), 7.24 (1H, s), 7.12 (1H, dd, J=7.7 Hz and 1.1 Hz), 7.10 (2H, s), 4.36 (2H, d, J=5.9 Hz), 2.21 (2H, q, J=7.7 Hz), 1.05 (3H, t, J=7.7 Hz)

Preparation 63

Benzoyl chloride (7.7 g) was added slowly to a solution of sodium thiocyanate (4.8 g) in acetone (220 ml) under refluxing and the mixture was refluxed for 15 minutes. 2-Amino-4-(6-propionylaminomethylpyridin-2-yl)thiazole (12.0 g) was added to the mixture. The mixture was refluxed for 4 hours. The resulting precipitate was collected by filtration and was washed with water and then acetone to afford 2-(3-benzoylthioureido)-4-(6-propionylaminomethylpyridin-2-yl)thiazole (16.5 g).

mp: 230°-231° C. (dec.) IR (Nujol): 3290, 1670, 1640 cm$^{-1}$ NMR (DMSO-d$_6$, δ): 14.29 (1H, s), 12.23 (1H, s), 8.43 (1H, t, J=5.9 Hz), 8.03 (2H, d, J=7.2 Hz), 7.95 (1H, s), 7.92-7.83 (2H, m), 7.71 (1H, t, J=7.2 Hz), 7.57 (2H, t, J=7.2 Hz), 7.24 (1H, dd, J=2.8 Hz and 6.0 Hz), 4.42 (2H, d, J=5.9 Hz), 2.23 (2H, q, J=7.6 Hz), 1.07 (3H, t, J=7.6 Hz)

Preparation 64

The following compound was obtained according to a similar manner to that of Preparation 63.

2-(3-Benzoylthioureido)-4-(6-ethoxycarbonylaminomethylpyridin-2-yl)thiazole mp: 221° to 222° C. (dec.) IR (Nujol): 3270, 1680, 1600 cm$^{-1}$ NMR (DMSO-d$_6$, δ): 14.29 (1H, s), 12.23 (1H, s), 8.03 (2H, dd, J=1.5 Hz and 7.1 Hz), 7.92-7.87 (3H, m), 7.83-7.67 (2H, m ), 7.57 (2H, b, J=7.1 Hz), 7.26 (1H, dd, J=3.6 Hz and 5.2 Hz), 4.34 (2H, d, J=6.1 Hz), 4.05 (2H, q, J=7.1 Hz), 1.20 (3H, t, J=7.1 Hz)

Preparation 65

The following compound was obtained according to a similar manner to that of Preparation 63.

2-(3-Benzoylthioureido)-4-(2-acetylaminomethylthiazol-4-yl)thiazole mp: 237°-238° C. (dec.) IR (Nujol): 3275, 1670, 1645 cm$^{-1}$ NMR (DMSO-d$_6$, δ): 14.26 (1H, s), 12.23 (1H, s), 8.81 (1H, t, J=6.0 Hz), 8.02 (2H, d, J=7.0 Hz), 7.88 (1H, s), 7.70 (1H, t, J=7.0 Hz), 7.60 (1H, s), 7.57 (2H, t, J=7.0 Hz), 4.57 (2H, d, J=6.0 Hz), 1.92 (3H, s)

Preparation 66

A suspension of 2-amino-4-(6-propionylaminomethylpyridin-2-ylthiazole (12.0 g) and conc. hydrochloric acid (12 ml) in ethanol was refluxed for 27 hours. The resulting precipitate was collected by filtration to afford 2-amino-4-(6-aminomethylpyridin-2-yl)thiazole trihydrochloride (8.9 g).

mp: 279°–281° C. (dec.) IR (Nujol): 3300, 1620 cm$^{-1}$ NMR (DMSO-d$_6$, δ): 9.60–8.40 (4H, br), 8.07–7.96 (2H, m), 7.80 (1H, s), 7.52 (1H, dd, J=1.6 Hz and 6.8 Hz), 4.30 (2H, q, J=5.7 Hz)

Preparation 67

Ethyl chloroformate (3.7 g) was added slowly to a suspension of 2-amino-4-(6-aminomethylpyridin-2-yl)thiazole trihydrochloride (8.9 g) and triethylamine (11.4 g) in N,N-dimethylformamide (80 ml) and tetrahydrofuran (80 ml) with cooling on an ice bath. The mixture was stirred with cooling for 1.5 hours and then at room temperature for 1 hours. The solvent was removed under reduced pressure. The residue was dissolved in water (300 ml). The mixture was alkalized with a saturated aqueous potassium carbonate solution and then was extracted with a mixture of ethyl acetate (500 ml) and tetrahydrofuran (100 ml). The extract was dried over magnesium sulfate and then was evaporated to afford 2-amino-4-(6-ethoxycarbonylaminomethylpyridin-2-yl)thiazole (10.51 g).

IR (Film): 3300, 1720 cm$^{-1}$ NMR (DMSO-d$_6$, δ): 7.83–7.68 (3H, m), 7.24 (1H, s), 7.18–7.12 (3H, m), 4.30 (2H, d, J=6.2 Hz), 4.04 (2H, q, J=7.1 Hz), 1.19 (3H, t, J=7.1 Hz)

Preparation 68

A suspension of 2-amino-4-bromoacetylthiazole hydrobromide (14.0 g) and N-[(thiocarbamoyl)methyl]-acetamide (6.1 g) in ethanol (300 ml) was stirred at room temperature for 24 hours. The insoluble material was removed by filtration. The solvent was removed under reduced pressure. The residue was suspended in water (300 ml). The mixture was alkalized to pH 10 with a saturated aqueous potassium carbonate solution and then was extracted with a mixture of ethyl acetate (500 ml) and tetrahydrofuran (100 ml). The extract was dried over magnesium sulfate and then was evaporated to afford 4-(2-acetylaminomethylthiazol-4-yl)-2-aminothiazole (5.83 g).

mp: 201°–202° C. (dec.) IR (Nujol): 3300, 1740, 1650 cm$^{-1}$ NMR (DMSO-d$_6$, δ): 8.77 (1H, t, J=6.0 Hz), 7.50 (1H, s), 7.10 (2H, s), 6.89 (1H, s), 4.52 (2H, d, J=6.0 Hz), 1.91 (3H, s)

Preparation 69

4N-Dioxanoic hydrogen chloride (10 ml) was added to a suspension of 4-(2-acetylaminomethylthiazol-4-yl)-2-aminothiazole (0.75 g) in methanol (30 ml). The mixture was stirred at room temperature for 40 minutes, and diisopropyl ether (50 ml) was added. The resulting precipitate was collected by filtration. Recrystallization from a mixture of methanol and dioxane afforded 4-(2-acetylaminomethylthiazol-4-yl)-2-aminothiazole hydrochloride (0.35 g).

mp: 218°–221° C. (dec.) IR (Nujol): 3200, 1635 cm$^{-1}$ NMR (DMSO-d$_6$, δ): 8.86 (1H, t, J=5.9 Hz), 8.01 (1H, s), 7.15 (1H, s), 4.54 (2H, d, J=5.9 Hz), 1.92 (3H, s)

Preparation 70

A mixture of 4-(6-acetylaminomethylpyridin-2-yl)-2-(3-methylthioureido)thiazole (1.5 g) and methyl iodide (0.45 ml) in a solution of methanol (15 ml) and tetrahydrofuran (8 ml) was heated under reflux for 9 hours. The solvent was removed by concentration and the residue was triturated with ethyl acetate to give 4-(6-acetylaminomethylpyridin-2-yl)-2-[(methylamino)(methylthio)methyleneamino]thiazole hydriodide (1.44 g).

mp: 187°–189° C. IR (Nujol): 3470, 1620, 1600 cm$^{-1}$ NMR (DMSO-d$_6$, δ): 1.97 (3H, s), 2.55 (3H, s), 3.07 (3H, s), 4.51 (2H, d, J=5.7 Hz), 7.40–7.52 (1H, m), 8.02–8.20 (2H, m), 8.07 (1H, s), 8.67 (1H, t, J=5.7 Hz)

Preparation 71

A solution of sodium hydroxide (3.7 g) in water (30 ml) was added to a suspension of 2-(3-benzoylthioureido)-4-(6-propionylaminomethylpyridin-2-yl)thiazole (16.5 g) in methanol (300 ml) at room temperature. The mixture was heated at 60° C. for 4.5 hours. The solvent was removed under reduced pressure. The residue was dissolved in water (200 ml). The mixture was neutralized with 6N hydrochloric acid. The resulting precipitate was collected by filtration to afford 4-(6-propionylaminomethylpyridin-2-yl)-2-thioureidothiazole (14.67 g).

mp: 223°–225° C. (dec.) IR (Nujol): 3270, 3120, 1640, 1620 cm$^{-1}$ NMR (DMSO-d$_6$, δ): 11.65 (1H, br), 9.00–8.00 (3H, br), 7.85 (1H, t, J=7.8 Hz), 7.79 (1H, dd, J=7.8 Hz and 1.6 Hz), 7.73 (1H, s), 7.21 (1H, dd, J=7.8 Hz and 1.6 Hz), 4.39 (2H, d, J=5.9 Hz), 2.22 (2H, q, J=7.6 Hz), 1.06 (3H, t, J=7.6 Hz)

Preparation 72

The following compound was obtained according to a similar manner to that of Preparation 71.

4-(6-Ethoxycarbonylaminomethylpyridin-2-yl)-2-thioureidothiazole mp: 210°–212° C. (dec.) IR (Nujol): 3310, 3130, 1690, 1600 cm$^{-1}$ NMR (DMSO-d$_6$, δ): 11.74 (1H, s), 8.77 (1H, br), 8.33 (1H, br), 7.90–7.74 (3H, m), 7.71 (1H, s), 7.23 (1H, dd, J=1.0 Hz and 7.2 Hz), 4.32 (2H, d, J=6.1 Hz), 4.04 (2H, q, J=7.1 Hz), 1.19 (3H, t, J=7.1 Hz)

Preparation 73

The following compound was obtained according to a similar manner to that of Preparation 71.

4-(2-Acetylaminomethylthiazol-4-yl)-2-thioureidothiazole mp: 230°–231° C. (dec.) IR (Nujol): 3270, 1640, 1615 cm$^{-1}$ NMR (DMSO-d$_6$, δ): 11.71 (1H, s), 9.00–8.00 (3H, br), 7.81 (1H, s), 7.38 (1H, s), 4.55 (2H, d, J=6.0 Hz), 1.92 (3H, s)

Preparation 74

A suspension of 4-(6-propionylaminomethylpyridin-2-yl)-2-thioureidothiazole (14.67 g) and methyl iodide (7.77 g) in methanol (300 ml) was refluxed for 3 hours. The solvent was removed under reduced pressure. The residue was crystallized from ethyl acetate to afford 2-[(amino)(methylthio)methyleneamino]-4-(6-propionylaminomethylpyridin-2-yl)thiazole hydriodide (13.68 g).

mp: 194°–196° C. (dec.) IR (Nujol): 3350, 3200, 1650, 1610 cm$^{-1}$ NMR (DMSO-d$_6$, δ): 9.29 (2H, br), 8.55 (1H, t, J=5.8 Hz), 8.13–8.03 (3H, m), 7.40 (1H, dd, J=2.7 Hz and 6.2 Hz), 4.50 (2H, d, J=5.8 Hz), 2.52 (3H, s), 2.24 (2H, q, J=7.5 Hz), 1.06 (3H, t, J=7.5 Hz)

Preparation 75

The following compound was obtained according to a similar manner to that of Preparation 74.

2-[(Amino)(methylthio)methyleneamino]-4-(6-ethoxycarbonylaminomethylpyridin-2-yl)thiazole hydriodide mp: 153° to 155° C. (dec.) IR (Nujol): 3350, 1685, 1610 cm$^{-1}$ NMR (DMSO-d$_6$, δ): 9.51 (1H, br), 8.40–8.05 (3H, m), 8.05–7.80 (1H, m), 7.60–7.20 (2H, m), 4.46 (2H, d, J=5.4 Hz), 4.06 (2H, q, J=7.0 Hz), 2.59 (3H, s), 1.20 (3H, t, J=7.0 Hz)

Preparation 76

The following compound was obtained according to a similar manner to that of Preparation 74.

2-[(Amino)(methylthio)methyleneamino]-4-(2-acetylaminomethylthiazol-4 -yl)thiazole hydriodide mp: 178°–180° C. (dec.) IR (Nujol): 3250, 1640 cm$^{-1}$ NMR (DMSO-d$_6$, δ): 9.53 (1H, br), 8.80 (1H, t, J=6.0 Hz), 8.12 (1H, s), 7.52 (1H, s), 4.55 (2H, d, J=6.0 Hz), 2.57 (3H, s), 1.92 (3H, s)

EXAMPLE 1

A mixture of 2-(acetylaminometyl)-6-bromoacetylpyridine hydrobromide (3.34 g) and diaminomethylenethiourea (1.01 g) in methanol (50 ml) was refluxed for 10 hours with stirring. The resulting precipitate was collected, dissolved in water (50 ml) and the solution was made basic with aqueous potassium carbonate. The separated product was collected and washed with water to give 4-(6-aminomethylpyridin-2-yl)-2-(diaminomethyleneamino)thiazole (0.90 g).

mp: 228°–229° C. IR (Nujol): 3350, 3150
NMR (DMSO-d$_6$, δ): 3.85 (2H, s), 6.96 (4H, br s), 7.22–7.44 (3H, m), 7.73–7.83 (3H, m)

EXAMPLE 2

Acetic anhydride was added dropwise to a solution of 4-(6-aminomethylpyridin-2-yl)-2-(diaminomethyleneamino)thiazole (0.44 g) in pyridine (4.4 ml). After being stirred for two hours at ambient temperature, the mixture was mixed with aqueous potassium carbonate and extracted with ethyl acetate. The extract was washed with water, dried over magnesium sulfate and evaporated in vacuo to give 4-(6-acetylaminomethylpyridin-2-yl)-2-(diaminomethyleneamino)thiazole. The residue was converted to the hydrochloride in a usual manner and the salt was recrystallized from a mixture of methanol and diisopropyl ether to give 4-(6-acetylaminomethylpyridin-2-yl)-2-(diaminomethyleneamino)thiazole dihydrochloride (0.43 g).

mp: 218°–219° C. IR (Nujol): 3340, 3160, 1705, 1650 cm$^{-1}$ NMR (DMSO-d$_6$, δ): 1.96 (3H, s), 4.56 (2H, d, J=6 Hz), 7.45 (1H, d, J=7.5 Hz), 8.10 (1H, t, J=7.5 Hz), 8.24 (1H, d, J=7.5 Hz), 8.25 (1H, s), 8.46 (4H, br s), 8.74 (1H, t, J=6 Hz) Anal. Calcd. for C$_{12}$H$_{14}$N$_6$OS.2HCl.2/3H$_2$O: C 38.41, H 4.66, N 22.39, Cl 18.89, H$_2$O 3.20 found: C 38.14, H 4.56, N 22.25, Cl 19.06, H$_2$O 2.65

EXAMPLE 3

A mixture of 4-(6-aminomethylpyridin-2-yl)-2-(diaminomethyleneamino)thiazole (0.50 g) and dimethyl N-cyanodithioiminocarbonate [(CH$_3$S)$_2$C=N-CN] (0.29 g) in ethanol (10 ml) was refluxed for one hour to give 2-(diaminomethyleneamino)-4-[6-(3-cyano-2-methylisothioureido)methylpyridin-2-yl]thiazole of a crude product. After being concentrated to dry the above product, 40 weight % methanolic methylamine (1.6 ml) and N,N-dimethylformamide (10 ml) was added and the mixture was stirred at 60° C. for 5 hours. The solvent was evaporated in vacuo and the residue was mixed with water. The resulting precipitate was collected by filtration and recrystallized from aqueous N,N-dimethylformamide to give 4-[6-(2-cyano-3-methylguanidino)methylpyridin-2-yl]-2-(diaminomethyleneamino)thiazole (0.42 g).

mp: 245°–246° C. IR (Nujol): 3440, 3400, 3290, 2170, 1630 cm$^{-1}$ NMR (DMSO-d$_6$, δ): 2.76 (3H, d, J=4.5 Hz), 4.46 (2H, d, J=5.5 Hz), 6.93 (4H, s), 7.14–7.26 (2H, m), 7.42 (1H, s), 7.57 (1H, t, J=5.5 Hz), 7.79–7.88 (2H, m) Anal. Calcd. for C$_{13}$H$_{15}$N$_9$S.¼H$_2$O: C 46.76, H 4.68, N 37.76, H$_2$O 1.34 found: C 46.93, H 4.65, N 37.46, H$_2$O 1.14

EXAMPLE 4.

A mixture of 4-(6-aminomethylpyridin-2-yl)-2-(diaminomethyleneamino)thiazole (0.64 g), 1N-hydrochloric acid (5.15 ml) and potassium cyanate (0.21 g) in water (6.4 ml) was stirred for 19 hours at ambient temperature. The solution was made basic with aqueous potassium carbonate and the resulting precipitate was collected by filtration. The free base was converted to the hydrochloride in a usual manner followed by recrystallization from aqueous methanol to give 2-(diaminomethyleneamino)-4-(6-ureidomethylpyridin-2-yl)thiazole dihydrochloride (0.45 g).

mp: 210°–211° C. IR (Nujol): 1705, 1650 cm$^{-1}$ NMR (DMSO-d$_6$, δ): 4.57 (2H, s), 7.64 (1H, d, J=7.5 Hz), 8.26–8.41 (2H, m), 8.51 (10H, s) Anal. Calcd. for C$_{11}$H$_{13}$N$_7$OS.2HCl.½H$_2$O: C 35.68, H 4.26, N 26.48, Cl 19.15, H$_2$O 1.62 found: C 35.74, H 4.21, N 26.25, Cl 19.46, H$_2$O 1.73

EXAMPLE 5

A mixture of 2-acetylaminomethyl-5-bromoacetylthiazole (6.30 g) and diaminomethylenethiourea [(H$_2$N)$_2$C=NCSNH$_2$] (1.77 g) in acetone (90 ml) was refluxed for 10 hours with stirring. The resulting precipitate was collected by filtration to give 4-(2-acetylaminomethylthiazol-5-yl)-2-(diaminomethyleneamino)thiazole dihydrobromide (2.21 g).

mp: 218°–219° C. IR (Nujol): 3280, 3200, 3150, 1675, 1655 cm$^{-1}$ NMR (DMSO-d$_6$, δ): 1.92 (3H, s), 4.52 (2H, d, J=6 Hz), 7.67 (1H, s), 8.25 (1H, s), 8.27 (4H, s), 8.85 (1H, t, J=6 Hz), 12.11 (1H, br s) MS (m/e): 296

EXAMPLE 6

The following compound was obtained from 4-(2-acetylaminomethylthiazol-5-yl)-2-(diaminomethyleneamino)thiazole dihydrobromide according to a similar manner to that of Example 10.

4-(2-Aminomethylthiazol-5-yl)-2-(diaminomethyleneamino)thiazole mp: 189°–191° C. IR (Nujol): 3430, 3260, 1650, 1630 cm$^{-1}$ NMR (DMSO-d$_6$, δ): 3.97 (2H, s), 6.93 (4H, s), 7.00 (1H, s), 7.97 (1H, s)

EXAMPLE 7

A mixture of 4-(2-aminomethylthiazol-5-yl)-2-(diaminomethyleneamino)thiazole (0.45 g) and dimethyl N-cyanodithioiminocarbonate [(CH$_3$S)$_2$C=N-CN] (0.26 g) in ethanol (10 ml) was refluxed for 5 hours with stirring to give 4-[2-(3-cyano-2-methylisothioureido)methylthiazol-5-yl]-2-(diaminomethyleneamino)thiazole as a crude product. After cooling to ambient temperature, 40% aqueous methylamine by weight (1.4 ml) was added to the suspension and the mixture was stirred for 12 hours at ambient temperature. The solvent was evaporated in vacuo and the residue was mixed with water (5 ml) and ethyl acetate (5 ml). The resulting precipitate was collected and recrystallized from aqueous N,N-dimethylformamide to give 4-[2-(2-cyano-3-methylguanidino)methylthiazol-5-yl]-2-(diaminomethyleneamino)thiazole (0.35 g).

mp: 258°-259° C. IR (Nujol): 3480, 3360, 3270, 2150 cm$^{-1}$ NMR (DMSO-d$_6$, δ): 2.74 (3H, d, J=4.5 Hz), 4.59 (2H, d, J=6 Hz), 6.92 (4H, s), 7.08 (1H, s), 7.32 (1H, q, J=4.5 Hz), 7.85 (1H, t, J=6 Hz), 8.04 (1H, s) Anal. Calcd. for C$_{11}$H$_{13}$N$_9$S$_2$: C 39.39, H 3.91, N 37.59 Found: C 39.30, H 3.95, N 37.40

EXAMPLE 8

A solution of 4-(2-acetylaminomethylthiazol-5-yl)-2-(diaminomethyleneamino)thiazole (1.46 g) and concentrated hydrochloric acid (2.18 ml) in ethanol (15 ml) was refluxed for 5 hours with stirring. The solvent was evaporated in vacuo. The residue was made basic to pH 10 with 20% aqueous potassium carbonate and extracted with a mixture of ethyl acetate and tetrahydrofuran. The extract was dried over magnesium sulfate and evaporated in vacuo to give 4-(2-aminomethylthiazol-5-yl)-2-(diaminomethyleneamino)thiazole. 1N-hydrochloric acid (4 ml) and then potassium cyanate (360 mg) was added to the suspension of the above residue in water (10 ml) and the mixture was stirred for two hours at ambient temperature. The reaction mixture was alkalized to pH 10 with 20% aqueous potassium carbonate and extracted with a mixture of ethyl acetate and tetrahydrofuran. The extract was dried over magnesium sulfate and evaporated in vacuo. The obtained free base was converted to the dihydrochloride in an usual manner, and which was recrystallized from a mixture of methanol, water and tetrahydrofuran to give 2-(diaminomethyleneamino)-4-(2-ureidomethylthiazol-5-yl)thiazole dihydrochloride (0.65 g).

mp: 184°-185° C. IR (Nujol): 3250, 3100, 1660 cm$^{-1}$ NMR (DMSO-d$_6$, δ): 4.46 (2H, s), 6.21 (4H, br s), 7.62 (1H, s), 8.27 (1H, s), 8.37 (4H, s), 12.85 (1H, br s)

EXAMPLE 9

Bromine (2.2 g) was added slowly to a solution of 4-acetyl-2-acetylaminomethylthiazole (2.2 g) in acetic acid (20 ml) and water (20 ml), and the mixture was heated at 70° C. for 4 hours. The solvent was removed under reduced pressure to give crude product of 2-acetylaminomethyl-4-bromoacetylthiazole. The above residue was dissolved in ethanol (50 ml). Diaminomethylenethiourea (1.3 g) was added to the solution and the mixture was refluxed for 4 hours. The solvent was removed under reduced pressure. The residue was dissolved in water and then the solution was alkalized with a saturated aqueous potassium carbonate solution. The resulting precipitate was collected by filtration. The filtrate was extracted by ethyl acetate and then the solvent was removed under reduced pressure. The residue and the precipitate were chromatographed on an alumina column eluting with a mixture of chloroform and methanol (10:1). Recrystallization from water afforded 4-(2-acetylaminomethylthiazol-4-yl)-2-(diaminomethyleneamino)thiazole (430 mg).

mp: 255°-256° C. IR (Nujol): 3250, 1640 cm$^{-1}$ NMR (DMSO-d$_6$, δ): 1.91 (3H, s), 4.54 (2H, d, J=5.9 Hz), 6.88 (4H, s), 7.02 (1H, s), 7.79 (1H, s), 8.77 (1H, t, J=5.9 Hz) Anal. Calcd. for C$_{10}$H$_{12}$N$_6$OS$_2$.4/5H$_2$O: C 38.65, H 4.41, N 27.04 Found: C 38.51, H 4.31, N 27.00

EXAMPLE 10

Concentrated hydrochloric acid (72.4 ml) was added slowly to a suspension of 4-(2-acetylaminomethylthiazol-4-yl)-2-(diaminomethyleneamino)thiazole (6.58 g) in ethanol (280 ml). The mixture was refluxed for 2 hours. The resulting precipitate was collected by filtration. Recrystallization from a mixture of methanol and water afforded 4-(2-aminomethylthiazol-4-yl)-2-(diaminomethyleneamino)thiazole dihydrochloride (6.98 g).

mp: >300° C. IR (Nujol): 3300, 1680, 1600 cm$^{-1}$ NMR (DMSO-d$_6$, δ): 4.47 (2H, s), 7.59 (1H, s), 8.41 (4H, s), 8.45 (1H, s), 8.76 (3H, s), 12.82 (1H, s) Anal. Calcd. for C$_8$H$_{10}$N$_6$S$_2$.2HCl.9/10H$_2$O C 27.98, H 4.05, N 24.47, Cl 20.64, H$_2$O 4.72 Found: C 27.69, H 3.87, N 24.13, Cl 20.85, H$_2$O 4.38

EXAMPLE 11

A solution of 4-(2-aminomethylthiazol-4-yl)-2-(diaminomethyleneamino)thiazole (1.0 g) and potassium cyanate (0.5 g) in water (50 ml) was stirred for 3.5 hours at room temperature. The resulting precipitate was collected by filtration. The precipitate was suspended in water (30 ml) and then a saturated aqueous potassium carbonate solution (20 ml) was added. The mixture was stirred for 1 hour at room temperature. The resulting precipitate was collected by filtration. Recrystallization from a mixture of methanol and water afforded 2-(diaminomethyleneamino)-4-(2-ureidomethylthiazol-4-yl)thiazole (0.35 g).

mp: 261°-262° C. (dec.) IR (Nujol): 3450, 3350, 1660, 1630 cm$^{-1}$ NMR (DMSO-d$_6$, δ): 4.46 (2H, d, J=6.1 Hz), 5.77 (2H, s), 6.80 (1H, t, J=6.1 Hz), 6.88 (4H, s), 7.01 (1H, s), 7.76 (1H, s) Anal. Calcd. for C$_9$H$_{11}$N$_7$OS$_2$: C 36.35, H 3.73, N 32.97 Found: C 36.52, H 3.72, N 33.36

EXAMPLE 12

Methanesulfonic acid (2.16 g) was added to a suspension of 2-(diaminomethyleneamino)-4-(2-ureidomethylthiazol-4-yl)thiazole (3.19 g) in methanol (95 ml). The mixture was stirred at room temperature for 1 hour. The resulting precipitate was collected by filtration. Recrystallization from a mixture of acetonitrile and water afforded 2-(diaminomethyleneamino)-4-(2-ureidomethylthiazol-4-yl)thiazole methanesulfonate (3.2 g).

mp: 257°-259° C. (dec.) IR (Nujol): 3490, 3320, 1680, 1610 cm$^{-1}$ NMR (DMSO-d$_6$, δ): 2.48 (3H, s), 4.49 (2H, d, J=6.0 Hz), 5.82 (2H, s), 6.89 (1H, t, J=6.0 Hz), 7.56 (1H, s), 8.20 (1H, s), 8.34 (4H, s), 12.03 (1H, s)

EXAMPLE 13

Triethylamine (0.7 g) was added to a suspension of 4-(2-aminomethylthiazol-4-yl)-2-(diaminomethyleneamino)thiazole (1.0 g) in methanol (20 ml). To the mixture was added methylisocyanate (0.21 g). The mixture was stirred at room temperature for 1.5 hours. The solvent was removed under the reduced pressure and the residue was chromatographed on a Silica gel column eluting with a mixture of chloroform and methanol (10:1). Recrystallization from a mixture of water and methanol afforded 2-(diaminomethyleneamino)-4-[2-(3-methylureido)methylthiazol-4-yl]thiazole (0.5 g).

mp: 229°-230° C. (dec.) IR (Nujol): 3425, 3330, 1630, 1610 cm$^{-1}$ NMR (DMSO-d$_6$, δ): 2.59 (3H, d, J=4.6 Hz), 4.48 (2H, d, J=6.1 Hz), 6.08 (1H, q, J=4.6 Hz), 6.80 (1H, t, J=6.1 Hz), 6.90 (4H, s), 7.01 (1H, s), 7.75 (1H, s) Anal. Calcd. for C$_{10}$H$_{13}$N$_7$OS$_2$: C 38.57, H 4.21, N 31.49 Found: C 38.37, H 4.04, N 31.17

EXAMPLE 14

A solution of 4-acetylthiazole-2-carboxylic acid ethyl ester (1.5 g) and bromine (1.4 g) in methanol (50 ml) was stirred for 8 hours at room temperature. The solvent was removed under reduced pressure to give 4-bromoacetylthiazole-2-carboxylic acid ethyl ester. A suspension of the above residue and diaminomethylenethiourea (800 mg) in ethanol (50 ml) was refluxed for 4 hours. The resulting precipitate was collected by filtration. Recrystallization from a mixture of methanol and diisopropyl ether afforded 4-[2-(diaminomethyleneamino)thiazol-4-yl]thiazole-2-carboxylic acid ethyl ester hydrobromide (800 mg).

mp: 227° C. (dec.) IR (Nujol): 3400, 3140, 1725, 1680, 1630, 1605 cm$^{-1}$ NMR (DMSO-d$_6$, δ): 1.36 (3H, t, J=7.1 Hz), 4.42 (2H, q, J=7.1 Hz), 7.77 (1H, s), 8.25 (4H, s), 8.75 (1H, s), 12.04 (1H, s) Anal. Calcd. for $C_{10}H_{11}N_5O_2S_2 \cdot HBr$: C 31.75, H 3.20, N 18.51, Br 21.12 Found: C 31.33, H 3.15, N 18.55, Br 21.47

EXAMPLE 15

Bromine (1.3 g) was added slowly to a suspension of 4-acetylthiazole-2-carboxamide (1.3 g) in methanol (50 ml). The mixture was stirred for 3.5 hours at room temperature. The solvent was removed under reduced pressure to give 4-bromoacetylthiazole-2-carboxamide. The above residue and diaminomethylenethiourea (900 mg) were suspended in ethanol (50 ml) and the mixture was refluxed for 24 hours. The resulting precipitate was collected by filtration and suspended in water (50 ml). The mixture was alkalized to pH 11 with a saturated aqueous potassium carbonate solution. The resulting precipitate was collected by filtration. Recrystallization from methanol afforded 4-[2-(diaminomethyleneamino)thiazol-4-yl]thiazole-2-carboxamide (1.05 g).

mp: 265°–266° C. (dec.) IR (Nujol): 3460, 3330, 1670, 1630 cm$^{-1}$ NMR (DMSO-d$_6$, δ): 6.92 (4H, S), 7.19 (1H, s), 7.93 (1H, s), 8.16 (1H, s), 8.17 (1H, s)

EXAMPLE 16

A suspension of 4-[2-(diaminomethyleneamino)-thiazol-4-yl]thiazole-2-carboxamide (1.0 g) in 4N-hydrogenchloride/dioxane (1.0 ml) and methanol (10 ml) was stirred for 1 hour at room temperature. The resulting precipitate was collected by filtration. Recrystallization from water afforded 4-[2-(diaminomethyleneamino)thiazol-4-yl]thiazole-2-carboxamide hydrochloride (850 mg).

mp: >300° C. IR (Nujol): 3350, 3150, 1670, 1600 cm$^{-1}$ NMR (DMSO-d$_6$, δ): 7.69 (1H, s), 7.99 (1H, s), 8.24 (1H, s), 8.38 (4H, s), 8.62 (1H, s), 12.74 (1H, br) Anal. Calcd. for $C_8H_8N_6OS_2 \cdot HCl \cdot H_2O$: C 29.77, H 3.43, N 26.04, Cl 10.98, H$_2$O 5.58 Found: C 29.68, H 3.40, N 25.96, Cl 11.07, H$_2$O 6.20

EXAMPLE 17

A mixture of 2-(acetylaminomethyl)-6-bromoacetylpyridine (50.0 g) and diaminomethylenethiourea (15.3 g) in ethanol (400 ml) was stirred at 40° to 50° C. for 2 hours. The solvent was removed by concentration in vacuo. To the residue was added a mixture of water, ethyl acetate and tetrahydrofuran, and the mixture was adjusted to pH 9.5 with 20% aqueous potassium carbonate. The separated organic layer was washed with brine and dried over magnesium sulfate. Evaporation of the solvent gave a residue, which was purified by column chromatography on silica gel eluting with a mixture of chloroform and methanol (85:15, V/V). The eluted fractions containing the desired product were collected and evaporated in vacuo. The residue was triturated with a mixture of ethyl acetate and diisopropyl ether to give 4-(6-acetylaminomethylpyridin-2-yl)-2-(diaminomethyleneamino)thiazole (18.73 g).

mp: 198°–200° C. IR (Nujol): 1655, 1590, 1545 cm$^{-1}$ NMR (DMSO-d$_6$, δ): 1.93 (3H, s), 4.35 (2H, d, J=6 Hz), 6.90 (4H, br s), 7.14 (1H, t, J=4 Hz), 7.39 (1H, s), 7.76 (1H, d, J=4 Hz), 8.39 (1H, t, J=6 Hz)

EXAMPLE 18

4N-Dioxanic hydrogen chloride (48.0 ml) was added dropwise to a solution of 4-(6-acetylaminomethylpyridin-2-yl)-2-(diaminomethyleneamino)thiazole (18.6 g) in methanol (50 ml) at ambient temperature for 5 minutes. After the mixture was stirred at the same temperature for 30 minutes. To the mixture was added a diisopropyl ether and the isolated precipitate was collected by filtration. The precipitate was recrystallized from a mixture of methanol and diisopropyl ether to give 4-(6-acetylaminomethylpyridin-2-yl)-2-(diaminomethyleneamino)thiazole dihydrochloride (16.29 g).

IR (Nujol): 3340, 3160, 1705, 1650 cm$^{-1}$

EXAMPLE 19

The following compound was obtained according to a similar manner to that of Example 17.

2-(Diaminomethyleneamino)-4-(6-propionylaminomethylpyridin-2-yl)thiazole mp: 216°–217° C. IR (Nujol): 3290, 1642, 1602, 1590, 1530 cm$^{-1}$ NMR (DMSO-d$_6$, δ): 1.06 (3H, t, J=7.6 Hz), 2.22 (2H, q, J=7.6 Hz), 4.38 (2H, d, J=5.9 Hz), 6.94 (4H, s), 7.11–7.19 (1H, m), 7.41 (1H, s), 7.74–7.84 (2H, m), 8.38 (1H, t, J=5.9 Hz) Anal. Calcd. for $C_{13}H_{16}N_6OS$: C 51.30, H 5.30, N 27.61 Found: C 50.99, H 5.19, N 27.32

EXAMPLE 20

Acetoxyacetyl chloride (0.7 g) was added to a mixture of 4-(6-aminomethylpyridin-2-yl)-2-(diaminomethyleneamino)thiazole trihydrochloride (1.5 g) and triethylamine (2.6 ml) in dichloromethane (30 ml) under ice-cooling and the mixture was stirred at ambient temperature for 20 hours. The reaction mixture was added to a mixture of tetrahydrofuran, ethyl acetate and water and the mixture was adjusted to pH 9.5 with 20% aqueous potassium carbonate. The separated organic layer was washed with brine, dried over magnesium sulfate and evaporated in vacuo. The residue was separated and purified by column chromatograpy on silica gel, and eluted with a mixture of chloroform and methanol (9:1, V/V). The eluted fast fractions containing the desired were collected and evaporated in vacuo to give 4-(6-acetoxyacetylaminomethylpyridin-2-yl)-2-[(acetoxyacetylamino)(amino)methyleneamino]thiazole (0.3 g).

mp: 148°–151° C. IR (Nujol): 3380, 1740, 1660, 1630, 1570, 1530 cm$^{-1}$ NMR (DMSO-d$_6$, δ): 2.12 (6H, s), 4.45 (2H, d, J=5.9 Hz), 4.59 (2H, s), 4.70 (2H, s), 7.21 (1H, d, J=7.3 Hz), 7.73 (1H, s), 7.80–7.94 (2H, m), 8.65 (1H, t, J=5.9 Hz)

The eluted another fractions containing the desired product were collected and evaporated in vacuo.

The residue was recrystallized from a mixture of methanol, dioxane and diisopropyl ether to give 4-(6- acetoxyacetylaminomethylpyridin-2-yl)-2-(diaminomethyleneamino)thiazole (0.3 g).

mp: 231° C. (dec.) IR (Nujol): 3390, 1743, 1683, 1660, 1610, 1550 cm$^{-1}$ NMR (DMSO-d$_6$, δ): 2.12 (3H, s), 4.43 (2H, d, J=5.9 Hz), 4.58 (2H, s), 6.93 (4H, s), 7.10–7.20 (1H, m), 7.42 (1H, s), 7.75–7.85 (2H, m), 8.64 (1H, t, J=5.9 Hz) Anal. Calcd. for C$_{14}$H$_{16}$N$_6$O$_3$S: C 48.27, H 4.63, N 24.12 Found: C 48.24, H 4.48, N 24.25

EXAMPLE 21

A mixture of 4-(6-aminomethylpyridin-2-yl)-2-(diaminomethyleneamino)thiazole trihydrochloride (1.5 g), triethylamine (1.8 ml), (furfurylthio)acetic acid (0.8 g), and 1-(3-dimethylaminopropyl)-3-ethylcarbodiimide (1.0 g) in N,N-dimethylformamide (15 ml) was stirred at ambient temperature for 18 hours. The mixture was added to a mixture of ethyl acetate and water and the separated organic layer was dried over magnesium sulfate. Evaporation of the solvent gave a residue, which was purified by column chromatography on silica gel eluting with a mixture of chloroform and methanol (9:1, V/V). The eluted fractions containing the desired product were collected and evaporated in vacuo. The residue was recrystallized from a mixture of methanol, dioxane and diisopropyl ether to give 2-(diaminomethyleneamino)-4-[6-(furfurylthio)acetylaminomethylpyridin-2-yl]thiazole (0.73 g).

mp: 182° C. IR Nujol): 3390, 3300, 1660, 1600 cm$^{-1}$ NMR (DMSO-d$_6$, δ): 3.24 (2H, s), 3.90 (2H, s), 4.41 (2H, d, J=5.7 Hz), 6.28 (1H, d, J=3.1 Hz), 6.38 (1H, dd, J=1.9 Hz, 3.1 Hz), 6.93 (4H, s), 7.17–7.23 (1H, m), 7.43 (1H, s), 7.57–7.58 (1H, m), 7.79–7.85 (2H, m), 8.63 (1H, t, J=5.7 Hz) Anal. Calcd. for C$_{17}$H$_{18}$N$_6$O$_2$S$_2$: C 50.73, H 4.51, N 20.88 Found: C 50.55, H 4.60, N 20.40

EXAMPLE 22

Methyl isocyanate (0.24 ml) was added to a mixture of 4-(6-aminomethylpyridin-2-yl)-2-(diaminomethyleneamino)thiazole trihydrochloride (1.2 g) and triethylamine (1.4 ml) in a solution of tetrahydrofuran (18 ml) and methanol (6 ml) and the mixture was stirred at ambient temperature for 1 hour. To the mixture was added a mixture of ethyl acetate and water, and the mixture was adjusted to pH 9.5 with 20% aqueous potassium carbonate. The separated organic layer was dried over magnesium sulfate and evaporated to give 2-(diaminomethyleneamino)-4-[6-(3-methylureido)methylpyridin-2-yl]thiazole (0.92 g).

mp: 205°–206° C. IR (Nujol): 3320, 1620, 1590 cm$^{-1}$ NMR (DMSO-d$_6$, δ): 2.59 (3H, d, J=4.7 Hz), 4.32 (2H, d, J=5.8 Hz), 6.07 (1H, q, J=4.7 Hz), 6.51 (1H, t, J=5.7 Hz), 6.98 (4H, s), 7.14–7.21 (1H, m), 7.46 (1H, s), 7.77–7.79 (2H, m)

EXAMPLE 23

The following compound was obtained according to a similar manner to that of Example 18.

2-(Diaminomethyleneamino)-4-[6-(3-methylureido)methylpyridin-2-yl]thiazole dihydrochloride mp: 238°–239° C. IR (Nujol): 3310, 1680, 1658, 1590 cm$^{-1}$ NMR (DMSO-d$_6$, δ): 2.62 (3H, s), 4.53 (2H, s), 7.59 (1H, d, J=7.0 Hz), 8.24 (1H, t, J=7.0 Hz), 8.35 (1H, d, J=7.0 Hz), 8.44 (1H, s), 8.50 (4H, s) Anal. Calcd. for C$_{12}$H$_{15}$N$_7$OS.2HCl: C 38.10, H 4.53, N 25.92, Cl 18.74 Found: C 37.95, H 4.35, N 25.62, Cl 18.30

EXAMPLE 24

A mixture of 4-(6-aminomethylpyridin-2-yl)-2-(diaminomethyleneamino)thiazole trihydrochloride (1.7 g), triethylamine (2.0 ml) and 1,1-bis(methylthio)-2-nitroethylene (0.9 g) was stirred at 70° C. for 7 hours. After cooling to ambient temperature, to the mixture was added a 40% aqueous methylamine (2.5 ml) and the mixture was stirred at ambient temperature for 15 hours. The reaction mixture was added to water, and the isolated precipitate was collected by filtration and dried. 4N-Dioxanoic hydrogen chloride (2.2 ml) was added to a mixture of above resulting precipitate in methanol (9.0 ml) and the mixture was stirred at ambient temperature for 1 hour. To the mixture was added a diisopropyl ether (9.0 ml) and the isolated precipitate was collected by filtration. The precipitate was recrystallized from an aqueous ethanol to give 2-(diaminomethyleneamino)-4-[6-[N-(1-methylamino-2-nitrovinyl)aminomethyl]pyridin-2-yl]thiazole (0.47 g).

mp: 184°–185° C. (dec.) IR (Nujol): 3180, 1700, 1635, 1560 cm$^{-1}$ NMR (DMSO-d$_6$+D$_2$O, δ): 2.84 (3H, s), 4.62 (2H, s), 7.37 (1H, d, J=7.5 Hz), 7.95 (1H, t, J=7.5 Hz), 8.00–8.10 (2H, m) Anal. Calcd. for C$_{13}$H$_{16}$N$_8$O$_2$S.1HCl.1.1H$_2$O: C 38.59, H 4.78, N 27.69, Cl 18.76, H20 4.90 Found: C 38.23, H 4.71, N 27.22, Cl 18.47, H$_2$O 4.77

EXAMPLE 25

A mixture of 4-(6-aminomethylpyridin-2-yl)-2-(diaminomethyleneamino)thiazole trihydrochloride (1.5 g), triethylamine (1.8 ml) and dimethyl N-methanesulfonyldithiocarbonimidate (0.8 g) in ethanol (30 ml) was heated under reflux for 5 hours. The solvent was removed by concentration in vacuo. To the residue was added to a mixture of 40% aqueous methylamine (4.0 ml) in N,N-dimethylformamide (13 ml) and the mixture was stirred at ambient temperature for 30 hours. The reaction mixture was added a water and the isolated precipitate was collected by filtration to give 2-(diaminomethyleneamino)-4-[6-(2-methanesulfonyl-3-methylguanidino)methylpyridin-2-yl]thiazole (1.12 g).

mp: 254°–255° C. IR (Nujol): 3425, 3340, 3300, 3230, 1630, 1603, 1575, 1545 cm$^{-1}$ NMR (DMSO-d$_6$, δ): 2.78 (6H, s), 4.50 (2H, d, J=4.7 Hz), 6.92 (4H, s), 7.15–7.21 (2H, m), 7.60 (1H, br s), 7.83–7.89 (2H, m)

EXAMPLE 26

The following compound was obtained according to a similar manner to that of Example 18.

2-(Diaminomethyleneamino)-4-[6-(2-methanesulfonyl-3-methylguanidino)methylpyridin-2-yl]thiazole hydrochloride.

mp: 197° C. IR (Nujol): 3320, 3280, 3230, 3100, 1675, 1650, 1605, 1575, 1550 cm$^{-1}$ NMR (DMSO-d$_6$, δ): 2.79 (6H, s), 4.54 (2H, d, J=4.6 Hz), 7.15–7.35 (1H, m), 7.29 (1H, d, J=7.7 Hz), 7.91 (1H, d, J=7.7 Hz), 8.00–8.20 (1H, m), 8.09 (1H, d, J=7.7 Hz), 8.36 (4H, s), 12.69 (1H, s) Anal. Calcd. for C$_{13}$H$_{18}$N$_8$O$_2$S$_2$.HCl.½H$_2$O: C 36.49, H 4.71, N 26.19, Cl 18.28, H$_2$O 2.10 Found: C 36.23, H 4.63, N 26.11, Cl 18.28, H$_2$O 2.02

EXAMPLE 27

A mixture of 4-(6-aminomethylpyridin-2-yl)-2-(diaminomethyleneamino)thiazole trihydrochloride (3.0 g), triethylamine (3.5 ml) and ethyl ethanesulfonylformimidate (1.5 g) in methanol (60 ml) was stirred at ambient temperature for 6.5 hours and after solvent was removed by concentration in vacuo. To the residue was added a mixture of tetrahydrofuran, ethyl acetate and water and the mixture was adjusted to pH 9.5 with 20% aqueous potassium carbonate. The separated organic layer was washed with brine and dried over magnesium sulfate. Evaporation of the solvent gave a residue, which was purified by column chromatography on silica gel eluting with a mixture of chloroform and methanol (9:1, V/V). The eluted fractions containing the desired product were collected and evaporated in vacuo. The residue was recrystallized from a mixture of methanol, dioxane and diisopropyl ether to give 2-(diaminomethyleneamino)-4-(6-ethanesulfonyliminomethylaminomethylpyridin-2-yl)thiazole (0.88 g).

mp: 201° C. IR (Nujol): 3390, 3270, 1640, 1620, 1545 cm$^{-1}$ NMR (DMSO-d$_6$, δ): 1.10 (3H, t, J=7.3 Hz), 2.92 (2H, q, J=7.3 Hz), 4.59 (2H, d, J=5.4 Hz), 6.94 (4H, s), 7.25 (1H, m), 7.53 (1H, s), 7.84 (2H, d, J=4.5 Hz), 8.15 (1H, d, J=4.9 Hz), 9.19 (1H, m) Anal. Calcd. for C$_{13}$H$_{17}$N$_7$O$_2$S$_2$: C 42.49, H 4.66, N 26.68 Found: C 42.27, H 4.52, N 26.50

EXAMPLE 28

A mixture of 4-(6-aminomethylpyridin-2-yl)-2-(diaminomethyleneamino)thiazole trihydrochloride (1.5 g), triethylamine (1.8 ml) and 1-amino-2-ethoxy-1-cyclobutene-3,4-dione (0.65 g) in methanol (30 ml) was heated under reflux for 7 hours. The solvent was removed by concentration in vacuo. To the residue was added a mixture of water and ethyl acetate, and the mixture was adjusted to pH 1.0 with 6N-hydrochloric acid. The isolated precipitate was collected by filtration and dried. The precipitate was recrystallized from an aqueous N,N-dimethylformamide to give 4-[6-(1-amino-3,4-dioxo-1-cyclobuten-2-yl)aminomethylpyridin-2-yl]-2-(diaminomethyleneamino)thiazole hydrochloride (1.17 g).

mp: 271° C. (dec.) IR (Nujol): 3300, 1695, 1635, 1600 cm$^{-1}$ NMR (DMSO-d$_6$, δ): 4.87 (2H, d, J=6.0 Hz), 7.36 (1H, d, J=7.3 Hz), 7.83 (2H, s), 7.91 (1H, t, J=7.3 Hz), 7.98 (1H, s), 8.06 (1H, d, J=7.3 Hz), 8.27 (4H, s), 8.42 (1H, t, J=6.0 Hz) Anal. Calcd. for C$_{14}$H$_{13}$N$_7$O$_2$S.HCl.2H$_2$O: C 40.44, H 4.36, N 23.58, Cl 8.53, H$_2$O 8.66 Found: C 40.75, H 4.07, N 23.61, Cl 17.99, H$_2$O 8.80

EXAMPLE 29

A mixture of 4-(6-aminomethylpyridin-2-yl)-2-(diaminomethyleneamino)thiazole trihydrochloride (3.0 g), triethylamine (3.5 ml) and diphenyl N-cyanocarbonimidate (2.0 g) in methanol (45 ml) was stirred at ambient temperature for 4 hours. After the solvent was evaporated in vacuo. Acetonitrile (45 ml) and methylhydrazine (2.2 ml) was added to a residue and the mixture was stirred at ambient temperature for 4 hours. The solvent was evaporated in vacuo. To the residue was added a mixture of water and ethyl acetate and the mixture was adjusted to pH 2 with 6N-hydrogen chloride. The separated aqueous layer was adjusted to pH 11 with 4N-sodium hydroxide, the isolated precipitate was collected by filtration and dried to give 4-[6-(3-amino-1-methyl-1H-1,2,4-triazol-5-yl)aminomethylpyridin-2-yl]-2-(diaminomethyleneamino)thiazole (2.71 g).

mp: 260° C. (dec.) IR (Nujol): 3310, 3130, 1605, 1540 cm$^{-1}$ NMR (DMSO-d$_6$, δ): 3.38 (3H, s), 4.47 (2H, d, J=6.0 Hz), 4.80 (2H, s), 6.84 (1H, t, J=6.0 Hz), 6.93 (4H, s), 7.23 (1H, t, J=4.7 Hz), 7.40 (1H, s), 7.73–7.80 (2H, m)

EXAMPLE 30

The following compound was obtained according to a similar manner to that of Example 18.

4-[6-(3-Amino-1-methyl-1H-1,2,4-triazol-5-yl)aminomethylpyridin-2-yl]-2-(diaminomethyleneamino)thiazole dihydrochloride mp: 193° C. (dec.) IR (Nujol): 3300, 3110, 1675, 1650, 1625, 1570 cm$^{-1}$ NMR (DMSO-d$_6$, δ): 3.56 (3H, s), 4.69 (2H, d, J=5.6 Hz), 7.41 (1H, d, J=7.5 Hz), 7.80 (1H, s), 7.90 (1H, t, J=7.5 Hz), 8.10 (1H, d, J=7.5 Hz), 8.44 (4H, s), 8.97 (1H, t, J=5.6 Hz) Anal. Calcd. for C$_{13}$H$_{16}$N$_{10}$S.2HCl: C 37.42, H 4.35, N 33.56, Cl 16.99 Found: C 37.03, H 4.09, N 33.19, Cl 16.74

EXAMPLE 31

A suspension of 4-[(2-acetylamino-1-iminoethylthio)acetyl]-2-(diaminomethyleneamino)thiazole hydrobromide (11.4 g) in ethanol (100 ml) was refluxed for 2.5 hours. The resulting precipitate was collected by filtration and suspended in water (150 ml). The mixture was alkalized to pH 11 with a saturated aqueous potassium carbonate solution. The resulting precipitate was collected by filtration. Recrystallization from water afforded 4-(2-acetylaminomethylthiazol-4-yl )-2-(diaminomethyleneamino)thiazole (6.36 g). IR (Nujol): 3250, 1640 cm$^{-1}$

EXAMPLE 32

The following compound was obtained from 4-bromoacetyl-2-(diaminomethyleneamino)thiazole hydrobromide according to a similar manner to that of the latter of Example 9.

2-(Diaminomethyleneamino)-4-(2-N,N-dimethylaminomethylthiazol-4-yl)thiazole.

mp: 205°–208° C. IR (Nujol): 3410, 3120, 1660, 1610 cm$^{-1}$ NMR (DMSO-d$_6$, δ): 2.29 (6H, s), 3.76 (2H, s), 6.89 (4H, s), 7.01 (1H, s), 7.83 (1H, s)

EXAMPLE 33

A solution of 4N-dioxanic hydrogen chloride (1 ml) was added to a solution of 2-(diaminomethyleneamino)-4-(2-N,N-dimethylaminomethylthiazol-4-yl)thiazole (0.28 g) in methanol (4 ml) and the mixture was stirred at room temperature for 3 hours. The resulting precipitate was collected by filtration. Recrystallization from a mixture of methanol and diisopropyl ether afforded 2-(diaminomethyleneamino)-4-(2-N,N-dimethylaminomethylthiazol-4-yl)thiazole dihydrochloride (0.21 g).

mp: 285°–286° C. (dec.): IR (Nujol): 3420, 3280, 1680, 1610 cm$^{-1}$ NMR (DMSO-d$_6$, δ): 2.85 (6H, s), 4.73 (2H, s), 7.63 (1H, s), 8.30 (4H, s), 8.50 (1H, s) Anal. Calcd. for C$_{10}$H$_{14}$N$_6$S$_2$.2HCl: C 33.80, H 4.54, N 23.65, Cl 19.96 Found: C 33.53, H 4.47, N 23.35, Cl 19.97

EXAMPLE 34

The following compound was obtained from 4-bromoacetyl-2-(diaminomethyleneamino)thiazole according to a similar manner to that of the latter of Example 9.

2-(Diaminomethyleneamino)-4-[2-(3-isopropylureido)methylthiazol-4-yl]thiazole mp: 249° C. (dec.) IR (Nujol): 3420, 3370, 3110, 1630 cm$^{-1}$ NMR (DMSO-d$_6$, δ): 1.06 (6H, d, J=6.5 Hz), 3.78–3.62 (1H, m), 4.48 (2H, ed, J=6.1 Hz), 6.06 (1H, d, J=7.8 Hz), 6.57 (1H, t, J=6.1 Hz), 6.90 (4H, s), 7.01

(1H, s), 7.75 (1H, s) Anal. Calcd. for $C_{12}H_{17}N_7OS_2$: C 42.46, H 5.05, N 28.89 Found: C 42.56, H 4.94, N 29.13

EXAMPLE 35

A suspension of 4-(2-aminomethylthiazol-4-yl)-2-(diaminomethyleneamino)thiazole dihydrochloride (1.6 g), (furfurylthio)acetic acid (0.98 g), 1-(3-dimethylaminopropyl)-3-ethylcarbodiimide hydrochloride (1.2 g) and triethylamine (1.0 g) in N,N-dimethylformamide (20 ml) was stirred with cooling on an ice-water bath for 2.5 hours. The solvent was removed under the reduced pressure. The residue was washed with water and then chromatographed on a silica gel column eluting with a mixture of chloroform and methanol (10:1). The appropriate fractions was collected and the solvent was removed under the reduced pressure. The residue was suspended in water (20 ml) and the mixture was alkalized to pH 11 with a saturated aqueous potassium carbonate solution. The resulting precipitate was collected by filtration. Recrystallization from a mixture of methanol and water afforded 2-(diaminomethyleneamino)-4-[2-(furfurylthio)acetylaminomethylthiazol-4-yl]thiazole (0.22 g).

mp: 204° C. IR (Nujol): 3400, 3180, 1680, 1625, 1605 cm$^{-1}$ NMR (DMSO-d$_6$, δ): 3.20 (2H, s), 3.89 (2H, s), 4.58 (2H, d, J=6.0 Hz), 6.29 (1H, d, J=3.1 Hz), 6.40 (1H, dd, J=1.1 and 3.1 Hz), 6.89 (4H, s), 7.02 (1H, s), 7.59 (1H, d, J=11 Hz), 7.81 (1H, s), 8.95 (1H, t, J=6.0 Hz) Anal. Calcd. for $C_{15}H_{16}N_6O_2S_3$: C 44.10, H 3.95, N 20.57 Found: C 43.85, H 3.93, N 20.31

EXAMPLE 36

A suspension of 4-(2-aminomethylthiazol-4-yl)-2-(diaminomethyleneamino)thiazole dihydrochloride (1.0 g), dimethyl N-cyanodithiocarbonimidate (0.45 g) and triethyl amine (0.7 g) in N,N-dimethylformamide (40 ml) was heated at 70° C. for 10 hours. 40% methylamino solution (5 ml) was added to the reaction mixture and the mixture was stirred at room temperature for 14 hours. The solvent was removed under reduced pressure. The residue was suspended in water (30 ml) and the mixture was alkalized to pH 10 with a saturated aqueous potassium carbonate solution. The resulting precipitate was collected by filtration. Recrystallization from a mixture of N,N-dimethylformamide and water afforded 2-(diaminomethyleneamino)-4-[2-(2-cyano-3-methylguanidino)methylthiazol-4-yl]thiazole (0.2 g).

mp: 244°-250° C. (dec.) IR (Nujol): 3460, 3220, 2140, 1640 cm$^{-1}$ NMR (DMSO-d$_6$, δ): 2.73 (3H, d, J=4.7 Hz), 4.62 (2H, d, J=5.9 Hz), 6.89 (4H, s), 7.02 (1H, s), 7.34 (1H, q, J=4.7 Hz), 7.81 (1H, s), 7.88 (1H, t, J=5.9 Hz) Anal. Calcd. for $C_{11}H_{13}N_9S_2.1.3H_2O$: C 36.82, H 4.38, N 35.13, H$_2$O 6.53
Found: C 37.20, H 4.27, N 34.85, H$_2$O 6.17

EXAMPLE 37

A suspension of 4-(2-aminomethylthiazol-4-yl)-2-(diaminomethyleneamino)thiazole dihydrochloride (1.3 g), ethyl ethanesulfonylformimidate (0.8 g) and triethylamine (1.0 g) in methanol (20 ml) was stirred at room temperature for 8 hours. The solvent was removed under reduced pressure. The residue was chromatographed on a silica gel column eluting with a mixture of chloroform and methanol (10:1). Recrystallization from a mixture of N,N-dimethylformamide and water afforded 2-(diaminomethyleneamino)-4-(2-ethanesulfonyliminomethylaminomethylthiazol-4-yl)thiazole (0.53 g).

mp: 216°-217° C. IR (Nujol): 3420, 3120, 1645, 1605 cm$^{-1}$ NMR (DMSO-d$_6$, δ): 1.11 (3H, t, J=7.3 Hz), 2.95 (2H, q, J=7.3 Hz), 4.78 (2H, s), 6.90 (4H, s), 7.04 (1H, s), 7.87 (1H, s), 8.14 H, s), 9.40 (1H, s) Anal. Calcd for $C_{11}H_{15}N_7O_2S_3$: C 35.38, H 4.05, N 26.25 Found: C 35.42, H 3.98, N 26.31

EXAMPLE 38

The following compound was obtained according to a similar manner to that of Example 18.

4-(6-Aminomethylpyridin-2-yl)-2-(diaminomethyleneamino)thiazole trihydrochloride mp: 288°-289° C. IR (Nujol): 3375, 3275, 3175, 1685 cm$^{-1}$ NMR (DMSO-d$_6$, δ): 4.25 (2H, q, J=5.8 Hz), 6.12 (3H, br s), 7.46 (1H, d, J=7.7 Hz), 7.95 (1H, t, J=7.7 Hz), 8.18 (1H, d, J=7.7 Hz), 8.33 (1H, s), 8.41 (4H, s) and 8.62 (2H, br s) Anal. Calcd. for $C_{10}H_{12}N_6S.3HCl.3H_2O$: C 33.02, H 4.34, N 23.11 Found: C 33.16, H 4.09, N 22.89

EXAMPLE 39

A mixture of 2-(diaminomethyleneamino)-4-(6-propionylaminomethylpyridin-2-yl)thiazole (49.0 g) and conc. hydrochloride acid (134 ml) in ethanol (500 ml) was heated under reflux for 7 hours and after the mixture was cooled to ambient temperature. To the mixture was added ethanol (500 ml) with stirring and the isolated precipitate was collected by filtration to give 4-(6-aminomethylpyridin-2-yl)-2-(diaminomethyleneamino)-thiazole trihydrochloride (52.36 g).

IR (Nujol): 3375, 3275, 3175, 1685 cm$^{-1}$

EXAMPLE 40

A mixture of formic acid (0.47 ml) and acetic anhydride (0.87.ml]was stirred at 40°-50° C. for 30 minutes. To a mixture of 4-(6-aminomethylpyridin-2-yl)-2-(diaminomethyleneamino)thiazole trihydrochloride (3.0 g) and triethylamine (3.5 ml) in N,N-dimethylformamide (45 ml) was added the above mixture under ice-cooling and the mixture was stirred at ambient temperature for 5 hours. The reaction mixture was added to water and the mixture was extracted with a mixture of ethyl acetate and tetrahydrofuran. The extract layer was washed with brine, and dried over magnesium sulfate. Evaporation of a solvent gave a residue, which was Purified by column chromatography on alumina, eluting with a mixture of chloroform and methanol (9:1, V/V). The eluted fractions containing the desired product were collected and evaporated in vacuo. The residue was recrystallized from an aqueous methanol to give 2-(diaminomethyleneamino)-4-(6-formylaminomethylpyridin-2-yl)thiazole (0.62 g).

mp: 192°-193° C. IR (Nujol): 3420, 3350, 1685, 1605, 1590 cm$^{-1}$ NMR (DMSO-d$_6$, δ): 4.43 (2H, d, J=5.9 Hz), 6.93 (4H, s), 7.17-7.23 (1H, m), 7.47 (1H, s), 7.79-7.85 (2H, m), 8.21 (1H, s), 8.63 (1H, m) Anal. Calcd. for $C_{11}H_{12}N_6OS$: C 47.82, H 4.38, N 30.41 Found: C 47.63, H 4.21, N 30.05

EXAMPLE 41

Trifluoroacetic anhydride (2.4 ml) was added to a mixture of 4-(6-aminomethylpyridin-2-yl)-2-(diaminomethyleneamino)thiazole trihydrochloride (3.0 g) and triethylamine (4.7 ml) in N,N-dimethylformamide (60 ml) under ice-cooling, and the mixture was stirred at ambient temperature for 20 hours. The reaction mixture was added to a mixture of tetrahydrofuran, ethyl acetate and water and the mixture was adjusted to pH 9.5 with 20% aqueous potassium carbonate. The separated organic layer was washed with brine, dried over magnesium sulfate and evaporated in vacuo. The residue was recrystallized from a mixture of methanol, dioxane and diisopropyl ether to give 2-(diaminomethyleneamino)-4-(6-trifluroacetylaminomethylpyridine-2-yl)thiazole (0.74 g).

mp: 271° C. (dec.) IR (Nujol): 3430, 3320, 1705, 1650, 1605, 1540 cm$^{-1}$ NMR (DMSO-d$_6$, δ): 4.54 (2H, d, J=5.8 Hz), 6.94 (4H, s), 7.18 (1H, t, J=4.3 Hz), 7.35 (1H, s), 7.83 (2H, d, J=4.3 Hz), 10.05 (1H, t, J=5.8 Hz) Anal. Calcd. for C$_{12}$H$_{11}$N$_6$OSF$_3$: C 41.86, H 3.22, N 24.41 Found: C 41.71, H 3.16, N 24.11

EXAMPLE 42

The following compound was obtained according to a similar manner to that of Example 41.

2-(Diaminomethyleneamino)-4-(6-butyrylaminomethylpyridin-2-yl)thiazole mp: 233°–234° C. IR (Nujol): 3370, 1660, 1610, 1550 cm$^{-1}$ NMR (DMSO-d$_6$, δ): 0.89 (3H, t, J=7.4 Hz), 1.49–1.67 (2H, m), 2.19 (2H, t, J=7.2 Hz), 4.39 (2H, d, J=5.9 Hz), 6.94 (4H, s), 7.17–7.19 (1H, m), 7.41 (1H, s), 7.78–7.84 (2H, m), 8.41 (1H, t, J=5.9 Hz) Anal. Calcd. for C$_{14}$H$_{18}$N$_6$OS: C 52.81, H 5.70, N 26.39 Found: C 52.60, H 5.67, N 26.18

EXAMPLE 43

To a mixture of 4-(6-aminomethylpyridin-2-yl)-2-(diaminomethyleneamino)thiazole trihydrochloride (3.0 g) and triethylamine (4.7 ml) in N,N-dimethylformamide (60 ml) was added a methoxyacetyl chloride (0.9 ml) under ice-cooling and the mixture was stirred for 2.5 hours at the same temperature. The reaction mixture was added to water and the mixture was extracted with a mixture of ethyl acetate and tetrahydrofuran. The extract layer was washed with brine, dried over magnesium sulfate and evaporated in vacuo. The residue was recrystallized from a mixture of methanol, dioxane and diisopropyl ether to give 2-(diaminomethyleneamino)-4-(6-methoxyacetylaminomethylpyridin-2-yl)thiazole (0.86 g).

mp: 195°–196° C. IR (Nujol): 3390, 1665, 1560 cm$^{-1}$ NMR (DMSO-d$_6$, δ): 3.38 (3H, s), 3.93 (2H, s), 4.44 (2H, d, J=5.9 Hz), 6.93 (4H, s), 7.16 (1H, t, J=4.5 Hz), 7.37 (1H, s), 7.79 (2H, d, J=4.5 Hz), 8.44 (1H, t, J=5.9 Hz) Anal. Calcd. for C$_{13}$H$_{16}$N$_6$O$_2$S: C 48.74, H 5.03, N 26.23 Found: C 48.53, H 4.98, N 26.37

EXAMPLE 44

The following compound was obtained according to a similar manner to that of Example 21.

4-(6-Cyclopropylcarbonylaminomethylpyridin-2-yl)-2-(diaminomethyleneamino)thiazole mp: 219° C. IR (Nujol): 3410, 3290, 1645, 1590 cm$^{-1}$ NMR (DMSO-d$_6$, δ): 0.68–0.80 (4H, m), 1.64–1.77 (1H, m), 4.41 (2H, d, J=5.8 Hz), 6.94 (4H, s), 7.16 (1H, t, J=4.7 Hz), 7.43 (1H, s), 7.80 (2H, d, J=4.7 Hz), 8.68 (1H, t, J=5.8 Hz) Anal. Calcd. for C$_{14}$H$_{16}$N$_6$OS: C 53.15, H 5.10, N 26.56 Found: C 52.90, H 5.00, N 26.52

EXAMPLE 45

The following compound was obtained according to a similar manner to that of Example 43.

4-[6-(2-Acetyloxy)propionylaminomethylpyridin-2-yl]-2-(diaminomethyleneamino)thiazole mp: 187° C. IR (Nujol): 3410, 3290, 1730, 1660, 1605 cm$^{-1}$ NMR (DMSO-d$_6$, δ): 1.40 (3H, d, J=6.9 Hz), 2.09 (3H, s), 4.41 (2H, d, J=5.9 Hz), 5.04 (1H, q, J=6.9 Hz), 6.93 (4H, s), 7.10–7.20 (1H, m), 7.40 (1H, s), 7.79 (2H, d, J=5 Hz), 8.65 (1H, t, J=5.9 Hz) Anal. Calcd. for C$_{15}$H$_{18}$N$_6$O$_3$S: C 49.71, H 5.01, N 23.19 Found: C 49.71, H 4.97, N 22.90

EXAMPLE 46

The following compound was obtained according to a similar manner to that of Example 43.

2-(Diaminomethyleneamino)-4-[6-(2-furoyl)aminomethylpyridin-2-yl]thiazole mp: 220°–221° C. (dec.) IR (Nujol): 3390, 3360, 1655, 1615, 1600, 1550 cm$^{-1}$ NMR (DMSO-d$_6$, δ): 4.56 (2H, d, J=6.0 Hz), 6.66 (1H, dd, J=1.8 Hz and 3.4 Hz), 6.97 (4H, s), 7.16–7.21 (2H, m), 7.38 (1H, s), 7.78–7.83 (2H, m), 7.88 (1H, s), 9.00 (1H, t, J=6.0 Hz)

EXAMPLE 47

The following compound was obtained according to a similar manner to that of Example 18.

2-(Diaminomethyleneamino)-4-[6-(2-furyl)aminomethylpyridin-2-yl]thiazole dihydrochloride mp: 157°–158° C. IR (Nujol): 3380, 1690, 1600, 1565 cm$^{-1}$ NMR (DMSO-d$_6$, δ): 4.73 (2H, d, J=5.9 Hz), 6.67 (1H, dd, J=1.8 Hz and 3.5 Hz), 7.26 (1H, d, J=3.5 Hz), 7.48 (1H, d, J=7.8 Hz), 7.91 (1H, s), 8.09 (1H, t, J=7.8 Hz), 8.22 (1H, s), 8.25 (1H, d, J=7.8 Hz), 8.48 (4H, s), 9.24 (1H, t, J=5.9 Hz) Anal. Calcd. for C$_{15}$H$_{14}$N$_6$O$_2$S.2HCl.13/10H$_2$O: C 41.06, H 4.27, N 19.16, Cl 16.16, H$_2$O 5.34 Found: C 41.04, H 4.33, N 19.02, Cl 16.21, H$_2$O 5.06

EXAMPLE 48

The following compound was obtained according to a similar manner to that of Example 21.

2-(Diaminomethyleneamino)-4-(6-nicotinoylaminomethylpyridin-2-yl)thiazole mp: 239° C. (dec.) IR (Nujol): 3350, 1650, 1610, 1590 cm$^{-1}$ NMR (DMSO-d$_6$, δ): 4.64 (2H, d, J=5.7 Hz), 6.94 (4H, s), 7.25 (1H, m), 7.39 (1H, s), 7.55 (1H, dd, J=4.9 Hz and 7.7 Hz), 7.81 (2H, d, J=4.0 Hz), 8.28 (1H, d, J=7.7 Hz), 8.74 (1H, d, J=4.9 Hz), 9.11 (1H, s), 9.36 (1H, t, J=5.7 Hz) Anal. Calcd. for C$_{16}$H$_{15}$N$_7$OS: C 54.38, H 4.28, N 27.74 Found: C 54.31, H 4.29, N 27.41

EXAMPLE 49

The following compound was obtained according to a similar manner to that of Example 43.

2-(Diaminomethyleneamino)-4-[6-(1,1-dioxobenzoisothiazol-3-yl)aminomethylpyridin-2-yl]thiazole mp: 265° C. IR (Nujol): 3330, 1655, 1615, 1590 cm$^{-1}$ NMR (DMSO-d$_6$, δ): 4.83 (2H, d, J=5.5 Hz), 6.93 (4H, s), 7.30–7.34 (1H, m), 7.39 (1H, s), 7.80–7.88 (4H, m), 7.97–8.03 (1H, m), 8.27–8.32 (1H, m), 10.07 (1H, t, J=5.5 Hz)

EXAMPLE 50

The following compound was obtained according to a similar manner to that of Example 18.

2-(Diaminomethyleneamino)-4-[6-(1,1-dioxobenzoisothiazol-3-yl)aminomethylpyridin-2-yl]thiazole hydrochloride mp: 303° C. (dec.) IR (Nujol): 3300, 1690, 1610, 1590 cm$^{-1}$ NMR (DMSO-d$_6$, δ): 4.86 (2H, d, J=5.6 Hz), 7.42 (1H, d, J=7.6 Hz), 7.85–8.03 (5H, m), 8.11 (1H, d, J=7.6 Hz), 8.35 (4H, m), 8.30–8.45 (1H, m), 10.34 (1H, t, J=5.6 Hz), 12.66 (1H, s) Anal. Calcd. for C$_{17}$H$_{15}$N$_{7}$O$_{2}$S$_{2}$.HCl: C 45.38, H 3.58, N 21.79, Cl 7.88 Found: C 45.13, H 3.43, N 21.50, Cl 7.71

EXAMPLE 51

The following compound was obtained according to a similar manner to that of Example 22.

2-(Diaminomethyleneamino)-4-[6-(3-ethylureido)methylpyridin-2-yl]thiazole mp: 219° C. IR (Nujol): 3330, 1630, 1600 cm$^{-1}$ NMR (DMSO-d$_6$, δ): 1.02 (3H, t, J=7.2 Hz), 2.99–3.12 (2H, m), 4.32 (2H, d, J=5.7 Hz), 6.18 (1H, t, J=5.5 Hz), 6.46 (1H, t, J=5.7 Hz), 6.94 (4H, s), 7.14–7.21 (1H, m), 7.46 (1H, s), 7.74–7.83 (2H, m)

EXAMPLE 52

The following compound was obtained according to a similar manner to that of Example 18.

2-(Diaminomethyleneamino)-4-[6-(3-ethylureido)methylpyrdin-2-yl]thiazole dihydrochloride mp: 229° C. IR (Nujol): 3320, 3220, 1685, 1590 cm$^{-1}$ NMR (DMSO-d$_6$, δ): 1.03 (3H, t, J=7.2 Hz), 3.08 (2H, q, J=7.2 Hz), 4.54 (2H, s), 7.59 (1H, d, J=7.1 Hz), 8.25 (1H, t, J=7.1 Hz), 8.36 (1H, d, J=7.1 Hz), 8.45 (1H, s), 8.50 (4H, s) Anal. Calcd. for C$_{13}$H$_{17}$N$_{7}$OS.2HCl: C 39.80, H 4.88, N 24.99, Cl 18.07 Found: C 39.52, H 4.74, N 24.74, Cl 17.92

EXAMPLE 53

The following compound was obtained according to a similar manner to that of Example 18.

4-(6-Acetylaminomethylpyridin-2-yl)-2-(diaminomethyleneamino)thiazole hydrochloride mp: 260° C. (dec.) IR (Nujol): 3330, 3220, 1700, 1610, 1570 cm$^{-1}$ NMR (DMSO-d$_6$, δ): 1.94 (3H, s), 4.40 (2H, d, J=5.9 Hz), 7.26 (1H, d, J=7.5 Hz), 7.86 (1H, t, J=7.5 Hz), 7.93 (1H, s), 8.04 (1H, d, J=7.5 Hz), 8.36 (4H, s), 8.54 (1H, t, J=5.9 Hz), 12.71 (1H, s) Anal. Calcd. for C$_{12}$H$_{14}$N$_{6}$OS.HCl.8/5H$_2$O: C 40.52, H 5.16, N 23.63, Cl 9.97, H$_2$O 8.11 Found: C 40.39, H 5.06, N 23.07, Cl 10.28, H$_2$O 7.85

EXAMPLE 54

The following compound was obtained according to a similar manner to that of Example 12.

4-(6-Acetylaminomethylpyridin-2-yl)-2-(diaminomethyleneamino)thiazole methanesulfonate mp: 242° C. IR (Nujol): 3300, 1700, 1630, 1580 cm$^{-1}$ NMR (DMSO-d$_6$, δ): 1.94 (3H, s), 2.40 (3H, s), 4.39 (2H, d, J=5.9 Hz), 7.26 (1H, d, J=7.3 Hz), 7.86 (1H, t, J=7.3 Hz), 7.93 (1H, s), 8.00 (1H, d, J=7.3 Hz), 8.28 (4H, s), 8.49 (1H, t, J=5.9 Hz), 12.01 (1H, s) Anal. Calcd. for C$_{12}$H$_{14}$N$_{6}$OS.CH$_3$SO$_3$H: C 40.41, H 4.69, N 21.75 Found: C 40.44, H 4.39, N 21.49

EXAMPLE 55

A mixture of 2-(diaminomethyleneamino)-4-[6-[(imino)(methoxy)methyl]pyridin-2-yl]thiazole (0.9 g) in 50% aqueous tetrahydrofuran (60 ml) was adjusted to pH 1.0 with 6N-hydrochloric acid and stirred for 5 minutes at ambient temperature. The mixture was adjusted to pH 9.5 with 20% aqueous potassium carbonate and the mixture was extracted with ethyl acetate. The extract layer was washed with brine, dried over magnesium sulfate and evaporated in vacuo. The residue was recrystallized from a mixture of methanol, dioxane and diisopropyl ether to give 2-(diaminomethyleneamino)-4-(6-methoxycarbonylpyridin-2-yl)thiazole (0.54 g).

mp: 240° C. IR (Nujol): 3440, 3360, 1720, 1650, 1600 cm$^{-1}$ NMR (DMSO-d$_6$, δ): 3.91 (3H, s), 6.94 (4H, s), 7.45 (1H, s), 7.93 (1H, dd, J=1.3 Hz and 7.6 Hz), 8.03 (1H, t, J=7.6 Hz), 8.17 (1H, dd, J=1.3 Hz and J=7.6 Hz) Anal. Calcd. for C$_{11}$H$_{11}$N$_{5}$O$_2$S: C 47.65, H 4.00, N 25.26 Found: C 47.61, H 3.87, N 24.96

EXAMPLE 56

The following compound was obtained according to a similar manner to that of Example 43.

2-(Diaminomethyleneamino)-4-(6-methoxycarbonylaminomethylpyridin-2-yl)thiazole mp: 217° C. IR (Nujol): 3420, 3390, 1705, 1640, 1610 cm$^{-1}$ NMR (DMSO-d$_6$, δ): 3.59 (3H, s), 4.31 (2H, d, J=6.2 Hz), 6.94 (4H, s), 7.13–7.22 (1H, m), 7.39 (1H, s), 7.74–7.85 (3H, m)

EXAMPLE 57

The following compound was obtained according to a similar manner to that of Example 18.

2-(Diaminomethyleneamino)-4-(6-methoxycarbonylaminomethylpyridin-2-yl)thiazole dihydrochloride mp: 188°–189° C. IR (Nujol): 3340, 3210, 1675, 1605 cm$^{-1}$ NMR (DMSO-d$_6$, δ): 3.59 (3H, s), 4.46 (2H, d, J=5.3 Hz), 7.41 (1H, d, J=7.8 Hz), 7.91 (1H, t, J=5.3 Hz), 8.05 (1H, t, J=7.8 Hz), 8.15 (1H, s), 8.20 (1H, d, J=7.8 Hz), 8.44 (4H, s) Anal. Calcd. for C$_{12}$H$_{14}$N$_{6}$O$_2$S.2HCl.1/5H$_2$O: C 37.65, H 4.32, N 21.95, Cl 18.52, H$_2$O 0.94 Found: C 37.72, H 4.34, N 21.97, Cl 18.31, H$_2$O 1.02

EXAMPLE 58

Bromine (0.2 ml) was added dropwise to a mixture of 2-acetyl-6-dimethylaminomethylpyridine (0.7 g) in dioxane (20 ml) and 4N-dioxanichydrogen chloride (2 ml) at ambient temperature with stirring and then the mixture was stirred for 5 hours at 50° C. To the reaction mixture was added a diisopropyl ether (20 ml) at ambient temperature and isolated precipitate was collected by filtration. The resulting mixture was added a mixture of sodium bicarbonate (1.0 g) and diaminomethylenethiourea (0.7 g) in methanol (20 ml) and the mixture was stirred for 2.5 hours at 50°–60° C. The solvent was removed by concentration in vacuo. To the residue was added a mixture of ethyl acetate and water and the mixture was adjusted to pH 12 with 4N-sodium hydroxide. The separated organic layer was washed with brine and dried over magnesium sulfate. The mixture was concentrated and the residue was triturated with a mixture of ethyl acetate and diethyl ether to give 2-(diaminomethyleneamino)-4-(6-dimethylaminomethylpyridin-2-yl)thiazole (0.49 g).

mp: 160°–162° C. IR (Nujol): 3400, 1650, 1590 cm$^{-1}$ NMR (DMSO-d$_6$, δ): 2.22 (6H, s), 3.55 (2H, s), 6.92 (4H, s), 7.29–7.35 (1H, m), 7.35 (1H, s), 7.75–7.84 (2H, m)

EXAMPLE 59

The following compound was obtained according to a similar manner to that of Example 18.

2-(Diaminomethyleneamino)-4-(6-dimethylaminomethylpyridin-2-yl)thiazole trihydrochloride.

mp: 266° C. IR (Nujol): 1680, 1625, 1590 cm$^{-1}$ NMR (DMSO-d$_6$, δ): 2.84 (3H, s), 2.86 (3H, s), 4.54 (2H, d, J=4.9 Hz), 7.54 (1H, d, J=7.8 Hz), 7.99 (1H, t, J=7.8 Hz), 8.24 (1H, d, J=7.8 Hz), 8.36–8.60 (5H, m) Anal. Calcd. for C$_{12}$H$_{16}$N$_{6}$S.3HCl.½H$_2$O: C 36.51, H 5.11, N 21.29, Cl 26.94, H₂O 2.28 Found: C 36.38, H 5.07, N 21.11, Cl 26.81, H₂O 2.30

EXAMPLE 60

The following compound was obtained according to a similar manner to that of Example 17.

4-(6-Carbamoylpyridin-2-yl)-2-(diaminomethyleneamino)thiazole mp: 269° C. IR (Nujol): 3420, 3350, 3250, 1655, 1620 cm$^{-1}$ NMR (DMSO-d₆, δ): 6.96 (4H, s), 7.71 (1H, s), 7.92 (1H, dd, J=1.3 Hz and 7.5 Hz), 8.01 (1H, t, J=7.5 Hz), 8.07 (1H, dd, J=1.3 Hz and 7.5 Hz), 8.44 (1H, s)

EXAMPLE 61

The following compound was obtained according to a similar manner to that of Example 18.

4-(6-Carbamoylpyridin-2-yl)-2-(diaminomethyleneamino)thiazole hydrochloride mp: 310° C. (dec.) IR (Nujol): 3290 (br), 1675, 1610, 1585, 1560 cm$^{-1}$ NMR (DMSO-d₆, δ): 7.79 (1H, s), 8.01 (1H, dd, J=1.4 Hz and 7.7 Hz), 8.09 (1H, t, J=7.7 Hz), 8.28–8.45 (5H, m), 8.58 (2H, s) Anal. Calcd. for C₁₀H₁₀N₆OS.HCl: C 40.20, H 3.71, N 28.13, Cl 11.87 Found: C 40.01, H 3.92, N 27.92, Cl 11.56

EXAMPLE 62

Phosphorus oxychloride (0.7 ml) was dropwise added to a mixture of 4-(6-carbamoylpyridin-2-yl)-2-(diaminomethyleneamino)thiazole (1.0 g) in N,N-dimethylformamide (10 ml) at 2°–8° C. with stirring and the mixture was stirred for 5 hours at the same temperature. The reaction mixture was added to a mixture of tetrahydrofuran, ethyl acetate and water and the mixture was adjusted to pH 9.5 with 20% aqueous potassium carbonate. The separated organic layer was washed with brine and dried over magnesium sulfate. The solvent was removed by concentration and the residue was triturated with a mixture of ethyl acetate and ether to give 4-(6-cyanopyridin-2-yl)-2-(diaminomethyleneamino)thiazole (0.84 g).

mp: >300° C. IR (Nujol) 3450, 3420, 2240, 1650, 1600, 1580 cm$^{-1}$ NMR (DMSO-d₆, δ): 6.95 (4H, s), 7.56 (1H, s), 7.90 (1H, dd, J=1.1 Hz and 7.7 Hz), 8.08 (1H, t, J=7.7 Hz), 8.25 (1H, dd, J=1.1 Hz and 7.7 Hz)

EXAMPLE 63

To a solution of 4-(6-cyanopyridin-2-yl)-2-(diaminomethyleneamino)thiazote (0.7 g) in dry chloroform (7 ml) and dry methanol (14 ml) was bubbled with dry hydrogen chloride for 30 minutes under ice-cooling and the mixture was stirred for 1.5 hours at the same temperature. To the reaction mixture was added diisopropyl ether (20 ml) under stirring and the isolated precipitate was collected by filtration. The Precipitate was made basic to pH 9.5 with an aqueous potassium carbonate under ice-cooling. The mixture was extracted with a mixture of tetrahydrofuran and ethyl acetate. The extract layer was washed with brine and dried over magnesium sulfate. Evaporation of the solvent gave a residue, which was triturated with diisopropyl ether to give 2-(diaminomethyleneamino)-4-[6-(imino)(methoxy)methylpyridin-2-yl]thiazole (0.64 g).

mp: 208°–210° C. IR (Nujol): 3310, 1645, 1600, 1575 cm$^{-1}$ NMR (DMSO-d₆, δ): 3.92 (3H, s), 6.95 (4H, s), 7.70 (1H, dd, J=1.2 Hz and 7.5 Hz), 7.78 (1H, s), 7.99 (1H, t, J=7.5 Hz), 8.07 (1H, dd, J=1.2 Hz and 7.5 Hz)

EXAMPLE 64

A mixture of 2-(diaminomethyleneamino)-4-[6-(imino)(methoxy)methylpyridin-2-yl]thiazole (2.1 g) and sulfamide (2.9 g) in 2-methoxyethanol (10.5 ml) was stirred for 3 hours at 70°–75° C. The mixture was added to water, isolated precipitate was collected by filtration and dried. The precipitate was recrystallized from a mixture of N,N-dimethylformamide and ethyl acetate to give 4-[6-(amino)(aminosulfonylimino)methylpyridin-2-yl]-2-(diaminomethyleneamino)thiazole (1.28 g).

mp: 223°–224° C. (dec.) IR (Nujol): 3440, 3360, 3320, 1630, 1585 cm$^{-1}$ NMR (DMSO-d₆, δ): 6.88 (4H, s), 6.93 (2H, s), 7.70 (1H, s), 7.96–8.08 (3H, m), 8.13 (1H, dd, J=2.6 Hz and 6.5 Hz), 8.98 (1H, s) Anal. Calcd. for C₁₀H₁₂N₈O₂S₂.3/5H₂O: C 34.20, H 3.79, N 31.91, H₂O 3.08 Found: C 34.45, H 3.58, N 31.71, H₂O 3.23

EXAMPLE 65

Bromine (0.64 ml) was added to a mixture of 2-acetyl-6-cyanomethylpyridine (2.0 g) in dioxane (30 ml) and 4N-dioxanichydrogen chloride (3.1 ml) at ambient temperature with stirring, and then the mixture was stirred for 1 hour at 50° C. To the mixture was added the sodium bicarbonate (5.2 g), methanol (30 ml) and diaminomethylenethiourea (2.2 g) at ambient temperature and the mixture was stirred for 2.5 hours at 50° C. The solvent was removed by concentration in vacuo. To the residue was added a mixture of water, tetrahydrofuran and ethyl acetate and the mixture was adjusted to pH 9.5 with potassium carbonate. The separated organic layer was washed with brine, dried over magnesium sulfate and evaporated in vacuo. The residue was triturated with water to give 4-(6-cyanomethylpyridin-2-yl)-2-(diaminomethyleneamino)thiazole (1.5 g).

mp: 216°–217° C. (dec.) IR (Nujol): 3400, 2250, 1655, 1595 cm$^{-1}$ NMR (DMSO-d₆, δ): 4.23 (2H, s), 6.93 (4H, s), 7.26–7.35 (1H, m), 7.40 (1H, s), 7.83–7.91 (2H, m)

EXAMPLE 66

The following compound was obtained according to a similar manner to that of Example 63.

2-(Diaminomethyleneamino)-4-[6-(2-imino-2-methoxyethyl)pyridin-2-yl]thiazole mp: 172°–173° C. IR (Nujol): 3310, 1650, 1590 cm$^{-1}$ NMR (DMSO-d₆, δ): 3.60 (3H, s), 3.74 (2H, s), 6.92 (4H, s), 7.12–7.30 (1H, m), 7.36 (1H, s), 7.75–7.82 (2H, m), 8.13 (1H, s)

EXAMPLE 67

The following compound was obtained according to a similar manner to that of Example 64.

4-[6-[2-Amino-2-(aminosulfonylimino)ethyl]pyridin-2-yl]-2-(diaminomethyleneamino)thiazole mp: 207°–208° C. IR (Nujol): 3420, 3350, 3230, 1650, 1600 cm$^{-1}$ NMR (DMSO-d₆, δ): 3.71 (2H, s), 6.56 (2H, s), 6.92 (4H, s), 7.20–7.30 (1H, m), 7.42 (1H, s), 7.48 (1H, s), 7.75–7.83 (2H, m), 8.42 (1H, s) Anal. Calcd. for C₁₁H₁₄N₈O₂S₂: C 37.28, H 3.98, N 31.62 Found: C 37.03, H 3.97, N 31.33

EXAMPLE 68

The following compound was obtained from 4-bromoacetyl-2-(diaminomethyleneamino)thiazole according to a similar manner to that of the latter of Example 9.

4-[2-(2-t-Butoxycarbonylaminoethyl)thiazol-4-yl]-2-(diaminomethyleneamino)thiazole mp: 197°–198° C. (dec.) IR (Nujol): 3420, 3360, 1670, 1610 cm$^{-1}$ NMR (DMSO-d$_6$, δ): 1.37 (9H, s), 3.10 (2H, t, J=6.8 Hz), 3.29 (2H, m), 6.91 (4H, s), 7.03 (2H, br), 7.76 (1H, s)

EXAMPLE 69

Hydrogen chloride gas was babbled to a solution of 4-[2-(2-t-butoxycarbonylaminoethyl)thiazol-4-yl]-2-diaminomethyleneamino)thiazole (3.0 g) in ethanol (30 ml) for 10 minutes at room temperature. The mixture was stirred at room temperature for 20 minutes. The resulting precipitate was collected by filtration. Recrystallization from a mixture of methanol and diisopropyl ether afforded 4-[2-(2-aminoethyl)thiazol-4-yl]-2-(diaminomethyleneamino)thiazole dihydrochloride (2.3 g).

mp: 284°–286° C. (dec.) IR (Nujol): 3350, 3120, 1680, 1610 cm$^{-1}$ NMR (DMSO-d$_6$, δ): 3.4–3.3 (4H, m), 7.67 (1H, s), 8.17 (4H, s), 8.29 (1H, s), 8.35 (3H, s), 12.69 (1H, s) Anal. Calcd. for C$_9$H$_{12}$N$_6$S$_2$·2HCl: C 31.67, H 4.13, N 24.63, Cl 20.78 Found: C 31.63, H 3.97, N 24.31, Cl 20.92

EXAMPLE 70

A suspension of 4-[2-(2-aminoethyl)thiazol-4-yl]-2-(diaminomethyleneamino)thiazole dihydrochloride (1.0 g), acetyl chloride (230 mg) and triethylamine (1.0 g) in N,N-dimethylformamide (30 ml) was stirred with cooling on an ice-water bath for 1 hour. The solvent was removed under reduced pressure. The residue was suspended in water (30 ml). The mixture was alkalized to pH 11 with a saturated aqueous potassium carbonate solution and then was extracted with ethyl acetate. The extract was dried with magnesium sulfate. The solvent was removed under reduced pressure. The residue was chromatographed on a silica gel column eluting with chloroform:methanol = 10:1. Recrystallization from a mixture of methanol, ethyl acetate and diisopropyl ether afforded 4-[2-(2-acetylaminoethyl)thiazol-4-yl]-2-(diaminomethyleneamino)thiazole (0.33 g).

mp: 226° to 227° C. IR (Nujol): 3420, 3280, 1670, 1620 cm$^{-1}$ NMR (DMSO-d$_6$, δ): 1.81 (3H, s), 3.11 (2H, t, J=6.9 Hz), 3.43–3.37 (2H, m), 6.89 (4H, s), 7.04 (1H, s), 7.76 (1H, s), 8.05 (1H, t, J=5.6 Hz) Anal. Calcd. for C$_{11}$H$_{14}$N$_6$OS$_2$: C 42.56, H 4.55, N 27.08 Found: C 42.66, H 4.39, N 26.89

EXAMPLE 71

The following compound was obtained according to a similar manner to that of Example 11.

2-(Diaminomethyleneamino)-4-[2-(2-ureidoethyl)-thiazol-4-yl]thiazole mp: 205°–208° C. (dec.) IR (Nujol): 3320, 1680, 1650, 1610 cm$^{-1}$ NMR (DMSO-d$_6$, δ): 3.11 (2H, t, J=6.7 Hz), 3.40–3.20 (2H, m), 5.54 (2H, s), 6.15 (1H, t, J=6.0 Hz), 7.59 (1H, s), 8.19 (1H, s), 8.25 (4H, s), 12.40 (1H, s) Anal. Calcd. for C$_{10}$H$_{13}$N$_7$OS$_2$·HCl·H$_2$O: C 32.83, H 4.13, N 26.80, Cl 9.69

Found: C 32.94, H 4.09, N 26.94, Cl 9.53

EXAMPLE 72

The following compound was obtained according to similar manner to that of Example 35.

4-(2-t-Butoxycarbonylaminoacetylaminomethyl-thiazol-4-yl)-2-(diaminomethyleneamino)thiazole mp: 204° C. (dec.) IR (Nujol): 3410, 3350, 3200, 1660, 1640, 1610 cm$^{-1}$ NMR (DMSO-d$_6$, δ): 1.39 (9H, s), 3.61 (2H, d, J=5.9 Hz), 4.57 (2H, d, J=5.9 Hz), 6.91 (4H, s), 7.02 (1H, s), 7.08 (1H, t, J=5.9 Hz), 7.95 (1H, s), 8.72 (1H, t, J=5.9 Hz)

EXAMPLE 73

A solution of hydrogen chloride in dioxane (4N, 5 ml) was added slowly to a suspension of 4-(2-t-butoxycarbonylaminoacetylaminomethylthiazol-4-yl)-2-(diaminomethyleneamino)thiazole·(1.0 g) in methanol (5 ml) with cooling on an ice-water bath. The mixture was stirred for 24 hours with cooling on an ice-water bath. The resulting precipitate was collected by filtration. Recrystallization from a mixture of methanol and diisopropyl ether afforded 4-(2-aminoacetylaminomethylthiazol-4-yl)-2-(diaminomethyleneamino)thiazole dihydrochloride (0.58 g).

mp 275°–277° C. (dec.) IR (Nujol): 3260, 1680, 1660, 1610 cm$^{-1}$ NMR (DMSO-d$_6$, δ): 3.65 (2H, d, J=5.2 Hz), 4.68 (2H, d, J=5.9 Hz), 7.57 (1H, s), 8.23 (3H, br), 8.32 (1H, s), 8.40 (4H, s), 9.41 (1H, t, J=5.9 Hz), 12.76 (1H, s) Anal. Calcd. for C$_{10}$H$_{13}$N$_7$OS$_2$·2HCl·H$_2$O C 29.85, H 4.26, N 24.37, Cl 17.62 Found: C 29.98, H 3.73, N 23.95, Cl 17.62

EXAMPLE 74

The following compound was obtained according to a similar manner to that of Example 15.

4-(2-Cyanothiazol-4-yl)-2-(diaminomethyleneamino)-thiazole mp: >300° C. IR (Nujol): 3460, 3350, 2220, 1640, 1610 cm$^{-1}$ NMR (DMSO-d$_6$, δ): 7.27 (1H, s), 6.93 (4H, s) 8.47 (1H, s)

EXAMPLE 75

To a suspension of 4-(2-cyanothiazol-4-yl)-2-(diaminomethyleneamino)thiazole (1.3 g) in dry-methanol (15 ml) and dry dioxane (15 ml) was suspended with dry hydrogen chloride under ice-cooling and the mixture was stirred for 21 hours at the same temperature. The resulting precipitate was collected by filtration and then poured into a potassium carbonate solution (2.0 g in 20 ml). The resulting precipitate was collected by filtration to afford 2-(diaminomethyleneamino)-4-[2-(imino)(methoxy)methylthiazol-4-yl]thiazole (1.06 g). IR (Nujol): 3430, 3400, 3310, 3110, 1640, 1600 cm$^{-1}$ NMR (DMSO-d$_6$, δ): 3.90 (3H, s), 6.92 (4H, s), 7.22 (1H, s), 8.17 (1H, s), 9.05 (1H, s)

EXAMPLE 76

A suspension of 2-(diaminomethyleneamino)-4-[2-(imino)(methoxy)methylthiazol-4-yl]thiazole (1.0 g) and sulfamide (1.36 g) in a 2-methoxyethanol (10 ml) was heated at 70° C. for 7 hours. The resulting precipitate was removed by filtration. The filtrate was chromatographed on a silica gel column eluting with ethyl acetate:methanol=3:1. Recrystallization from a mixture of N,N-dimethylformamide and water afforded 4-[2-(amino)(aminosulfonylimino)methylthiazol-4-yl]-2-(diaminomethyleneamino)thiazole (0.35 g).

mp: >300° C. IR (Nujol): 3320, 1610 cm$^{-1}$ NMR (DMSO-d$_6$, δ): 6.92 (4H, s), 6.99 (2H, s), 7.26 (1H, s), 7.72 (1H, s), 8.19 (1H, s), 8.77 (1H, s) Anal. Calcd. for C$_8$H$_{10}$N$_8$O$_2$S$_2$·H$_2$O: C 26.70, H 3.22, N 31.13, H$_2$O 3.75 Found: C 27.00, H 3.18, N 30.75, H$_2$O 3.15

EXAMPLE 77

Methanesulfonyl chloride (0.58 ml) was added a mixture of 4-(6-aminomethylpyridin-2-yl)-2-(diaminomethyleneamino)thiazole (1.8 g) and pyridine (0.81 ml) in dichloromethane (40 ml) under ice-cooling and the mixture was stirred for 23 hours at ambient temperature. The reaction mixture was added a mixture of tetrahydrofuran, ethyl acetate and water and the mixture was adjusted to pH 9.5 with 20% aqueous potassium carbonate. The separated organic layer was washed with brine, dried over magnesium sulfate and evaporated. The residue was recrystallized-from an aqueous methanol to give 2-(diaminomethyleneamino)-4-(6-methanesulfonylaminomethylpyridin-2-yl)thiazole (0.4 g).

mp: 196° C. IR (Nujol): 3380, 1640, 1610 cm$^{-1}$ NMR (DMSO-d$_6$, δ): 2.96 (3H, s), 4.31 (2H, s), 6.93 (4H, s), 7.31–7.41 (1H, m), 7.46 (1H, s), 7.66 (1H, s), 7.79–8.89 (2H, m)

EXAMPLE 78

The following compound was obtained according to a similar manner to that of Example 21.

2-(Diaminomethyleneamino)-4-(6-methylthioacetylaminomethylpyridin-2-yl)thiazole mp: 202° C. IR (Nujol): 3400, 1670, 1600 cm$^{-1}$ NMR (DMSO-d$_6$, δ): 2.14 (3H, s), 3.12 (2H, s), 4.42 (2H, d, J=5.8 Hz), 6.92 (4H, s), 7.14–7.23 (1H, m), 7.42 (1H, s), 7.77–7.84 (2H, m), 8.61 (1H, t, J=5.8 Hz)

EXAMPLE 79

A mixture of 4-(6-acetylaminomethylpyridin-2-yl)-2-[(amino)(methylthio)methyleneamino]thiazolehydriodide (2.0 g) and 30 wt % methylamine-methanol solution (2.0 g) in ethanol (40 ml) was refluxed for 27 hours. The solvent was removed by concentration and residue was added to a mixture of tetrahydrofuran, ethyl acetate and water. The mixture was adjusted to pH 9.5 with potassium carbonate and a separated organic layer was washed with brine, dried over magnesium sulfate. Evaporation of a solvent gave a residue, which was purified by column chromatography on silica gel eluting with a mixture of chloroform and methanol (19:1, V/V). The eluted fractions containing the desired product were collected and evaporated in vacuo. The residue was recrystallized from a mixture of methanol, dioxane and diisopropyl ether to give 4-(6-acetylaminomethylpyridin-2-yl)-2-[(amino)(methylamino)methyleneamino]thiazole (0.38 g).

mp: 181° C. IR (Nujol): 3340, 3230, 3130, 1630, 1590 cm$^{-1}$ NMR (DMSO-d$_6$, δ): 1.93 (3H, s), 2.77 (3H, d, J=4.8 Hz), 4.37 (2H, d, J=5.9 Hz), 7.14–7.21 (1H, m), 7.41 (1H, s), 7.46 (2H, s), 7.74–7.84 (2H, m), 8.45 (1H, t, J=5.9 Hz)

EXAMPLE 80

The following compound was obtained according to a similar manner to that of Example 79 excepting using ethylenediamine in place of 30 wt % methylamine-methanol.

4-(6-Acetylaminomethylpyridin-2-yl)-2-(imidazolidin-2-ylideneamino)thiazole mp: 248° C. IR (Nujol): 3300, 1640 cm$^{-1}$ NMR (DMSO-d$_6$, δ): 1.93 (3H, s), 3.55 (4H, s), 4.37 (2H, d, J=5.9 Hz), 7.16 (1H, d, J=7.5 Hz), 7.45 (1H, s), 7.66 (2H, s), 7.78 (1H, t, J=7.5 Hz), 8.01 (1H, d, J=7.5 Hz), 8.44 (1H, t, J=5.9 Hz)

EXAMPLE 81

The following compound was obtained according to a similar manner to that of Example 79 excepting using 2,2,2-trifluoroethylamine in place of 30 wt % methylamine-methanol.

4-(6-Acetylaminomethylpyridin-2-yl)-2-[(amino)-[(2,2,2-trifluoroethyl)amino]methyleneamino]thiazole mp: 233° C. IR (Nujol): 3380, 1650, 1620 cm$^{-1}$ NMR (DMSO-d$_6$, δ): 1.93 (3H, s), 4.04–4.22 (2H, m), 4.38 (2H, d, J=5.9 Hz), 7.10–7.27 (2H, m), 7.52 (1H, s), 7.73–7.88 (4H, m), 8.45 (1H, t, J=5.9 Hz)

EXAMPLE 82

A solution of 4-(6-aminopyridin-2-yl)-2-(diaminomethyleneamino)thiazole dihydrochloride (5.0 g) in water (50 ml) was adjusted to pH 11 with 5N-sodium hydroxide and the mixture was extracted with a mixture of tetrahydrofuran and ethyl acetate. The extract layer was washed with brine, dried over magnesium sulfate and evaporated in vacuo to give 4-(6-aminopyridin-2-yl)-2-(diaminomethyleneamino)thiazole (3.62 g).

mp: 242° C. IR (Nujol): 3330, 1660, 1605 cm$^{-1}$ NMR (DMSO-d$_6$, δ): 5.89 (2H, s), 6.37 (1H, d,. J=7.7 Hz), 6.92 (4H, s), 7.07 (1H, d, J=7.7 Hz), 7.15 (1H, s), 7.41 (1H, t, J=7.7 Hz)

EXAMPLE 83

A mixture of 4-(6-aminopyridin-2-yl)-2-(diaminomethyleneamino)thiazole (0.5 g) and methyl isocyanate (0.15 ml) in tetrahydrofuran (10 ml) was stirred for 30 hours at ambient temperature. Ethyl acetate (15 ml) was added to a reaction mixture and isolated precipitate was collected by filtration to give 2-[(amino)(3-methylureido)methyleneamino]-4-[6-(3-methylureido)-pyridin-2-yl]thiazole (0.19 g). IR (Nujol): 3370, 1670, 1620, 1595 cm$^{-1}$ NMR (DMSO-d$_6$, δ): 2.68 (3H, d, J=4.5 Hz), 2.80 (3H, d, J=4.5 Hz), 6.87 (1H, d, J=4.5 Hz), 7.21 (1H, d, J=7.8 Hz), 7.49 (1H, s), 7.56 (1H, d, J=7.8 Hz), 7.73 (1H, t, J=7.8 Hz), 8.31 (1H, d, J=4.5 Hz), 8.87 (1H, br s), 9.31 (2H, s)

The filtrate was evaporated in vacuo and the residue was triturated with diethyl ether to give 4-(6-aminopyridin-2-yl)-2-[(amino)(3-methylureido)methyleneamino]thiazole (0.35 g). IR (Nujol): 3270 (br), 1610 (br) cm$^{-1}$ NMR (DMSO-d$_6$, δ): 3.68 (3H, d, J=4.5 Hz), 5.91 (2H, s), 6.40 (1H, d, J=7.5 Hz), 7.16 (1H, d, J=7.5 Hz), 7.37 (1H, s), 7.45 (1H, t, J=7.5 Hz), 8.90 (1H, br s), 9.31 (1H, s)

EXAMPLE 84

The following compound was obtained according to a similar manner to that of Example 65.

4-[6-(2-Cyanoethyl)pyridin-2-yl]-2-(diaminomethyleneamino)thiazole mp: 218°–220° C. IR (Nujol): 3430, 3250, 1650, 1595 cm$^{-1}$ NMR (DMSO-d$_6$, δ): 2.93–3.01 (2H, m), 3.05–3.18 (2H, m), 6.95 (4H, m), 7.18–7.26 (1H, m), 7.47 (1H, s), 7.77–7.80 (2H, m)

EXAMPLE 85

A solution of pyridinium dichromate (3.2 g) in N,N-dimethylformamide (10 ml) was added dropwise to a solution of 2-(diaminomethyleneamino)-4-(6-hydroxymethylpyridin-2-yl)thiazole (1.7 g) in N,N-dimethylformamide (17 ml) at −10~−5° C. and the mixture was stirred for 5 hours at the same temperature. The reaction mixture was added to a mixture of ethyl acetate, tetrahydrofuran and water and the mixture was adjusted to pH 10 with potassium carbonate. The separated organic layer was washed with brine, and dried over magnesium sulfate. Evaporation of a solvent gave a residue, which was purified by column chromatography on silica gel eluting with a mixture of chloroform and methanol (9:1, V/V). The eluted fractions containing the desired product were collected and evaporated in vacuo to give 2-(diaminomethyleneamino)-4-(6-formylpyridin-2-yl)thiazole (0.31 g).

mp: 287°–289° C. (dec.) IR (Nujol): 3330 (br), 1700, 1600 cm$^{-1}$ NMR (DMSO-d$_6$, δ): 6.95 (4H, s), 7.56 (1H, s), 7.81 (1H, d, J=7.0 Hz), 8.08 (1H, t, J=7.0 Hz), 8.23 (1H, d, J=7.0 Hz), 10.01 (1H, s)

EXAMPLE 86

A mixture of 4-[6-(2-aminoethyl)pyridin-2-yl]-2-(diaminomethyleneamino)thiazole trihydrochloride (1.5 g) and potassium cyanate (0.5 g) in water (30 ml) was stirred for 5 hours at ambient temperature. The reaction mixture was adjusted to pH 9.5 with potassium carbonate and the mixture was extracted with a mixture of tetrahydrofuran and ethyl acetate. The extract layer was washed with brine, dried over magnesium sulfate and evaporated in vacuo to give 2-(diaminomethyleneamino)-4-[6-(2-ureidoethyl)pyridin-2-yl]thiazole (0.55 g).

IR (Nujol): 3400, 3330, 1640, 1595 cm$^{-1}$ NMR (DMSO-d$_6$, δ): 2.86 (2H, t, J=6.9 Hz), 7.34–7.45 (2H, m), 5.45 (2H, s), 5.96 (1H, t, J=5.7 Hz), 6.93 (4H, s), 7.10–7.13 (1H, m), 7.40 (1H, s), 7.68–7.76 (2H, m)

EXAMPLE 87

The following compound was obtained according to a similar manner to that of Example 98.

2-(Diaminomethyleneamino)-4-[6-(1-methylcyanopropyl)carbonylaminomethylpyridin-2-yl]thiazole. IR (Nujol): 3390, 3330, 1655, 1630 cm$^{-1}$ NMR (DMSO-d$_6$, δ): 0.53–0.60 (2H, m), 0.98–1.06 (2H, m), 1.35 (3H, s), 4.40 (2H, d, J=5.8 Hz), 6.93 (4H, s), 7.07–7.16 (1H, m), 7.37 (1H, s), 7.73–7.84 (2H, m), 8.18 (1H, t, J=5.8 Hz)

EXAMPLE 88

The following compound was obtained according to a similar manner to that of Example 98.

4-(6-Cyclopentylcarbonylaminomethylpyridin-2-yl)-2-(diaminomethyleneamino)thiazole IR (Nujol): 3400, 3300, 1650, 1610 cm$^{-1}$ NMR (DMSO-d$_6$, δ): 1.40–1.95 (8H, m), 2.60–2.75 (1H, m), 4.38 (2H, d, J=5.9 Hz), 6.92 (4H, s), 7.08–7.18 (1H, m), 7.39 (1H, s), 7.73–7.85 (2H, m), 8.38 (1H, t, J=5.9 Hz)

EXAMPLE 89

The following compound was obtained according to a similar manner to that of Example 98.

4-(6-Cyclohexylcarbonylaminomethylpyridin-2-yl)-2-(diaminomethyleneamino)thiazole IR (Nujol): 3410, 3320, 3100, 1645, 1610 cm$^{-1}$ NMR (DMSO-d$_6$, δ): 1.06–1.92 (10H, m), 2.15–2.30 (1H, m), 4.36 (2H, d, J=5.9 Hz), 6.93 (4H, s), 7.05–7.17 (1H, m), 7.39 (1H, s), 7.75–7.81 (2H, m), 8.32 (1H, t, J=5.9 Hz)

EXAMPLE 90

The following compound was obtained according to a similar manner to that of Example 98.

4-(6-Cycloheptylcarbonylaminomethylpyridin-2-yl)-2-(diaminomethyleneamino)thiazole IR (Nujol): 3410, 3320, 1650, 1610 cm$^{-1}$ NMR (DMSO-d$_6$, δ): 1.30–1.95 (12H, m), 2.34–2.50 (1H, m), 4.35 (2H, d, J=5.9 Hz), 6.93 (4H, s), 7.06–7.16 (1H, m), 7.38 (1H, s), 7.73–7.81 (2H, m), 8.31 (1H, t, J=5.9 Hz)

EXAMPLE 91

The following compound was obtained according to a similar manner to that of Example 64.

4-[6-(Amino)(methanesulfonylimino)methylpyridin-2-yl]-2-(diaminomethyleneamino)thiazole mp: 265° C. (dec.) IR (Nujol): 3440, 3330, 1630 cm$^{-1}$ NMR (DMSO-d$_6$, δ): 3.09 (3H, s), 6.94 (4H, s), 8.00–8.10 (2H, m), 8.08 (1H, s), 8.12–8.20 (2H, m), 9.15 (1H, s)

EXAMPLE 92

The following compound was obtained according to a similar manner to that of Example 64.

4-[6-(Amino)(methylaminosulfonylimino)methylpyridin-2-yl]-2-(diaminomethyleneamino)thiazole mp: 210°–211° C. IR (Nujol): 3390, 1655, 1590 cm$^{-1}$ NMR (DMSO-d$_6$, δ): 2.93 (3H, s), 6.95 (4H, s), 7.82–8.10 (3H, m), 7.87 (1H, s)

EXAMPLE 93

A mixture of 2-(diaminomethyleneamino)-4-[6-(imino)(methoxy)methylpyridin-2-yl]thiazole (4.0 g) and cyanamide (1.2 g) in methanol (80 ml) was stirred for 16 hours at ambient temperature. To the mixture was added a diethyl ether (80 ml) and isolated precipitate was collected by filtration. The precipitate was added to a mixture of ethyl acetate and water and adjusted to pH 9.5 with 20% aqueous potassium carbonate. The precipitate was collected by filtration and recrystallized from a mixture of N,N-dimethylformamide and ethyl acetate to give 4-[6-(amino)(cyanoimino)methylpyridin-2-yl]-2-(diaminomethyleneamino)thiazole (3.04 g).

mp: 261° C. (dec.) IR (Nujol): 3380, 2200, 1640, 1555 cm$^{-1}$ NMR (DMSO-d$_6$, δ): 6.96 (4H, s), 8.00–8.04 (2H, m), 8.11–8.19 (2H, m), 9.06 (1H, s), 9.40 (1H, s) Anal. Calcd. for C$_{11}$H$_{10}$N$_8$S.1.5H$_2$O: C 42.17, H 4.18, N 35.76, H$_2$O 8.62 Found: C 42.23, H 4.16, N 36.00, H$_2$O 8.50

EXAMPLE 94

To a solution of 4-[6-(amino)(cyanoimino)methylpyridin-2-yl]-2-(diaminomethyleneamino)thiazole (2.0 g) in a solution of ethanol (60 ml) and chloroform (40 ml) was bubbled with hydrogen chloride for 30 minutes under ice-cooling and the mixture was stirred for 2.5 hours at the same temperature. The solvent was removed by concentration in vacuo. To the residue was added a mixture of tetrahydrofuran, ethyl acetate and water and the mixture was adjusted to pH 9.5 with 20% aqueous potassium carbonate. The separated organic layer was washed with brine, dried over magnesium sulfate and evaporated to-give 4-[6-(amino)(carbamoylimino)methylpyridin-2-yl]-2-(diaminomethyleneamino)thiazole (1.75 g). IR (Nujol): 3430, 1330, 1650 cm$^{-1}$ NMR (DMSO-d$_6$, δ): 6.42 (1H, s), 6.69 (1H, s), 6.94 (4H, s), 7.93–8.02 (2H, m), 8.06–8.15 (2H, m), 8.64 (1H, s), 9.01 (1H, s)

EXAMPLE 95

A mixture of 2-(diaminomethyleneamino)-4-(6-methoxycarbonylpyridin-2-yl)thiazole (4.0 g) and 100% hydrazine monohydrate (1.05 ml) in ethanol (40 ml) was heated under reflux for 8 hours. To the reaction mixture was added ethyl acetate (60 ml) under stirring at ambient temperature. The isolated precipitate was collected by filtration to give 2-(diaminoethyleneamino)-4-(6-hydrazinocarbonylpyridin-2-yl)thiazole (3.19 g).

mp: 233°–234° C. IR (Nujol): 3400, 3300, 1650 (br), 1600 cm$^{-1}$ NMR (DMSO-d$_6$, δ): 6.93 (4H, s), 7.79–8.20 (4H, m), 10.14 (1H, s)

EXAMPLE 96

A mixture of 2-(diaminomethyleneamino)-4-(6-hydrazinocarbonylpyridin-2-yl)thiazole (3.0 g) and 2-methyl-2-thiopseudourea sulfate (1.8 g) in dimethylsulfoxide (30 ml) was stirred for 6 hours at 100° C., and then the mixture was cooled to ambient temperature. To the mixture was added ethyl acetate (30 ml) under stirring. The isolated precipitate was collected by filtration and the precipitate was added to a mixture of water and ethyl acetate. The mixture was adjusted to pH 10 with 4N-sodium hydroxide and precipitate was collected by filtration to give 2-(diaminomethyleneamino)-4-(6-quanidinocarbamoylpyridin-2-yl)thiazole (2.48 g).

mp: 194°–196° C. IR (Nujol): 3330 (br), 1600 (br) cm$^{-1}$ NMR (DMSO-d$_6$+D$_2$O, δ): 7.64 (1H, s), 7.79–7.98,(3H, m)

EXAMPLE 97

A mixture of 2-(diaminomethyleneamino)-4-(6-quanidinocarbamoylpyridin-2-yl)thiazole (2.2 g) in concentrated ammonium hydroxide (22 ml) was heated under reflux for 4 hours and then the mixture was cooled to ambient temperature. To the mixture was added a water (30 ml) and isolated precipitate was collected by filtration to give 4-[6-(5-amino-1H-1,2,4-triazol-3-yl)pyridin-2-yl]-2-(diaminomethyleneamino)-thiazole (1.34 g).

mp: >300° C. IR (Nujol): 3360 (br), 1630 cm$^{-1}$ NMR (DMSO-d$_6$, δ): 5.78 (2H, s), 6.98 (4H, s), 7.71–7.82 (2H, m), 7.90–7.95 (2H, m)

EXAMPLE 98

A mixture of N,N-dimethylglycine hydrochloride (1.5 g), 1-hydroxybenzotriazole hydrate (1.5 g) and 1-(3-dimethylaminopropyl)-3-ethylcarbodiimide hydrochloride (2.1 g) in N,N-dimethylformamide (15 ml) was stirred for 1 hour at ambient temperature. The above mixture was added to a mixture of 4-(6-aminomethyl-pyridin-2-yl)-2-(diaminomethyleneamino)thiazole trihydrochloride (3.0 g) and triethylamine (3.5 ml) in N,N-dimethylformamide (45 ml) and the mixture was stirred for 2 hours at ambient temperature. The solvent was removed by concentration and the residue was dissolved in a mixture of tetrahydrofuran, ethyl acetate and water. The mixture was adjusted to pH 13.5 With 5N-sodium hydroxide. The separated organic layer was washed with brine and evaporated in vacuo. The residue was triturated with ethyl acetate to give 2-(diaminomethyleneamino)-4-(6-dimethylaminoacetylaminomethylpyridin-2-yl)thiazole (1.96 g).

mp: 199° C. IR (Nujol): 3340, 1660, 1600 cm$^{-1}$ NMR (DMSO-d$_6$, δ): 2.27 (6H, s), 2.98 (2H, s), 4.44 (2H, d, J=5.9 Hz), 6.94 (4H, s), 7.12–7.22 (1H, m), 7.37 (1H, s), 7.79 (2H, d, J=4.5 Hz), 8.46 (1H, t, J=5.9 Hz)

EXAMPLE 99

The following compound was obtained according to a similar manner to that of Example 18.

2-(Diaminomethyleneamino)-4-(6-dimethylaminoacetylaminomethylpyridin-2-yl)thiazole trihydrochloride.

mp: 231°–232° C. IR (Nujol): 3270, 3210, 3080, 1680, 1610 cm$^{-1}$ NMR (D$_2$O, δ): 3.06 (6H, s), 4.29 (2H, s), 4.95 (2H, s), 7.85 (1H, d, J=7.7 Hz), 8.28 (1H, d, J=7.7 Hz), 8.28 (1H, s), 8.49 (1H, t, J=7.7 Hz) Anal. Calcd. for C$_{14}$H$_{19}$N$_7$OS.3HCl.H$_2$O: C 36.49, H 5.25, N 21.28, Cl 23.08, H$_2$O 3.91 Found: C 36.22, H 5.10, N 21.05, Cl 23.34, H$_2$O 3.83

EXAMPLE 100

The following compound was obtained according to a similar manner to that of Example 22.

2-(Diaminomethyleneamino)-4-[6-(3-n-propylureido)methylpyridin-2-yl]thiazole mp: 215°–217° C. IR (Nujol): 3400, 3325, 1620, 1590 cm$^{-1}$ NMR (DMSO-d$_6$, δ): 0.85 (3H, t, J=7.4 Hz), 1.31–1.49 (2H, m), 2.94–3.08 (2H, m), 4.33 (2H, d, J=5.7 Hz), 6.20 (1H, t, J=5.7 Hz), 6.43 (1H, t, J=5.7 Hz), 6.94 (4H, s), 7.14–7.21 (1H, m), 7.46 (1H, s), 7.74–7.83 (2H, m)

EXAMPLE 101

The following compound was obtained according to a similar manner to that of Example 18.

2-(Diaminomethyleneamino)-4-[6-(3-n-propylureido)methylpyridin-2-yl]thiazole dihydrochloride mp: 228°–229° C. IR (Nujol): 3360, 3230, 1690, 1610, 1570 cm$^{-1}$ NMR (DMSO-d$_6$, δ): 0.86 (3H, t, J=7.4 Hz), 1.32–1.50 (2H, m), 3.02 (2H, t, J=7.0 Hz), 4.59 (2H, s), 7.65 (1H, d, J=7.0 Hz), 8.30 (1H, t, J=7.0 Hz), 8.40 (1H, t, J=7.0 Hz), 8.55 (5H, s) Anal. Calcd. for C$_{14}$H$_{19}$N$_7$OS.2HCl: C 41.38, H 5.21, N 24.13, Cl 17.45 Found: C 41.36, H 5.12, N 24.22, Cl 17.48

EXAMPLE 102

The following compound was obtained according to a similar manner to that of Example 17.

2-(Diaminomethyleneamino)-4-(6-methoxycarbonyl-pyridin-2-yl)thiazole IR (Nujol): 3440, 3360, 1720, 1650, 1600 cm$^{-1}$

EXAMPLE 103

To a mixture of 2-(diaminomethyleneamino)-4-(6-methoxycarbonylpyridin-2-yl)thiazole (0.7 g) and sodium borohydride (0.3 g) in tetrahydrofuran (10 ml) was added a methanol (1.5 ml) at 50°–55° C. and the mixture was stirred for 1.6 hours at the same temperature. The reaction mixture was added to a mixture of tetrahydrofuran, ethyl acetate and water and the mixture was adjusted to pH 9.5 with 6N-hydrochloric acid. The separated organic layer was washed with brine, dried over magnesium sulfate and evaporated in vacuo to give 2-(diaminomethyleneamino)-4-(6-hydroxymethylpyridin-2-yl)thiazole (0.57 g).

mp: 229° C. IR (Nujol): 3310, 1670, 1600 cm$^{-1}$ NMR (DMSO-d$_6$, δ): 4.60 (2H, s), 5.43 (1H, s), 6.95 (4H, s), 7.34–7.40 (2H, m), 7.75–7.89 (2H, m)

EXAMPLE 104

A mixture of 2-(diaminomethyleneamino)-4-(6-hydroxymethylpyridin-2-yl)thiazole (1.0 g) and thionyl chloride (10 ml) in a mixture of dichloromethane (10 ml) and tetrahydrofuran (10 ml) was stirred for 70 hours at ambient temperature. To the reaction mixture was added a diethyl ether (30 ml) and isolated precipitate was collected by filtration. The precipitate was added to a mixture of tetrahydrofuran, ethyl acetate and water and the mixture was adjusted to pH 9.5 with 20% aqueous potassium carbonate. The separated organic layer was washed with brine, dried over magnesium sulfate and evaporated to give 4-(6-chloromethylpyridin-2-yl)-2-(diaminomethyleneamino)thiazole (0.97 g).

mp: 260°–261° C. IR (Nujol): 3380, 1640, 1600 cm$^{-1}$ NMR (DMSO-d$_6$, δ): 4.79 (2H, s), 6.93 (4H, s), 7.37–7.48 (1H, m), 7.40 (1H, s), 7.83–7.90 (2H, m)

EXAMPLE 105

A mixture of 4-(6-chloromethylpyridin-2-yl)-2-(diaminomethyleneamino)thiazole (1.1 g), 2-mercaptobenzimidazole (0.74 g) and potassium carbonate (0.68 g) in N,N-dimethylformamide (20 ml) was stirred for 15 hours at ambient temperature. The reaction mixture was added water and extracted with ethyl acetate. The extract layer was washed with brine, dried over magnesium sulfate and evaporated to give 4-[6-(benzimidazol-2-yl)-thiomethylpyridin-2-yl]-2-(diaminomethyleneamino)thiazole (1.22 g).

mp: 209°–211° C. IR (Nujol): 3410, 3360, 1650, 1590 cm$^{-1}$ NMR (DMSO-d$_6$, δ): 4.70 (2H, s), 6.92 (4H, s), 7.10–7.18 (3H, m), 7.30 (1H, s), 7.37–7.44 (2H, m), 7.75–7.83 (2H, m)

EXAMPLE 106

The following compound was obtained according to a similar manner to that of Example 18.

4-[6-(Benzimidazol-2-yl)thiomethylpyridin-2-yl]-2-(diaminomethyleneamino)thiazole dihydrochloride.

mp: 272° C. (dec.) IR (Nujol): 3320, 1680, 1620 cm$^{-1}$ NMR (DMSO-d$_6$, δ): 5.04 (2H, s), 7.41–7.56 (4H, m), 7.66–7.75 (2H, m), 7.91 (1H, t, J=7.3 Hz), 8.10 (1H, d, J=7.3 Hz), 8.39 (4H, s) Anal. Calcd. for $C_{17}H_{15}N_7S_2.2HCl..3/5H_2O$: C 43.89, H 3.94, N 21.08, Cl 15.24, H$_2$O 2.32 Found: C 43.69, H 4.00, N 20.93, Cl 15.19, H$_2$O 2.28

EXAMPLE 107

To a solution of 4-(6-cyanomethylpyridin-2-yl)-2-(diaminomethyleneamino)thiazole (1.5 g) in chloroform (7.5 ml) and methanol (7.5 ml) was bubbled with hydrogen chloride for 30 minutes under ice-cooling and the mixture was stirred for 3 hours at the same temperature. To the reaction mixture was added diisopropyl ether (15 ml) under stirring and the isolated precipitate was collected by filtration. The precipitate was dissolved in water (50 ml) and stirred for 5 minutes at ambient temperature. The mixture was adjusted to pH 9.5 with potassium carbonate and extracted with a mixture of tetrahydrofuran and ethyl acetate. The extract layer was washed with brine, dried over magnesium sulfate and evaporated to give 2-(diaminomethyleneamino)-4-(6-methoxycarbonylmethylpyridin-2-yl)thiazole (1.41 g).

mp: 208°–210° C. (dec.) IR (Nujol): 3410, 1730, 1650, 1590 cm$^{-1}$ NMR (DMSO-d$_6$, δ): 3.65 (3H, s), 3.88 (2H, s), 6.93 (4H, s), 7.20–7.29 (1H, m), 7.33 (1H, s), 7.71–7.84 (2H, m)

EXAMPLE 108

To a solution of 2-(diaminomethyleneamino)-4-(6-methoxycarbonylmethylpyridin-2-yl)thiazole (1.3 g) in methanol (30 ml) was bubbled with ammonia for 30 minutes under ice-cooling and the mixture was stirred for 18 hours at ambient temperature. The solvent was removed by concentration in vacuo to give 4-(6-carbamoylmethylpyridin-2-yl)-2-(diaminomethyleneamino)thiazole (1.18 g).

mp: 254° C. IR (Nujol): 3320, 1620, 1590 cm$^{-1}$ NMR (DMSO-d$_6$, δ): 3.61 (2H, s), 6.93 (4H, s), 7.02 (1H, s), 7.18–7.25 (1H, m), 7.35 (1H, s), 7.56 (1H, s), 7.73–7.78 (2H, m)

EXAMPLE 109

The following compound was obtained according to a similar manner to that of Example 18.

4-(6-Carbamoylmethylpyridin-2-yl)-2-(diaminomethyleneamino)thiazole dihydrochloride mp: 250° C. (dec.) IR (Nujol): 3370, 3300, 3120, 1675, 1630, 1600 cm$^{-1}$ NMR (DMSO-d$_6$, δ): 4.03 (2H, s), 7.26 (1H, s), 7.64 (1H, d, J=7.8 Hz), 7.84 (1H, s), 8.24 (1H, t, J=7.8 Hz), 8.36 (1H, d, J=7.8 Hz), 8.41 (1H, s), 8.49 (4H, s) Anal. Calcd. for $C_{11}H_{12}N_6OS.2HCl$: C 37.83, H 4.04, N 24.06, Cl 20.30 Found: C 37.58, H 4.03, N 23.87, Cl 20.43

EXAMPLE 110

The following compound was obtained according to a similar manner to that of Example 17.

4-[6-(2-Acetylaminoethyl)pyridin-2-yl]-2-(diaminomethyleneamino)thiazole mp: 220°–221° C. IR (Nujol): 3400, 3290, 1630, 1595 cm$^{-1}$ NMR (DMSO-d$_6$, δ): 1.80 (3H, s), 2.89 (2H, t, J=7.2 Hz), 3.40–3.51 (2H, m), 6.95 (4H, s), 7.09–7.18 (1H, m), 7.39 (1H, s), 7.68–7.76 (2H, m), 7.94 (1H, t, J=5.4 Hz)

EXAMPLE 111

The following compound was obtained according to a similar manner to that of Example 18.

4-[6-(2-Acetylaminoethyl)pyridin-2-yl]-2-(diaminomethyleneamino)thiazole dihydrochloride mp: 272°–273° C. IR (Nujol): 3350, 3260, 3690, 1590 cm$^{-1}$ NMR (DMSO-d$_6$, δ): 1.78 (3H, s), 3.07 (2H, t, J=6.8 Hz), 3.41–3.55 (2H, m), 7.24 (1H, d, J=7.5 Hz), 8.00–8.10 (2H, m), 8.15–8.22 (2H, m), 8.40 (4H, s) Anal. Calcd. for $C_{13}H_{16}N_6OS.2HCl$: C 41.39, H 4.81, N 22.27, Cl 18.79 Found: C 41.10, H 4.77, N 22.17, Cl 18.58

EXAMPLE 112

The following compound was obtained according to a similar manner to that of Example 39.

4-[6-(2-Aminoethyl)pyridin-2-yl]-2-(diaminomethyleneamino)thiazole trihydrochloride mp: 159°–160° C. IR (Nujol): 3350, 3300, 3220, 1690, 1620, 1595 cm$^{-1}$ NMR (DMSO-d$_6$, δ): 3.20–3.50 (4H, m), 7.59 (1H, d, 7.8 Hz), 8.14 (1H, t, J=7.8 Hz), 8.31 (1H, d, J=7.8 Hz), 8.38 (4H, s), 8.46–8.60 (3H, m) Anal. Calcd. for $C_{11}H_{14}N_6S.3HCl.H_2O$: C 33.90, H 4.91, N 21.56, Cl 27.29, H$_2$O 4.62 Found: C 33.87, H 4.87, N 21.57, Cl 27.07, H$_2$O 4.70

EXAMPLE 113

The following compound was obtained according to a similar manner to that of Example 17.

4-(6-Acetylaminopyridin-2-yl)-2-(diaminomethyleneamino)thiazole mp: 259° C. (dec.) IR (Nujol): 3440, 3350, 3250, 1660, 1640, 1660 cm$^{-1}$ NMR (DMSO-d$_6$, δ): 2.12 (3H, s), 6.93 (4H, s), 7.29 (1H, s), 7.61 (1H, dd, J=0.9 Hz, and 7.9 Hz), 7.79 (1H, t, J=7.9 Hz), 7.96 (1H, dd, J=0.9 Hz and 7.9 Hz), 10.40 (1H, s)

EXAMPLE 114

The following compound was obtained according to a similar manner to that of Example 18.

4-(6-Acetylaminopyridin-2-yl)-2-(diaminomethyleneamino)thiazole dihydrochloride mp: 303° C. IR (Nujol): 3400, 1680, 1615 cm$^{-1}$ NMR (DMSO-d$_6$, δ): 2.18 (3H, s), 7.90–8.06 (4H, m), 8.46 (4H, s), 11.02 (1H, s), 12.98 (1H, br s) Anal. Calcd. for C$_{11}$H$_{12}$N$_6$OS.2HCl.H$_2$O: C 35.98, H 4.39, N 22.88, Cl 19.31, H$_2$O 4.91 Found: C 35.77, H 4.34, N 22.75, Cl 19.50, H$_2$O 4.91

EXAMPLE 115

The following compound was obtained according to a similar manner to that of Example 39.

4-(6-Aminopyridin-2-yl)-2-(diaminomethyleneamino)thiazole dihydrochloride mp: 302° C. (dec.) IR (Nujol): 3370, 3280, 1657, 1610 cm$^{-1}$ NMR (DMSO-d$_6$, δ): 6.98 (1H, d, J=8.8 Hz), 7.54 (1H, d, J=7.7 Hz), 7.96 (1H, dd, J=7.7 Hz and 8.8 Hz), 8.37 (4H, s), 8.44 (1H, s), 8.73 (2H, s) Anal. Calcd. for C$_9$H$_{10}$N$_6$S.2HCl.H2O: C 33.24, H 4.34, N 25.84, Cl 21.80, H$_2$O 5.54 Found: C 33.18, H 4.27, N 26.14, Cl 22.03, H$_2$O 5.79

EXAMPLE 116

The following compound was obtained according to a similar manner to that of Example 17.

4-(4-Acetylaminomethylpyridin-2-yl)-2-(diaminomethyleneamino)thiazole dihydrochloride mp: 222°–224° C. IR (Nujol): 3320, 3240, 1690, 1650 cm$^{-1}$ NMR (DMSO-d$_6$, δ): 4.54 (2H, d, J=5.9 Hz), 7.70 (1H, d, J=6.0 Hz), 8.50 (5H, br s), 8.60 (1H, s), 8.72 (1H, d, J=6.0 Hz), 8.84 (1H, t, J=5.9 Hz) Anal. Calcd. for C$_{12}$H$_{14}$N$_6$OS.2HCl.5/4H$_2$O: C 37.36, H 4.83, N 21.78, Cl 18.38 Found: C 37.25, H 4.47, N 21.43, Cl 18.19

EXAMPLE 117

The following compound was obtained according to a similar manner to that of Example 39.

4-(4-Aminomethylpyridin-2-yl)-2-(diaminomethyleneamino)thiazole trihydrochloride mp: 284°–285° C. IR (Nujol): 3300, 1685 cm$^{-1}$ NMR (DMSO-d$_6$, δ): 4.28 (2H, d, J=5.0 Hz), 7.75 (1H, d, J=5.4 Hz), 8.28 (1H, s), 8.45 (4H, s), 8.75 (1H, d, J=5.4 Hz), 8.76 (1H, s), 9.02 (3H, br s)

EXAMPLE 118

4-(4-Aminomethylpyridin-2-yl)-2-(diaminomethyleneamino)thiazole (1.09 g) was dissolved in water (10 ml) and the solution was adjusted to pH 4 with aqueous sodium hydrogen carbonate. Potassium cyanate (0.25 g) was added to the solution and the mixture was stirred for one hour at ambient temperature. After the pH was readjusted to 4 with 6N-hydrochloric acid, additional potassium cyanate (0.25 g) was added and the mixture was further stirred for 6 hours. The reaction mixture was made basic with aqueous potassium carbonate and the resulting precipitate was collected by filtration. The crude product was chromatographed on silica gel with use of chloroform-methanol (8:2) as eluent and converted to the dihydrochloride in a usual manner. This salt was recrystallized from an aqueous ethanol to give 2-(diaminomethyleneamino)-4-(4-ureidomethylpyridin-2-yl)thiazole dihydrochloride (0.70 g).

mp: 213°–214° C. IR (Nujol): 3450, 3330, 3275, 3175, 3075, 1685 cm$^{-1}$ NMR (DMSO-d$_6$, δ): 4.45 (2H, s), 7.00 (1H, br s), 7.67 (1H, d, J=5.8 Hz), 8.47 (5H, s), 8.53 (1H, s), 8.72 (1H, d, J=5.8 Hz) Anal. Calcd. for C$_{11}$H$_{13}$N$_7$OS.2HCl.H$_2$O: C 34.56, H 4.48, N 25.64, Cl 18.55, H$_2$O 4.71 Found: C 34.62, H 4.40, N 25.35, Cl 18.76, H$_2$O 4.95

EXAMPLE 119

The following compound was obtained according to a similar manner to that of Example 17.

4-(4-Cyanopyridin-2-yl)-2-(diaminomethyleneamino)thiazole hydrobromide mp: >300° C. IR (Nujol): 3440, 3325, 3190, 3070, 2240, 1690 cm$^{-1}$ NMR (DMSO-d$_6$, δ): 7.84 (1H, dd, J=1.5 Hz and 5.0 Hz), 8.09 (1H, s), 8.24 (4H, s), 8.67 (1H, d, J=1.5 Hz), 8.85 (1H, d, J=5.0 Hz) Anal. Calcd. for C$_{10}$H$_8$N$_6$S.HBr: C 36.94, H 2.79, N 25.84, Br 24.57 Found: C 37.13, H 2.72, N 25.61, Br 24.19

EXAMPLE 120

The following compound was obtained according to a similar manner to that of Example 63.

2-(Diaminomethyleneamino)-4-[4-(imino)(methoxy)methylpyridin-2-yl]thiazole mp: 214°–215° C. IR (Nujol): 3450, 3270, 3110, 1650 cm$^{-1}$ NMR (DMSO-d$_6$, δ): 3.85 (3H, s), 6.92.(4H, br s), 7.47 (1H, s), 7.61 (1H, d, J=5.0 Hz), 8.23 (1H, s), 8.60 (1H, d, J=5.0 Hz), 9.59 (1H, s)

EXAMPLE 121

The following compound was obtained according to a similar manner to that of Example 64.

4-[4-(Amino)(aminosulfonylimino)methylpyridin-2-yl]-2-(diaminomethyleneamino)thiazole mp: 234°–235° C. IR (Nujol): 3440, 3330, 1665, 1335, 1145, 1070 cm$^{-1}$ NMR (DMSO-d$_6$, δ): 6.87 (2H, s), 6.96 (4H, s), 7.50 (1H, s), 7.64 (1H, dd, J=1.6 Hz and 5.1 Hz), 7.78 (1H, s), 8.24 (1H, d, J=1.6 Hz), 8.70 (1H, d, J=5.1 Hz), 9.03 (1H, s) Anal. Calcd. for C$_{10}$H$_{12}$N$_8$O$_2$S$_2$ : C 35.29, H 3.55, N 32.92 Found: C 35.68, H 3.49, N 32.54

EXAMPLE 122

1N-Aqueous sodium hydroxide (10 ml) was added to a suspension of 4-(4-cyanopyridin-2-yl)-2-(diaminomethyleneamino)thiazole hydrobromide (1.00 g) in a mixture of methanol (10 ml) and tetrahydrofuran (10 ml). After the mixture was stirred for one day at ambient temperature, the solvent was evaporated in vacuo and the residue was mixed with water (10 ml). The resulting precipitate was collected by filtration, washed with water and recrystallized from a mixture of N,N-dimethylformamide and water to give 4-(4-carbamoylpyridin-2-yl)-2-(diaminomethyleneamino)thiazole (0.45 g).

mp: 169°–171° C. IR (Nujol): 3450, 3330, 3175, 1665 cm$^{-1}$ NMR (DMSO-d$_6$, δ): 6.97 (4H, br s), 7.48 (1H, s), 7.66 (1H, dd, J=1.6 Hz and 5.0 Hz), 7.77 (1H, s), 8.22 (1H, d, J=1.6 Hz), 8.40 (1H, s), 8.69 (1H, d, J=5.0 Hz) Anal. Calcd. for C$_{10}$H$_{10}$N$_6$OS.H$_2$O: C 42.85, H 4.31, N 29.98, H$_2$O 6.43 Found: C 43.05, H 4.23, N 29.72, H$_2$O 6.64

EXAMPLE 123

The following compound was obtained according to a similar manner to that of Example 17.

2-(Diaminomethyleneamino)-4-(2-ethoxycarbonylpyridin-4-yl)thiazole mp: 234°–236° C. IR (Nujol): 3375, 1715 cm$^{-1}$ NMR (DMSO-d$_6$, δ): 1.36 (3H, t, J=7.1 Hz), 4.38 q, J=7.1 Hz), 6.99 (4H, br s), 7.73 (1H, s), 8.04 (1H, dd, J=1.7 Hz and 5.1 Hz), 8.38 (1H, d, J=1.7 Hz), 8.69 (1H, d, J=5.1 Hz)

EXAMPLE 124

The following compound was obtained according to a similar manner to that of Example 103.

2-(Diaminomethyleneamino)-4-(2-hydroxymethylpyridin-4-yl)thiazole mp: 260°–261° C. IR (Nujol): 3400, 3100, 1650 cm$^{-1}$ NMR (DMSO-d$_6$, δ): 4.58 (2H, d, J=5.7 Hz), 5.43 (1H, t, J=5.7 Hz), 6.67 (4H, br s), 7.51 (1H, s), 7.64 (1H, dd, J=1.5 Hz and 5.2 Hz), 7.84 (1H, d, J=1.5 Hz), 8.46 (1H, d, J=5.2 Hz)

EXAMPLE 125

The following compound was obtained according to a similar manner to that of Example 104.

4-(2-Chloromethylpyridin-4-yl)-2-(diaminomethyleneamino)thiazole mp: >93° C. IR (Nujol): 1630 cm$^{-1}$ NMR (DMSO-d$_6$, δ): 4.79 (2H, s), 6.97 (4H, br s), 7.58 (1H, s), 7.76 (1H, dd, J=1.6 Hz and 5.2 Hz), 7.96 (1H, d, J=1.6 Hz), 8.54 (1H, d, J=5.2 Hz)

EXAMPLE 126

Potassium phthalimide (1.65 g) was added to a solution of 4-(2-chloromethylpyridin-4-yl)-2-(diaminomethyleneamino)thiazole (2.39 g) in N,N-dimethylformamide (25 ml). After stirring for 14 hours, the solvent was evaporated in vacuo and the residue was mixed with water. The resulting precipitate was collected by filtration and washed with ethanol and then diisopropyl ether to give 2-(diaminomethyleneamino)-4-(2-phthalimidomethylpyridin-4-yl)thiazole (2.68 g).

mp: 280°–281° C. IR (Nujol): 3425, 1700, 1650 cm$^{-1}$ NMR (DMSO-d$_6$, δ): 4.96 (2H, s), 6.95 (4H, br s), 7.56 (1H, s), 7.68 (1H, d, J=5.1 Hz), 7.85 (1H, s), 7.88–7.96 (4H, m), 8.39 (1H, d, J=5.1 Hz)

EXAMPLE 127

A mixture of 2-(diaminomethyleneamino)-4-(2-phthalimidomethylpyridin-4-yl)thiazole (1.57 g) and hydrazine hydrate (0.63 g) in ethanol (25 ml) was refluxed for two hours. The resulting precipitate was filtered off and washed with methanol (20 ml). The two organic layer was combined and evaporated in vacuo to give 4-(2-aminomethylpyridin-4-yl)-2-(diaminomethyleneamino)thiazole (1.00 g).

mp: >210° C. IR (Nujol): 3300, 3100, 1610 cm$^{-1}$ NMR (DMSO-d$_6$, δ): 3.86 (2H, s), 6.99 (4H, br s), 7.50 (1H, s), 7.65 (1H, dd, J=1.5 Hz and 5.1 Hz), 7.83 (1H, d, J=1.5 Hz), 8.47 (1H, d, J=5.1 Hz)

EXAMPLE 128

The following compound was obtained according to a similar manner to that of Example 2.

4-(2-Acetylaminomethylpyridin-4-yl)-2-(diaminomethyleneamino)thiazole dihydrochloride mp: 246°–248° C. IR (Nujol): 3340, 3250, 1665, 1620 cm$^{-1}$ NMR (DMSO-d$_6$, δ): 1.97 (3H, s), 4.63 (2H, d, J=5.6 Hz), 8.39–8.43 (6H, m), 8.57 (1H, s), 8.78 (1H, d, J=6.0 Hz), 8.86 (1H, t, J=5.6 Hz) Anal. Calcd. for $C_{12}H_{14}N_6OS \cdot 2HCl \cdot H_2O$: C 37.80, H 4.76, N 22.04, Cl 18.60, H$_2$O 4.72 Found: C 37.86, H 4.80, N 22.10, Cl 18.62, H$_2$O 5.01

EXAMPLE 129

The following compound was prepared according to a similar manner to that of Example 126.

4-(4-Chloro-6-phthalimidomethylpyridin-2-yl)-2-(diaminomethyleneamino)thiazole mp: 258°–259° C. IR (Nujol): 3450, 3410, 1765, 1700, 1650 cm$^{-1}$ NMR (DMSO-d$_6$, δ): 4.94 (2H, s), 6.87 (4H, br s), 7.01 (1H, s), 7.48 (1H, d, J=1.7 Hz), 7.86 (1H, d, J=1.7 Hz), 7.89–7.98 (4H, m)

EXAMPLE 130

The following compound was obtained according to a similar manner to that of Example 104.

4-(4-Chloro-6-chloromethylpyridin-2-yl)-2-(diaminomethyleneamino)thiazole mp: >300° C. IR (Nujol): 3430, 1645 cm$^{-1}$ NMR (DMSO-d$_6$, δ): 4.80 (2H, s), 6.91 (4H, br s), 7.49 (1H, s), 7.57 (1H, d, J=1.8 Hz), 7.97 (1H, d, J=1.8 Hz)

EXAMPLE 131

The following compound was obtained according to a similar manner to that of Example 103.

4-(4-Chloro-6-hydroxymethylpyridin-2-yl)-2-(diaminomethyleneamino)thiazole mp: 243°–244° C. IR (Nujol): 3475, 3325, 1665 cm$^{-1}$ NMR (DMSO-d$_6$, δ): 4.59 (2H, d, J=5.7 Hz), 5.57 (1H, t, J=5.7 Hz), 6.90 (4H, br s), 7.40 (1H, d, J=1.9 Hz), 7.45 (1H, s), 7.84 (1H, d, J=1.9 Hz)

EXAMPLE 132

The following compound was obtained according to a similar manner to that of Example 17.

4-(4-Chloro-6-methoxycarbonylpyridin-2-yl)-2-(diaminomethyleneamino)thiazole mp: 258°–259° C. IR (Nujol): 3300, 3070, 1715, 1675 cm$^{-1}$ NMR (DMSO-d$_6$, δ): 3.94 (3H, s), 8.00 (1H, d, J=1.9 Hz), 8.02 (1H, s), 8.33 (4H, s), 8.58 (1H, d, J=1.9 Hz)

EXAMPLE 133

Ammonia gas was bubbled to a suspension of 4-(2-acetoxyacetylaminomethylthiazol-4-yl)-2-(diaminomethyleneamino)thiazole (200 mg) in methanol (20 ml) for 30 minutes with cooling on an ice-water bath. The solvent was removed by filtration. Recrystallization from a mixture of water and methanol afforded 2-(diaminomethyleneamino)-4-(2-hydroxyacetylaminomethylthiazol-4-yl)thiazole (180 mg).

mp: 239° C. IR (Nujol): 3450, 3340, 1630 cm$^{-1}$ NMR (DMSO-d$_6$, δ): 3.91 (2H, d, J=5.8 Hz), 4.59 (2H, d, J=6.2 Hz), 5.63 (1H, t, J=5.8 Hz), 6.89 (4H, s), 7.01 (1H, s), 7.78 (1H, s), 8.68 (1H, t, J=6.2 Hz) Anal. Calcd. for $C_{10}H_{12}N_6O_2S_2$: C 38.45, H 3.87, N 26.90 Found: C 38.43, H 3.84, N 27.06

EXAMPLE 134

A suspension of 4-(2-aminomethylthiazol-4-yl)-2-(diaminomethyleneamino)thiazole (1.0 g), acetoxyacetyl chloride (0.45 g) and triethylamine (0.93 g) in methylenechloride (30 ml) was stirred with cooling on an ice-water bath for 8 hours. The solvent was removed under reduced pressure. The residue was suspended in water (100 ml). The mixture was neutralized with a saturated aqueous sodium bicarbonate solution and then was extracted with a mixture of ethyl acetate (200 ml) and tetrahydrofuran (60 ml). The extract was dried with magnesium sulfate and then was evaporated. The residue was chromatographed on a silica gel column eluting with chloroform:methanol=10:1. Recrystallization from a mixture of methanol and diisopropyl ether afforded 2-(diaminomethyleneamino)-4-2-acetoxyacetylaminomethylthiazol-4-yl)thiazole (0.2 g).

mp: 182°–183° C. IR (Nujol): 3430, 3280, 1745, 1675, 1600 cm$^{-1}$ NMR (DMSO-d$_6$, δ): 2.11 (3H, s), 4.55 (2H, s), 4.59 (2H, d, J=6.1 Hz), 6.89 (4H, s), 7.02 (1H, s), 7.81 (1H, s), 8.95 (1H, t, J=6.1 Hz) Anal. Calcd. for C$_{12}$H$_{14}$N$_6$O$_3$S$_2$: C 40.67, H 3.98, N 23.71 Found: C 40.56, H 4.00, N 23.99

EXAMPLE 135

The following compound was obtained from 4-bromoacetyl-2-(diaminomethyleneamino)thiazole according to a similar manner to that of the latter of Example 9.

4-(2-Cyanomethylthiazol-4-yl)-2-(diaminomethyleneamino)thiazole

IR (Nujol): 3400, 2200, 1650, 1600 cm$^{-1}$ NMR (DMSO-d$_6$, δ): 7.92 (1H, s), 7.07 (1H, s), 6.90 (4H, s), 4.60 (2H, s)

EXAMPLE 136

The following compound was obtained according to a similar manner to that of Example 36.

2-(Diaminomethyleneamino)-4-[2-(2-methanesulfonyl-3-methylguanidino)methylthiazol-4-yl]thiazole mp: 229°–231° C. (dec.) IR (Nujol): 3420, 3350, 1600, 1625 cm$^{-1}$ NMR (DMSO-d$_6$, δ): 2.78 (6H, br), 4.66 (2H, d, J=5.7 Hz), 6.89 (4H, s), 7.02 (1H, s), 7.21 (1H, q, J=4.8 Hz), 7.81 (1H, s), 7.85 (1H, d, J=5.7 Hz)

EXAMPLE 137

4-(6-Acetylaminomethyl-4-chloropyridin-2-yl)-2-(diaminomethyleneamino)thiazole (160 mg) was hydrogenated over 10% palladium on carbon (50% wt) (50 mg) in methanol (5 ml) at atmospheric pressure of hydrogen for 8 hours at ambient temperature. After the catalyst was removed by filtration, the solvent was evaporated in vacuo and the residue was mixed with water. The solution was adjusted to pH 10 with aqueous potassium carbonate and the free base was extracted with ethyl acetate. The extract was washed with water, dried over magnesium sulfate and evaporated in vacuo to give 4-(6-acetylaminomethylpyridin-2-yl)-2-(diaminomethyleneamino)thiazole (0.13 g). IR (Nujol): 1655, 1590, 1545 cm$^{-1}$

EXAMPLE 138

The following compound was obtained according to a similar manner to that of Example 43.

2-(Diaminomethyleneamino)-4-(6-isobutyrylaminomethylpyridin-2-yl)thiazole

NMR (DMSO-d$_6$, δ): 1.07 (6H, d, J=6.8 Hz), 2.43–2.57 (1H, m), 4.36 (2H, d, J=5.9 Hz), 6.92 (4H, br s), 7.09–7.14 (1H, m), 7.39 (1H, s), 7.77–7.80 (1H, m), 8.36 (1H, t, J=5.9 Hz)

EXAMPLE 139

The following compound was obtained according to a similar manner to that of Example 43.

2-(Diaminomethyleneamino)-4-(6-pivaloylaminomethylpyridin-2-yl)thiazole

NMR (DMSO-d$_6$, δ): 1.18 (9H, s), 4.38 (2H, d, J=5.9 Hz), 6.92 (4H, br s), 7.07 (1H, dd, J=5.5 Hz and 5.6 Hz), 7.36 (1H, s), 7.76–7.83 (1H, m), 8.16 (1H, t, J=5.9 Hz)

EXAMPLE 140

The following compound was obtained according to a similar manner to that of Example 43.

2-(Diaminomethyleneamino)-4-(6-methoxycarbonylmethoxyacetylaminomethylpyridin-2-yl)thiazole mp: 200°–201° C. IR (Nujol): 3420, 3175, 1755, 1670 cm$^{-1}$ NMR (DMSO-d$_6$, δ): 3.67 (3H, s), 4.10 (2H, s), 4.30 (2H, s), 4.45 (2H, d, J=5.8 Hz), 6.92 (4H, br s), 7.20 (1H, t, J=4.0 Hz), 7.79 (2H, d, J=4.0 Hz), 8.47 (1H, t, J=5.8 Hz)

EXAMPLE 141

The following compound was obtained according to a similar manner to that of Example 43.

2-(Diaminomethyleneamino)-4-(6-ethoxycarbonylaminomethylpyridin-2-yl)thiazole

NMR (DMSO-d$_6$, δ): 1.19 (3H, t, J=7.1 Hz), 4.04 (2H, q, J=7.1 Hz), 4.30 (2H, d, J=6.2 Hz), 6.92 (4H, br s), 7.16 (1H, dd, J=5.7 Hz and 5.8 Hz), 7.38 (1H, s), 7.71 (1H, t, J=6.2 Hz), 7.79 (1H, d, J=5.8 Hz), 7.80 (1H, d, J=5.7 Hz)

EXAMPLE 142

The following compound was obtained according to a similar manner to that of Example 43.

2-(Diaminomethyleneamino)-4-(6-isobutoxycarbonylaminomethylpyridin-2-yl)thiazole hemi-fumarate mp: 255°–257° C. IR (Nujol): 3320, 1705, 1690 cm$^{-1}$ NMR (DMSO-d$_6$, δ): 0.90 (6H, d, J=6.7 Hz), 1.87 (1H, sept., J=6.7 Hz), 3.78 (2H, d, J=6.7 Hz), 4.30 (2H, d, J=6.2 Hz), 6.62 (1H, s), 7.03 (4H, br s), 7.17 (1H, dd, J=3.3 Hz and 5.5 Hz), 7.40 (1H, s), 7.73–7.81 (3H, m)

EXAMPLE 143

The following compound was obtained according to a similar manner to that of Example 63.

2-(Diaminomethyleneamino)-4-[6-(3-imino-3-methoxypropyl)pyridin-2-yl]thiazole mp: 180°–182° C. IR (Nujol): 3370, 3290, 1650, 1590 cm$^{-1}$ NMR (DMSO-d$_6$, δ): 3.56 (3H, s), 6.93 (4H, s), 7.10–7.23 (1H, m), 7.39 (1H, s), 7.67–7.76 (2H, m), 8.01 (1H, br s)

EXAMPLE 144

The following compound was obtained according to a similar manner to that of Example 64.

4-[6-[3-Amino-3-(aminosulfonylimino)propyl]pyridin-2-yl]-2-(diaminomethyleneamino)thiazole IR (Nujol): 3450, 3340, 1630, 1605cm $^{-1}$ NMR (DMSO-d$_6$, δ): 2.60–2.69 (2H, m), 2.99–3.08 (2H, m), 6.50 (2H, s), 6.93 (4H, s), 7.14–7.25 (1H, m), 7.36 (1H, s), 7.43 (1H, s), 7.71–7.75 (2H, m), 8.32 (1H, s)

EXAMPLE 145

The following compound was obtained according to a similar manner to that of Example 17.

4-(2-Carbamoylpyridin-4-yl)-2-(diaminomethyleneamino)thiazole mp: 276° to 277° C. IR (Nujol): 3410, 1675 cm$^{-1}$ NMR (DMSO-d$_6$, δ): 6.98 (4H, br s), 7.70 (2H, s), 7.98 (1H, dd, J=1.7 Hz and 5.1 Hz), 8.13 (1H, s), 8.36 (1H, d, J=1.7 Hz), 8.61 (1H, d, J=5.1 Hz)

EXAMPLE 146

The following compound was obtained according to a similar manner to that of Example 17.

2-(Diaminomethyleneamino)-4-(5-methoxycarbonypyridin-3-yl)thiazole mp: 248°–249° C. (dec.) IR (Nujol): 3320, 3050, 1720, 1610 cm$^{-1}$ NMR (DMSO-d$_6$, δ): 3.92 (3H, s), 7.00 (4H, s), 7.55 (1H, s), 8.58 (1H, t, J=2.1 Hz), 8.97 (1H, d, J=2.1 Hz), 9.31 (1H, d, J=2.1 Hz) Anal. Calcd. for C$_{11}$H$_{11}$N$_5$O$_2$S: C 47.64, H 4.00, N 25.26 Found: C 47.35, H 3.90, N 25.00

EXAMPLE 147

A suspension of 2-(diaminomethyleneamino)-4-(5-methoxycarbonylpyridin-3-yl)thiazole (500 mg) in 28% ammonia solution (15 ml) and tetrahydrofuran (15 ml) was stirred at room temperature for 9.5 hours. The solvent was removed under reduced pressure. The residue was washed with methanol to afford 4-(5-carbamoylpyridin-3-yl)-2-(diaminomethyleneamino)-thiazole (350 mg).

mp: 262°–263° C. (dec.) IR (Nujol): 3430, 3310, 3190, 1680, 1630, 1600 cm$^{-1}$ NMR (DMSO-d$_6$, δ): 6.93 (4H, s), 7.43 (1H, s), 7.65 (1H, s), 8.25 (1H, s), 8.55 (1H, t, J=2.1 Hz), 8.90 (1H, d, J=2.1 Hz), 9.18 (1H, d, J=2.1 Hz)

EXAMPLE 148

A solution of sodium borohydride (1.2 g) in water (25 ml) was added slowly to a solution of 2-(diaminomethyleneamino)-4-(5-methoxycarbonylpyridin-3-yl)thiazole (2.8 g) in methanol (70 ml) and tetrahydrofuran (70 ml) under refluxing for 20 minutes. The mixture was refluxed for 4 hours. The solvent was removed under reduced pressure and the residue was dissolved in water (100 ml). The mixture was extracted with a mixture of ethyl acetate (300 ml) and tetrahydrofuran (150 ml). The extract was dried with magnesium acetate and then evaporated to afford 2-(diaminomethyleneamino)-4-(5-hydroxymethylpyridin-3-yl)thiazole (1.14 g).

mp: 204°–205° C. (dec) IR (Nujol): 3300, 1650, 1605 cm$^{-1}$ NMR (DMSO-d$_6$, δ): 4.57 (2H, d, J=5.6 Hz), 5.36 (1H, t, J=5.6 Hz), 6.94 (4H, s), 7.33 (1H, s), 8.10 (1H, br), 8.92 (1H, d, J=1.9 Hz), 8.94 (1H, d, J=2.1 Hz)

EXAMPLE 149

The following compound was obtained according to a similar manner to that of Example 104.

4-(5-Chloromethylpyridin-3-yl)-2-(diaminomethyleneamino)thiazole mp: 208°–210° C. (dec.) IR (Nujol): 3470, 3300, 1630 cm$^{-1}$ NMR (DMSO-d$_6$, δ): 4.86 (2H, s), 6.93 (4H, s), 7.40 (1H, s), 8.27 (1H, t, J=2.1 Hz), 8.54 (1H, d, J=2.1 Hz), 9.04 (1H, d, J=2.1 Hz)

EXAMPLE 150

The following compound was obtained according to a similar manner to that of Example 126.

2-(Diaminomethyleneamino)-4-(5-phthalimidomethylpyridin-3-yl)thiazole mp: 237°–239° C. IR (Nujol): 3450, 3310, 1670, 1610 cm$^{-1}$ NMR (DMSO-d$_6$, δ): 4.86 (2H, s), 6.92 (4H, s), 7.35 (1H, s), 7.96–7.83 (4H, m), 8.12 (1H, t, J=2.0 Hz), 8.44 (1H, d, J=2.0 Hz), 8.97 (1H, d, J=2.0 Hz)

EXAMPLE 151

A suspension of 2-(diaminomethyleneamino)-4-(5-phthalimidomethylpyridin-3-yl)thiazole (2.47 g) and hydrazine hydrate (0.4 g) in methanol was stirred at room temperature for 5 hours. 3N hydrochloride solution (40 ml) was added slowly and then the mixture was stirred at room temperature for 1 hour. The solvent was removed under reduced pressure. The residue was suspended in water (30 ml) and then the resulting precipitate was removed by filtration. The solvent was removed under reduced pressure to afford 4-(5-aminomethylpyridin-3-yl)2-(diaminomethyleneamino)thiazole trihydrochloride.

NMR (DMSO-d6, δ): 4.31 (2H, q, J=5.2 Hz), 8.27 (1H, s), 8.44 (4H, s), 8.99 (1H, br), 9.08 (2H, br), 9.52 (1H, br), 9.50 (1H, br)

This compound was dissolved in water (30 ml) and then the mixture was alkalized to pH 11 with a saturated aqueous potassium carbonate solution. The mixture was extracted with a mixture of ethyl acetate (150 ml) and tetrahydrofuran (75 ml). The extract was dried with magnesium sulfate and then evaporated to afford 4-(5-aminomethylpyridine-3-yl)-2-(diaminomethyleneamino)thiazole (1.07 g).

NMR (DMSO-d$_6$, δ): 3.77 (2H, br), 6.87 (2H, br), 6.92 (4H, s), 7.30 (1H, s), 8.13 (1H, t, J=2.1 Hz), 8.41 (1H, d, J=2.1 Hz), 8.90 (1H, d, J=2.1 Hz)

EXAMPLE 152

The following compound was obtained according to a similar manner to that of Example 58.

4-(5-Cyanopyridin-3-yl)-2-(diaminomethyleneamino)thiazole mp: 224°–225° C. (dec.) IR (Nujol): 3400, 2225, 1660, 1610 cm$^{-1}$ NMR (DMSO-d$_6$, δ): 6.89 (4H, s), 7.57 (1H, s), 8.75 (1H, dd, J=1.9 Hz and 2.1 Hz), 8.89 (1H, d, J=1.9 Hz), 9.35 (1H, d, J=2.2 Hz), 9.35 (1H, d, J=2.2 Hz)

EXAMPLE 153

The following compound was obtained according to a similar manner to that of the former of Example 2.

2-(Diaminomethyleneamino)-4-(5-acetylaminomethylpyridin-3-yl)thiazole

IR (Film): 3330, 1630 cm$^{-1}$ NMR (DMSO-d$_6$, δ): 8.94 (1H, d, J=2.1 Hz), 8.42 (1H, t, J=5.8 Hz), 8.37 (1H, d, J=2.1 Hz), 8.04 (1H, t, J=2.1 Hz), 7.32 (1H, s), 6.93 (4H, s), 4.32 (2H, d, J=5.8 Hz), 1.89 (3H, s)

EXAMPLE 154

A mixture of 4-(4-chloro-6-phthalimidomethylpyridin-2-yl)-2-(diaminomethyleneamino)thiazole (1.10 g) and hydrazine mono-hydrate (400 mg) in ethanol (200 ml) was refluxed for 5 hours. After the solvent and excess hydrazine monohydrate were removed by concentration, water (10 ml) was added to the residue and the suspension was adjusted to pH 2 with 6N-hydrochloric acid. The resulting precipitate was filtered off, washed with water (5 ml) and the filtrate and the washing solution were combined. After the solution was readjusted to pH 4 with aqueous sodium bicarbonate, potassium cyanate (320 mg) was added to the solution and the mixture was stirred for 14 hours at ambient temperature. The reaction mixture was readjusted to pH 4 with 6N-hydrochloric acid, additional potassium cyanate (215 mg) was added and the solution was further stirred for 8 hours. The mixture was made basic to pH 10 with aqueous potassium carbonate. The resulting precipitate was collected by filtration, washed with water and recrystallized from a mixture of N,N-dimethylformamide and water to give 4-(4-chloro-6-ureidomethylpyridin-2-yl)-2-(diaminomethyleneamino)thiazole (0.28 g).

mp: >300° C. IR (Nujol): 3410, 3220, 1660, 1640 cm$^{-1}$ NMR (DMSO-d$_6$, δ): 4.29 (2H, d, J=5.9 Hz), 5.74 (2H, s), 6.62 (1H, t, J=5.9 Hz), 7.07 (4H, br s), 7.23 (1H, d, J=1.8 Hz), 7.58 (1H, s), 7.87 (1H, d, J=1.8 Hz) Anal. Calcd. for C$_{11}$H$_{12}$N$_7$ClOS.½H$_2$O: C 39.46, H 3.91, N 29.29, H$_2$O 2.69 Found: C 39.72, H 3.82, N 29.13, H$_2$O 2.69

EXAMPLE 155

The following compound was obtained according to a similar manner to that of Example 154.

4-(6-Acetylaminomethyl-4-chloropyridin-2-yl)-2-(diaminomethyleneamino)thiazole mp: 251°–252° C. IR (Nujol): 3350, 3100, 1660, 1635 cm$^{-1}$ NMR (DMSO-d$_6$, δ): 1.94 (3H, s), 4.36 (2H, d, J=5.9 Hz), 6.89 (4H, br s), 7.23 (1H, d, J=1.9 Hz), 7.49 (1H, s), 7.85 (1H, d, J=1.9 Hz), 8.48 (1H, t, J=5.9 Hz) Anal. Calcd. for C$_{12}$H$_{13}$ClN$_6$OS: C 44.38, H 4.03, N 25.87 Found: C 44.53, H 4.07, N 25.55

EXAMPLE 156

A mixture of cyclobutanecarboxylic acid (0.5 ml), 1-hydroxybenzotriazole hydrate (0.8 g) and 1-(3-dimethylaminopropyl)-3-ethylcarbodiimide hydrochloride (1.0 g) in N,N-dimethylformamide (5 ml) was stirred for 1 hour at ambient temperature. The above mixture was added to a mixture of 4-(6-aminomethylpyridin-2-yl)-2-(diaminomethyleneamino)thiazole trihydrochloride (1.5 g) and triethylamine (1.8 ml) in N,N-dimethylformamide (15 ml) and the mixture was sitrred for 20 hours at ambient temperature. The reaction mixture was added a mixture of ethyl acetate tetrahydrofuran and water and the mixture was adjusted to pH 9.5 with 20% aqueous potassium carbonate. The separated organic layer was washed with brine and dried over magnesium sulfate. The solvent was removed by concentration and the residue was recrystallized from a mixture of N,N-dimethylformamide and ethyl acetate to give 4-(6-cyclobutanecarbonylaminomethylpyridin-2-yl)-2-(diaminomethyleneamino)thiazole (0.86 g).

mp: 242° C. (dec.) IR (Nujol): 3400, 3300, 3110, 1645, 1610 cm$^{-1}$ NMR (DMSO-d$_6$, δ): 1.75–2.29 (6H, m), 3.05–3.22 (1H, m), 4.37 (2H, d, J=5.9 Hz), 6.93 (4H, s), 7.08–7.15 (1H, m), 7.39 (1H, s), 7.76–7.85 (2H, m), 8.28 (1H, t, J=5.9 Hz) Anal. Calcd. for C$_{15}$H$_{18}$N$_6$OS: C 54.53, H 5.49, N 25.44 Found: C 54.40, H 5.50, N 25.24

EXAMPLE 157

The following compound was obtained according to a similar manner to that of Example 156.

2-(Diaminomethyleneamino)-4-[6-(tetrahydrofuran-2-yl)carbonylaminomethylpyridin-2-yl]thiazole mp: 229° C. (dec.) IR (Nujol): 3380, 3340, 1660, 1600 cm$^{-1}$ NMR (DMSO-d$_6$, δ): 1.80–2.20 (3H, m), 2.06–2.24 (1H, m), 3.74–3.88 (1H, m), 3.90–4.02 (1H, m), 4.28–4.37 (1H, m), 4.41 (2H, d, J=5.9 Hz), 6.93 (4H, s), 7.07–7.15 (1H, m), 7.36 (1H, s), 7.76–7.82 (2H, m), 8.45 (1H, t, J=5.9 Hz) Anal. Calcd. for C$_{15}$H$_{18}$N$_6$O$_2$S: C 52.01, H 5.24, N 24.26 Found: C 51.66, H 5.23, N 24.15

EXAMPLE 158.

The following compound was obtained according to a similar manner to that of Example 156.

2-(Diaminomethyleneamino)-4-[6-(tetrahydrofuran-3-yl)carbonylaminomethylpyridin-2-yl]thiazole mp: 227° C. (dec.) IR (Nujol): 3390, 3260, 3130, 1650, 1605 cm$^{-1}$ NMR (DMSO-d$_6$, δ): 1.98–2.10 (2H, m), 2.99–3.15 (1H, m), 3.61–3.82 (3H, m), 3.85–3.95 (1H, m), 4.40 (2H, d, J=5.9 Hz), 6.93 (4H, s), 7.10–7.18 (1H, m), 7.41 (1H, s), 7.77–7.82 (2H, m), 8.56 (1H, t, J=5.9 Hz) Anal. Calcd. for C$_{15}$H$_{18}$N$_6$O$_2$S: C 52.01, H 5.24, N 24.26 Found: C 51.69, H 5.26, N 24.05

EXAMPLE 159

The following compound was obtained according to a similar manner to that of Example 156.

2-(Diaminomethyleneamino)-4-[6-(1-tert-butoxycarbonylpiperidin-3-yl)carbonylaminomethylpyridin-2-yl]thiazole mp: 214°–216° C. IR (Nujol): 3400, 1655, 1610 cm$^{-1}$ NMR (DMSO-d$_6$, δ): 1.15–1.75 (3H, m), 1.40 (9H, s), 1.80–2.00 (1H, m), 2.26–2.47 (1H, m), 2.52–2.96 (2H, m), 3.75–4.10 (2H, m), 4.38 (2H, d, J=5.6 Hz), 6.92 (4H, s), 7.07–7.18 (1H, m), 7.41 (1H, s), 7.75–7.84 (2H, m), 8.53 (1H, t, J=5.6 Hz)

EXAMPLE 160

A mixture of 2-(diaminomethyleneamino)-4-[6-(1-tert-butoxycarbonylpiperidin-3-yl)carbonylaminomethylpyridin-2-yl]thiazole (1.9 g) and 4N-methanolic hydrogen chloride (40 ml) was stirred for 7 hours at ambient temperature. To the reaction mixture was added a tetrahydrofuran (40 ml) and the isolated precipitate was collected by filtration. The precipitate was added to water and adjusted to pH 13 with 5N-sodium hydroxide. The mixture was extracted with a mixture of ethyl acetate and tetrahydrofuran. The extract was washed with brine, dried over magnesium sulfate and evaporated in vacuo. The residue was recrystallized from a mixture of methanol, dioxane and diisopropyl ether to give 2-(diaminomethyleneamino)-4-[6-(3-piperidyl)carbonylaminomethylpyridin-2-yl]thiazole (0.47 g).

mp: 227°–228° C. IR (Nujol): 3300, 3160, 1650, 1620 cm$^{-1}$ NMR (DMSO-d$_6$, δ): 1.23–1.92 (4H, m), 2.22–3.30 (5H, m), 4.37 (2H, J=5.8 Hz), 6.93 (4H, s), 7.06–7.19 (1H, m), 7.39 (1H, s), 7.70–7.86 (2H, m), 8.53 (1H, t, J=5.8 Hz) Anal. Calcd. for C$_{16}$H$_{21}$N$_7$OS: C 53.46, H 5.89, N 27.28 Found: C 53.22, H 5.85, N 26.99

EXAMPLE 161

The following compound was obtained according to a similar manner to that of Example 156.

4-[6-(4-Oxocyclohexyl)carbonylaminomethylpyridin-2-yl]-2-(diaminomethyleneamino)thiazole mp: 232° C. IR (Nujol): 3390, 3390, 1715, 1650, 1605 cm$^{-1}$ NMR (DMSO-d$_6$, δ): 1.73–2.21 (4H, m), 2.21–2.57 (4H, m), 2.66–2.85 (1H, m), 4.41 (2H, d, J=5.8 Hz), 6.94 (4H, m), 7.15 (1H, t, J=4.7 Hz), 7.40 (1H, s), 7.79 (2H, d, J=4.7 Hz), 8.55 (1H, t, J=5.8 Hz)

EXAMPLE 162

The following compound was obtained according to a similar manner to that of Example 156.

2-(Diaminomethyleneamino)-4-[6-[5-(1,2-dithiacyclopentan-3-yl)valeryl]aminomethylpyridin-2-yl]thiazole mp: 204°–205° C. IR (Nujol): 3400, 1645, 1610 cm$^{-1}$ NMR (DMSO-d$_6$, δ): 1.27–1.75 (6H, m), 1.75–1.98 (1H, m), 2.21 (2H, t, J=7.1 Hz), 2.30–2.50 (1H, m), 3.02–3.26 (2H, m), 3.50–3.70 (1H, m), 4.38 (2H, d, J=5.9 Hz), 6.93 (4H, s), 7.15 (1H, t, J=4.4 Hz), 7.40 (1H, s), 7.78 (2H, d, J=4.4 Hz), 8.42 (1H, t, J=5.9 Hz) Anal. Calcd. for C$_{18}$H$_{24}$N$_6$OS$_3$: C 49.52, H 5.54, N 19.25 Found: C 49.40, H 5.53, N 18.99

EXAMPLE 163

A mixture of 4-[3-(1-pyrrolidinyl)methylphenoxy]-butyric acid (1.7 g), diphenylphosphoryl azide (1.4 ml) and triethylamine (0.9 ml) in dry benzene (30 ml) was stirred for 1 hour at 75°–80° C. To the mixture was added a mixture of 4-(6-aminomethylpyridin-2-yl)-2-(diaminomethyleneamino)thiazoletrihydrochloride (1.5 g) and triethylamine (1.8 ml) in a solution of tetrahydrofuran (30 ml) and methanol (30 ml) at ambient temperature and the mixture was stirred for 5 hours at the same temperature. The solvent was removed by concentration and the residue was added a mixture of ethyl acetate, tetrahydrofuran and water. The mixture was adjusted to pH 11 with 4N-sodium hydroxide and the separated organic layer was dried over magnesium sulfate. Evaporation of the solvent gave a residue, which was purified by column chromatography on silica gel eluting with a mixture of chloroform and methanol (4:1, V/V). The eluted fractions containing the desired product were collected and evaporated in vacuo. The residue was recrystallized from a mixture of ethanol and diisopropyl ether to give 2-(diaminomethyleneamino)-4-[[6-[3-[3-(3-pyrrolidinyl)methylphenoxy]propyl]ureido]methyl]thiazole (0.44 g).

mp: 174° C. IR (Nujol): 3350, 3320, 1615 cm$^{-1}$ NMR (DMSO-d$_6$, δ): 1.69 (4H, s), 1.80–1.92 (2H, m), 2.44 (4H, s), 3.12–3.25 (2H, m), 3.55 (2H, s), 3.97 (2H, t, J=6.2 Hz), 4.33 (2H, d, J=5.6 Hz), 6.33 (1H, t, J=5.6 Hz), 6.49 (1H, t, J=5.7 Hz), 6.75–7.08 (7H, m), 7.08–7.26 (2H, m), 7.45 (1H, s), 7.76 (2H, d, J=4.4 Hz) Anal. Calcd. for C$_{25}$H$_{32}$N$_8$O$_2$S·H$_2$O: C 57.02, H 6.51, N 21.28, H$_2$O 3.42 Found: C 56.82, H 6.44, N 21.30, H$_2$O 3.50

EXAMPLE 164

A mixture of 4-(6-acetylaminomethylpyridin-2-yl)-2-[(amino)[2,2,2-trifluoroethyl)amino]methyleneamino]thiazole (3.5 g) and conc. hydrochloric acid (7.8 ml) in ethanol (35 ml) was heated under reflux for 24 hours and then the mixture was cooling to ambient temperature. To the mixture was added ethanol (200 ml) with stirring and the isolated precipitate was collected by filtration to give 4-(6-aminomethylpyridin-2-yl)-2-[(amino)[2,2,2-trifluoroethyl)amino]methyleneamino]thiazole trihydrochloride (3.7 g).

mp: 198°–200° C. IR (Nujol): 3300, 3210, 1675, 1615, 1600 cm$^{-1}$ NMR (D$_2$O, δ): 4.27 (2H, q, J=8.8 Hz), 4.50 (2H, s), 7.58 (1H, d, J=7.5 Hz), 8.00 (1H, d, J=7.8 Hz), 8.04 (1H, s), 8.13 (1H, t, J=7.5 Hz)

EXAMPLE 165

The following compound was obtained according to a similar manner to that of Example 156.

2-[(Amino)(2,2,2-trifluoroethyl)amino]methyleneamino]-4-(6-cycloheptanecarbonylaminomethylpyridin-2-yl)thiazole mp: 229°–230° C. IR (Nujol): 3390, 3360, 1625 cm$^{-1}$ NMR (DMSO-d$_6$-D$_2$O, δ): 1.30–1.92 (12H, m), 2.32–2.50 (1H, m), 4.12 (2H, q, J=9.7 Hz), 4.37 (2H, d, J=5.7 Hz), 7.13 (1H, t, J=4.3 Hz), 7.50 (1H, s), 7.81 (1H, d, J=4.3 Hz), 8.35 (1H, t, J=5.7 Hz) Anal. Calcd. for C$_{20}$H$_{25}$N$_6$OSF$_3$: C 52.85, H 5.54, N 18.49 Found: C 52.98, H 5.68, N 18.18

EXAMPLE 166

A mixture of 4-(6-acetylaminomethylpyridin-2-yl)-2-[(amino)(methylthio)methyleneamino]thiazole hydriodide (1.5 g) and n-butylamine (1.6 ml) in ethanol (30 ml) was heated under reflux for 40 hours. The solvent was removed by concentration and residue was added to a mixture of ethyl acetate, tetrahydrofuran and water. The mixture was adjusted to pH 9.5 with 20% aqueous potassium carbonate and a separated organic layer was washed with brine and dried over magnesium sulfate. Evaporation of a solvent gave a residue, which was purified by column chromatography on silica gel eluting with a mixture of chloroform and methanol (19:1, V/V). The eluted fractions containing the desired product were collected and evaporated in vacuo. The residue was recrystallized from a mixture of methanol, dioxane and diisopropyl ether to give 4-(6-acetylaminomethylpyridin-2-yl)-2-[(amino) (n-butylamino)methyleneamino]thiazole (0.48 g).

mp: 145°–146° C. IR (Nujol): 3380, 1645, 1605 cm$^{-1}$ NMR (DMSO-d$_6$, δ): 0.92 (3H, t, J=7.0 Hz), 1.24–1.60 (4H, m), 1.93 (3H, s), 3.10–3.30 (2H, m), 4.37 (2H, d, J=5.9 Hz), 7.16 (1H, d, J=7.2 Hz), 7.40 (1H, s), 7.66–7.86 (2H, m), 8.45 (1H, t, J=5.9 Hz) Anal. Calcd. for C$_{16}$H$_{22}$N$_6$OS: C 55.47, H 6.40, N 24.26 Found: C 55.25, H 6.48, N 24.03

EXAMPLE 167

The following compound was obtained according to a similar manner to that of Example 166.

4-(6-Acetylaminomethylpyridin-2-yl)-2-[(amino)(cyclohexylamino)methyleneamino]thiazole mp: 127°–128° C. IR (Nujol): 3410, 3270, 1660, 1595 cm$^{-1}$ NMR (DMSO-d$_6$, δ): 1.05–2.00 (10H, m), 1.93 (3H, s), 3.47–3.70 (1H, m), 4.36 (2H, d, J=6.0 Hz), 7.16 (1H, d, J=7.4 Hz), 7.33 (2H, s), 7.40 (1H, s), 7.70 (1H, d, J=7.4 Hz), 7.80 (1H, t, J=7.4 Hz), 8.44 (1H, t, J=6.0 Hz) Anal. Calcd. for C$_{18}$H$_{24}$N$_6$OS: C 58.04, H 6.49, N 22.56 Found: C 58.11, H 6.38, N 22.30

EXAMPLE 168

The following compound was obtained according to a similar manner to that of Example 166.

4-(6-Acetylaminomethylpyridin-2-yl)-2-[(amino)(2-methoxyethylamino)methyleneamino]thiazole mp: 162°–163° C. IR (Nujol): 3370, 1650, 1595 cm$^{-1}$ NMR (DMSO-d$_6$, δ): 1.93 (3H, s), 3.27–3.52 (4H, m), 3.32 (3H, s), 4.37 (2H, d, J=5.9 Hz), 7.10–7.21 (1H, m), 7.42 (1H, s), 7.70–7.85 (2H, m), 8.45 (1H, t, J=5.9 Hz) Anal. Calcd. for C$_{15}$H$_{20}$N$_6$O$_2$S: C 51.71, H 5.79, N 24.12 Found: C 51.37, H 5.79, N 23.84

EXAMPLE 169

The following compound was obtained according to a similar manner to that of Example 166.

4-(6-Acetylaminomethylpyridin-2-yl)-2-[(amino)(2-dimethylaminoethylamino)methyleneamino]thiazole mp: 13°–136° C. IR (Nujol): 3400, 3360, 3100, 1640, 1590 cm$^{-1}$ NMR (DMSO-d$_6$, δ): 1.93 (3H, s), 2.24 (6H, s), 2.40–2.55 (2H, m), 3.24–3.44 (2H, m), 4.36 (2H, d, J=5.9 Hz), 7.16 (1H, d, J=8.0 Hz), 7.40 (1H, s), 7.79 (1H, t, J=8.0 Hz), 7.88 (1H, d, J=8.0 Hz), 8.45 (1H, t, J=5.9 Hz)

EXAMPLE 170

To a solution of 4-(6-acetylaminomethylpyridin-2-yl)-2-[(amino)(2-dimethylaminoethylamino)methyleneamino]thiazole (0.9 g) in methanol (9 ml) was added a 4N-dioxanic hydrogen chloride (2.5 ml) and the mixture was stirred for 30 minutes at ambient temperature. Diisopropyl ether (20 ml) was added to a reaction mixture and isolated precipitate was collected by filtration. The precipitate was recrystallized from a mixture of methanol and diisopropyl ether to give 4-(6-acetylaminomethylpyridin-2-yl)-2-[(amino)(2-dimethylaminoethylamino)ethyleneamino]thiazole trihydrochloride (0.96 g).

mp: 228°–229° C. IR (Nujol): 3190 (br), 1690, 1655, 1605 cm$^{-1}$ NMR (D$_2$O, δ): 2.18 (3H, s), 3.05 (6H, s), 3.60 (2H, t, J=6.2 Hz), 3.99 (2H, t, J=6.2 Hz), 4.82 (2H, s), 7.84 (1H, d, J=7.3 Hz), 8.33 (1H, s), 8.34 (1H, d, J=7.3 Hz), 8.51 (1H, t, J=7.3 Hz) Anal. Calcd. for C$_{16}$H$_{23}$N$_7$OS.3HCl.½H$_2$O: C 40.30, H 5.64, N 20.56, Cl 22.30, H$_2$O 1.26 Found: C 40.36, H 5.65, N 20.79, Cl 22.19, H$_2$O 1.19

EXAMPLE 171

The following compound was obtained according to a similar manner to that of Example 166.

4-(6-Acetylaminomethylpyridin-2-yl)-2-[bis(methylamino)methyleneamino]thiazole mp: 277°–279° C. IR (Nujol): 3360, 1665, 1590 cm$^{-1}$ NMR (DMSO-d$_6$, δ): 1.93 (3H, s), 2.83 (6H, d, J=4.5 Hz), 4.37 (2H, d, J=5.9 Hz), 7.12–7.20 (1H, m), 7.42 (1H, s), 7.75–7.82 (2H, m), 8.45 (1H, t, J=5.9 Hz) Anal. Calcd. for C$_{14}$H$_{18}$N$_6$OS: C 52.81, H 5.70, N 26.39 Found: C 52.50, H 5.64, N 26.10

EXAMPLE 172

The following compound was obtained according to a similar manner to that of Example 166.

4-(6-Acetylaminomethylpyridin-2-yl)-2-[(amino)(ethylamino)methyleneamino]thiazole NMR (DMSO-d$_6$, δ): 1.13 (3H, t, J=7.1Hz), 1.93 (3H, s), 3.14–3.30 (2H, m), 4.37 (2H, d, J=5.9 Hz), 7.16 (1H, dd, J=1.2 Hz and 7.2 Hz), 7.41 (3H, s), 7.73 (1H, d, J=7.2 Hz), 7.80 (1H, t, J=7.2 Hz), 8.45 (1H, t, J=5.9 Hz)

EXAMPLE 173

The following compound was obtained according to a similar manner to that of Example 166.

4-(6-Acetylaminomethylpyridin-2-yl)-2-[(amino)-(n-propylamino)methyleneamino]thiazole NMR (DMSO-d$_6$, δ): 0.93 (3H, t, J=7.3 Hz), 1.41–1.64 (2H, m), 1.93 (3H, s), 3.09–3.22 (2H, m), 4.37 (2H, d, J=5.9 Hz), 7.17 (1H, d, J=7.3 Hz), 7.41 (3H, s), 7.73 (1H, d, J=7.3 Hz), 7.80 (1H, t, J=7.3 Hz), 8.45 (1H, t, J=5.9 Hz)

EXAMPLE 174

The following compound was obtained according to a similar manner to that of Example 166.

4-(6-Acetylaminomethylpyridin-2-yl)-2-[(amino)-(n-pentylamino)methyleneamino]thiazole NMR (DMSO-d$_6$, δ): 0.89 (3H, t, J=6.5 Hz), 1.10–1.70 (6H, m), 1.94 (3H, s), 3.03–3.31 (2H, m), 4.38 (2H, d, J=5.9 Hz), 7.17 (1H, d, J=7.0 Hz), 7.39 (2H, s), 7.41 (1H, s), 7.60–7.92 (2H, m), 8.46 (1H, t, J=5.9 Hz)

EXAMPLE 175

The following compound was obtained according to a similar manner to that of Example 166.

4-(6-Acetylaminomethylpyridin-2 -yl)-2-[(amino)-(n-hexylamino)methyleneamino]thiazole NMR (DMSO-d$_6$, δ): 0.87 (3H, t, J=6.5 Hz), 1.18–1.64 (8H, m), 1.93 (3H, s), 3.12–3.30 (2H, m), 4.37 (2H, d, J=5.9 Hz), 7.16 (1H, d, J=7.2 Hz), 7.36 (2H, s), 7.40 (1H, s), 7.71 (1H, d, J=7.2 Hz), 7.79 (1H, t, J=7.2 Hz), 8.45 (1H, t, J=5.9 Hz)

EXAMPLE 176

The following compound was obtained according to a similar manner to that of Example 166.

4-(6-Acetylaminomethylpyridin-2-yl)-2-[(amino)(isopropylamino)methyleneamino]thiazole NMR (DMSO-d$_6$, δ): 1.15 (6H, d, J=6.4 Hz), 1.93 (3H, s), 3.80–4.00 (1H, m), 4.37 (2H, d, J=5.9 Hz), 7.16 (1H, d, J=7.4 Hz), 7.37 (2H, s), 7.41 (1H, s), 7.71 (1H, d, J=7.4 Hz), 7.80 (1H, t, J=7.4 Hz), 8.45 (1H, t, J=5.9 Hz)

EXAMPLE 177

The following compound was obtained according to a similar manner to that of Example 166.

4-(6-Acetylaminomethylpyridin-2-yl)-2-[(amino)-(isopentylamino)methyleneamino]thiazole NMR (DMSO-d$_6$, δ): 0.92 (6H, d, J=6.6 Hz), 1.35–1.50 (2H, m), 1.57–1180 (1H, m), 1.93 (3H, s), 3.14–3.28 (2H, m), 4.37 (2H, d, J=5.9 Hz), 7.16 (1H, d, J=7.3 Hz), 7.36 (2H, s), 7.40 (1H, s), 7.71 (1H, d, J=7.3 Hz), 7.80 (1H, t, J=7.3 Hz), 8.45 (1H, t, J=5.9 Hz)

EXAMPLE 178

The following compound was obtained according to a similar manner to that of Example 166.

4-(6-Acetylaminomethylpyridin-2-yl)-2-[(amino)allylamino)methyleneamino]thiazole NMR (DMSO-d$_6$, δ): 1.93 (3H, s), 3.80–3.93 (2H, 4.37 (2H, d, J=5.9 Hz), 5.07–5.32 (2H, m), 5.81–6.01 (1H, m), 7.17 (1H, dd, J=1.9 Hz and 10 6.7 Hz), 7.44 (1H, s), 7.49 (2H, s), 7.70–7.86 (2H, m), 8.45 (1H, t, J=5.9 Hz)

EXAMPLE 179

The following compound was obtained according to a similar manner to that of Example 166.

4-(6-Acetylaminomethylpyridin-2-yl)-2-[(amino)cyclopentylamino)methyleneamino]thiazole NMR (DMSO-d$_6$, δ): 1.32–1.80 (6H, m), 1.80–2.03 (2H, m), 1.93 (3H, s), 3.92–4.12 (1H, m), 4.37 (2H, d, J=5.8 Hz), 7.16 (1H, d, J=7.5 Hz), 7.33 (2H, s), 7.40 (1H, s), 7.70 (1H, d, J=7.5 Hz), 7.80 (1H, t, J=7.5 Hz), 8.45 (1H, t, J=5.8 Hz)

EXAMPLE 180

The following compound was obtained according to a similar manner to that of Example 166.

4-(6-Acetylaminomethylpyridin-2-yl)-2-[(amino)(cyclopropylamino)methyleneamino]thiazole NMR (DMSO-d$_6$, δ): 1.40–1.88 (4H, m), 1.93 (3H,s), 3.35–3.55 (1H, m), 4.37 (2H, d, J=5.7 Hz), 7.17 (1H, d, J=7.6 Hz), 7.40 (1H, s), 7.60 (2H, s), 7.69 (1H, d, J=7.6 Hz), 7.81 (1H, t, J=7.6 Hz), 8.45 (1H, t, J=5.7 Hz)

EXAMPLE 181

The following compound was obtained according to a similar manner to that of Example 166.

4-(6-Acetylaminomethylpyridin-2-yl)-2-[(amino)(-piperidino)methyleneamino]thiazole NMR (DMSO-d$_6$, δ): 1.40–1.70 (6H, m), 1.93 (3H, s), 3.45–3.60 (4H, m), 4.37 (2H, d, J=5.9 Hz), 7.17 (1H, d, J=7.4 Hz), 7.44 (1H, s), 7.68 (1H, d, J=7.4 Hz), 7.81 (1H, t, J=7.4 Hz), 8.24 (2H, s), 8.45 (1H, t, J=5.9 Hz)

EXAMPLE 182

The following compound was obtained according to a similar manner to that of Example 166.

4-(6-Acetylaminomethylpyridin-2-yl)-2-[(amino)(-morpholino)methyleneamino]thiazole NMR (DMSO-d6, δ): 1.93 (3H, s), 3.47–3.58 (4H, m), 3.58–3.70 (4H, m), 4.37 (2H, d, J=5.9 Hz), 7.17 (1H, d, J=7.5 Hz), 7.49 (1H, s), 7.67 (1H, d, J=7.5 Hz), 7.81 (1H, t, J=7.5 Hz), 8.30 (2H, s), 8.45 (1H, t, J=5.9 Hz)

EXAMPLE 183

The following compound was obtained according to a similar manner to that of Example 166.

2-[(Amino)(methylamino)methyleneamino]-4 -(6-propionylaminomethylpyridin-2-yl)thiazole mp: 169°–170° C. IR (Nujol): 3400, 3350, 3250, 1630, 1600 cm$^{-1}$ NMR (DMSO-d6, δ): 8.38 (1H, t, J=5.9 Hz), 8.00–7.60 (2H, m), 7.45 (2H, s), 7.40 (1H, 7.15 (1H, dd, J=2.2 Hz and 6.5 Hz), 4.38 (2H, J=5.9 Hz), 2.77 (3H, d, J=4.8 Hz), 2.21 (2H, q, J=7.6 Hz), 1.06 (3H, t, J=7.6 Hz) Anal. Calcd. for $C_{14}H_{18}N_6OS$: C 52.81, H 5.70, N 26.39 Found: C 53.10, H 5.72, N 25.94

EXAMPLE 184

The following compound was obtained according to a similar manner to that of Example 166.

2-[(Amino)(n-butylamino)methyleneamino]-4-(6-propionylaminomethylpyridin-2-yl)thiazole mp: 145°–147° C.

IR (Nujol): 3330, 3230, 3120, 1650, 1610 cm$^{-1}$ NMR (DMSO-d6, δ): 8.38 (1H, t, J=5.9 Hz), 7.80 (1H, t, J=7.4 Hz), 7.71 (1H, dd, J=ca. 1.0 Hz and 7.4 Hz), 7.40 (1H, s), 7.38 (2H, s), 7.15 (1H, dd, J=ca. 1.0 Hz and 7.4 Hz), 4.38 (2H, d, J=5.9 Hz), 3.24–3.15 (2H, m), 2.21 (2H, q, J=7.6 Hz), 1.54–1.28 (4H, m), 1.06 (3H, t, J=7.6 Hz), 0.92 (3H, t, J=7.0 Hz) Anal. Calcd. for $C_{17}H_{24}N_6OS$: C 56.64, H 6.71, N 23.31 Found: C 56.98, H 6.91, N 23.23

EXAMPLE 185

The following compound was obtained according to a similar manner to that of Example 166.

2-[(Amino)(cyclohexylamino)methyleneamino]-4-(6-propionylaminomethylpyridin-2-yl)thiazole IR (Nujol): 3320, 1650 cm$^{-1}$ NMR (DMSO-d6, δ): 8.38 (1H, t, J=5.9 Hz), 7.80 (1H, t, J=7.5 Hz), 7.70 (1H, dd, J=ca. 1.0 Hz and 7.5 Hz), 7.39 (1H, s), 7.33 (2H, s), 7.15 (1H, dd, J=ca. 1.0 Hz and 7.5 Hz), 4.37 (2H, d, J=5.9 Hz), 3.66–3.54 (1H, m), 2.21 (2H, q, J=7.6 Hz), 1.90–1.80 (2H, m), 1.80–1.45 (3H, m), 1.45–1.10 (5H, m), 1.06 (3H, t, J=7.6 Hz)

EXAMPLE 186

The following compound was obtained according to a similar manner to that of Example 166.

2-[(Amino)(methylamino)methyleneamino]-4-(6-ethoxycarbonylaminomethylpyridin-2-yl)thiazole NMR (DMSO-d6, δ): 7.85–7.66 (3H, m), 7.47 (2H, s), 7.39 (1H, s), 7.17 (1H, dd, J=1.9 Hz and 6.8 Hz), 4.31 (2H, d, J=6.1 Hz), 4.04 (2H, q, J=7.1 Hz), 2.77 (3H, d, J=4.7 Hz), 1.19 (3H, t, J=7.1 Hz)

EXAMPLE 187

The following compound was obtained according to a similar manner to that of Example 166.

2-[(Amino)(n-butylamino)methyleneamino]-4-(6-ethoxycarbonylaminomethylpyridin-2-yl)thiazole mp: 141°–142° C. IR (Nujol): 3430, 3340, 3230, 1705, 1650, 1610 cm$^{-1}$ NMR (DMSO-d6, δ): 7.85–7.70 (3H, m), 7.38 (3H, s), 7.17 (1H, dd, J=ca. 1.0 Hz and 6.4 Hz), 4.30 (2H, d, J=6.1 Hz), 4.04 (2H, q, J=7.1 Hz), 3.19 (2H, q, J=6.4 Hz), 1.51–1.03 (7H, m), 0.92 (3H, t, J=7.0 Hz)

EXAMPLE 188

A suspension of 2-(diaminomethyleneamino)-4-(5-methoxycarbonylpyridin-3-yl)thiazole (2.0 g), cyclopentylamine (3.7 g) and 28% sodium methoxide methanolic solution (5 ml) in methanol (50 ml) was refluxed for 2 hours. The solvent was removed under reduced pressure. The residue was dissolved in water (50 ml). The mixture was extracted with a mixture of ethyl acetate (150 ml) and tetrahydrofuran (50 ml). The extract was dried over magnesium sulfate and then was evaporated. Recrystallization from a mixture of methanol and diisopropyl ether afforded 4-(5-cyclopentylaminocarbonylpyridin-3-yl)-2-(diaminomethyleneamino)thiazole (0.2 g).

mp: 243°–244° C (dec.) IR (Nujol): 3430, 3370, 3060, 1630, 1590 cm$^{-1}$ NMR (DMSO-d6, δ): 9.16 (1H, d, J=2.0 Hz), 8.85 (1H, d, J=2.0 Hz), 8.56 (1H, d, J=7.0 Hz), 8.48 (1H, t, J=2.0 Hz), 7.43 (1H, s), 6.94 (4H, s), 4.4–4.15 (1H, m), 2.05–1.85 (2H, m), 1.85–1.45 (6H, m) Anal. Calcd. for $C_{15}H_{18}N_6OS$: C 54.53, H 5.49, N 25.44 Found: C 54.24, H 5.58, N 25.33

EXAMPLE 189

The following compound was obtained according to a similar manner to that of Example 188.

4-(5-Cyclohexylaminocarbonylpyridin-3-yl)-2-(diaminomethyleneamino)thiazole mp: 213°–214° C. (dec.) IR (Nujol): 3400, 3280, 3060, 1630, 1590 cm$^{-1}$ NMR (DMSO-d6, δ): 9.16 (1H, d, J=2.1 Hz), 8.85 (1H, d, J=2.1 Hz), 8.49–8.47 (2H, m), 7.43 (1H, s), 6.96 (4H, s), 4.00–3.80 (1H, m), 2.00–1.50 (4H, m), 1.50–1.00 (6H, m)

EXAMPLE 190

The following compound was obtained according to a similar manner to that of Example 188.

4-(5-Cycloheptylaminocarbonylpyridin-3-yl)-2-(diaminomethyleneamino)thiazole mp: 213°–214° C. (dec.) IR (Nujol): 3410, 3350, 1640, 1600 cm$^{-1}$ NMR (DMSO-d6, δ): 9.16 (1H, d, J=2.1 Hz), 8.84 (1H, d, J=2.1 Hz), 8.53 (1H, d, J=7.7 Hz), 8.48 (1H, t, J=2.1 Hz), 7.42 (1H, s), 6.95 (4H, s), 4.10–3.90 (1H, m), 2.00–1.00 (12H, m)

EXAMPLE 191

A suspension of 4-(2-aminomethylthiazol-4-yl)-2-(diaminomethyleneamino)thiazole dihydrochloride (2.0 g), cycloheptanecarboxylic acid (1.02 g), 1-(3-dimethylaminopropyl)-3-ethylcarbodiimide hydrochloride (1.50 g), 1-hydroxybenzotriazole hydrate (1.07 g) and triethylamine (1.24 g) in N,N-dimethylformamide (50 ml) was stirred at room temperature for 2 hours. The solvent was removed under reduced pressure. The residue was suspended in water (200 ml). The mixture was alkalized to pH 11 with a saturated aqueous potassium carbonate solution and then extracted with a mixture of ethyl acetate (250 ml) and tetrahydrofuran (50 ml). The extract was dried over magnesium sulfate and then was evaporated. The residue was chromatographed on a silica gel column eluting with a mixture of chloroform and methanol =10:1. Recrystallization from a mixture of methanol, tetrahydrofuran and diisopropyl ether afforded 4-(2-cycloheptanecarbonylaminomethylthiazol-4-yl)-2-(diaminomethyleneamino)thiazole (0.72 g).

mp: 243°–245° C. (dec.) IR (Nujol): 3370, 1650, 1610 cm$^{-1}$ NMR (DMSO-d$_6$, δ): 8.64 (1H, t, J=6.0 Hz), 7.76 (1H, s), 7.01 (1H, s), 6.89 (4H, s), 4.52 (2H, d, J=6.0 Hz), 2.45–2.25 (1H, m), 2.00–1.30 (12H, m) Anal. Calcd. for C$_{16}$H$_{22}$N$_6$OS$_2$: C 50.77, H 5.86, N 22.20 Found: C 50.37, H 5.99, N 22.50

EXAMPLE 192

The following compound was obtained according to a similar manner to that of Example 191.

4-(2-Cyclohexylmethanecarbonylaminomethyl-thiazol-4-yl)-2-(diaminomethyleneamino)thiazole mp: 245°–247° C. (dec.) IR (Nujol): 3410, 3330, 1635, 1610 cm$^{-1}$ NMR (DMSO-d$_6$, δ): 8.73 (1H, t, J=6.0 Hz), 7.78 (1H, s), 7.00 (1H, s), 6.88 (4H, s), 4.54 (2H, d, J=6.0 Hz), 2.05 (2H, d, J=6.8 Hz), 1.82–1.50 (6H, m), 1.40.–1.10 (3H, m), 1.10–0.70 (2H, m) Anal. Calcd. for C$_{16}$H$_{22}$N$_6$OS$_2$: C 50.77, H 5.86, N 22.20 Found: C 50.89, H 5.87, N 22.11

EXAMPLE 193

The following compound was obtained according to a similar manner to that of Example 166.

2-[(Amino)(methylamino)methyleneamino]-4-(2-acetylaminomethylthiazol-4-yl)thiazole mp: 190°–192° C. IR (Nujol): 3390, 3250, 1630 cm$^{-1}$ NMR (DMSO-d$_6$, δ): 8.73 (1H, t, J=6.0 Hz), 7.78 (1H, s), 7.41 (2H, s), 7.03 (1H, s), 4.54 (2H, d, J=6.0 Hz), 2.76 (3H, d, J=4.8 Hz), 1.92 (3H, s)

What we claim is:

1. A compound of the formula:

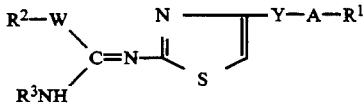

wherein R$^1$ is amino, ureido, lower alkanoylamino, lower alkoxycarbonylamino, lower alkylsulfonylamino, lower alkoxy(lower)alkanoylamino, mono or di or trihalo(lower)alkanoylamino, hydroxy(lower)alkanoylamino, protected hydroxy(lower)alkanoylamino, lower alkoxycarbonyl(lower)alkoxy(lower)alkanoylamino, lower alkylthio(lower)alkanoylamino, mono or di (lower)alkylamino(lower)alkanoylamino, furyl(lower)alkylthioalkanoylamino, lower alkylureido, (C$_3$–C$_7$)-cycloalkanecarbonylamino, (C$_3$–C$_7$)-cycloalkanecarbonylamino having oxo, lower alkyl(C$_3$–C$_7$)-cycloalkanecarbonylamino, furoylamino, nicotinoylamino, (C$_3$–C$_7$)-cycloalkenylamino having amino and oxo, imido, triazolylamino substituted by amino and lower alkyl, benzoisothiazolylamino substituted by oxo, 2-cyano-3-lower alkylguanidino, 2-lower alkanesulfonyl-3-lower alkylguanidino, 2-lower alkanesulfonylguanidino, (1-lower alkylamino-2-nitrovinyl)amino, hydroxy, halogen, cyano, carbamoyl, lower alkoxycarbonyl, benzimidazolylthio or a group of the formula:

in which R$^4$ is hydrogen or sulfamoyl, and R$^5$ is amino or lower alkoxy,

R$^2$ is hydrogen, lower alkyl, lower alkoxy(lower)alkyl, di(lower)alkylamino(lower)alkyl, (C$_3$–C$_7$)-cycloalkyl, lower alkenyl or mono or di or trihalo(lower)alkyl, R$^3$ is hydrogen or lower alkyl; or R$^2$ and R$^3$ are linked together to form lower alkylene, Y is

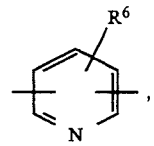

in which R$^6$ is hydrogen,

A is lower alkylene, and

W is NH; or

R$^2$-W is piperidino or morpholino, or pharmaceutically acceptable salt thereof.

2. A compound of claim 1, wherein R$^1$ is lower alkanoylamino or ureido.

3. A compound of claim 2, which is selected from the group consisting of 4-(6-acetylaminomethylpyridin-2-yl)-2-(diaminomethyleneamino)thiazole or its mono- or di-hydrochloride, 2-(2-diaminomethyleneamino)-4-(6-ureidomethylpyridin-2-yl)thiazole or its mono- or di-hydrochloride, and 4-(6-acetylaminomethylpyridin-2-yl)-2-[(amino)(n-butylamino)methyleneamino]thiazole.

4. A compound of claim 2, which is 4-(6-acetylaminomethylpyridin-2-yl)-2-[(amino)(methylamino)methyleneamino]thiazole.

5. A pharmaceutical composition which comprises, as an active ingredient, a compound of claim 1 or a pharmaceutically acceptable salt thereof in admixture with pharmaceutically acceptable carriers.

6. A method for the therapeutic treatment of ulcer which comprises administering an effective amount of a compound of claim 1 or a pharmaceutically acceptable salt thereof to human or animals.

* * * * *